US005977322A

United States Patent [19]
Marks et al.

[11] Patent Number: 5,977,322
[45] Date of Patent: Nov. 2, 1999

[54] HIGH AFFINITY HUMAN ANTIBODIES TO TUMOR ANTIGENS

[75] Inventors: James D. Marks, Kensington; Robert Schier, San Francisco, both of Calif.

[73] Assignee: The Regents of the University of California, Oakland, Calif.

[21] Appl. No.: 08/665,202

[22] Filed: Jun. 13, 1996

Related U.S. Application Data

[60] Provisional application No. 60/000,238, Jun. 14, 1995, and provisional application No. 60/000,250, Jun. 15, 1995.

[51] Int. Cl.⁶ .............................. C07K 16/30; C12P 21/08
[52] U.S. Cl. .............................. 530/388.85; 530/388.15; 530/388.22; 530/388.8; 530/387.3; 530/387.7
[58] Field of Search ........................... 530/388.8, 388.15, 530/387.3, 387.7, 388.22, 388.85; 435/6, 235.1

[56] References Cited

U.S. PATENT DOCUMENTS 5,169,774 12/1992 Frankel et al. .

FOREIGN PATENT DOCUMENTS

92/22653 12/1992 WIPO .

OTHER PUBLICATIONS

Huston, James S. et al., (1988) "Protein engineering of antibody binding sites: Recovery of specific activity in an anti–digoxin single–chain Fv analogue produced in *Escherichia coli*", *Proc. Natl. Acad. Sci., USA*, 85:5879–5883.
Vallera, Daniel A., (1994) "Immunotoxins: Will Their Clinical Promise Be Fulfilled?", *Blood*, 83(2):309–317.
Trail, P.A. et al., (1993) "Cure of Xenografted Human Carcinomas by BR96–Doxorubicin Immunoconjugates", *Science*, 261:212–215.
Weiner, L.M. et al., (1989) "Phase I Evaluation of an Anti–Breast Carcinoma Monoclonal Antibody 260F9–Recombinant Ricin A Chain Immunoconjugate", *Cancer Res.*, 49:4062–4067.
Riethmuller, G. et al., (1992) "Monoclonal antibodies in the detection and therapy of micrometastatic epithelial cancers", *Curr. Opin. Immunol.*, 4:647–655.
Brinkmann, U. et al., (1993) "A recombinant immunotoxin that is active on prostate cancer cells and that is composed of the Fv region of monoclonal antibody PR1 and a truncated form of Pseudomonas exotoxin", *Proc. Natl. Acad. Sci. USA*, 90:547–551.
Colcher, D. et al., (1988) "Radioimmunolocalization of Human Carcinoma Xenografts with B72.3 Second Generation Monoclonal Antibodies", *Cancer Res.*, 48:4597–4603.
Gallinger, S. et al., (1993) "Comparative Dual Label Study of First and Second Generation Antitumor–associated Glycoprotein–72 Monoclonal Antibodies in Colorectal Cancer Patients", *Cancer Res.*, 53:271–278.
Adams, Gregory et al., (1993) "Highly Specific in Vivo Tumor Targeting by Monovalent and Divalent Forms of 741F8 Anti–c–erbB–2 Single–Chain Fv1", *Cancer Res.*, 53:4026–4034.
Hoogenboom, H.R. et al., (1992) "Building antibodies from their genes", *Immunol. Rev.*, 130:41–68.

Marks, J.D. et al., (1991) "By–passing Immunization: Human Antibodies from V–gene Libraries Displayed on Phage", *J. Mol. Biol.*, 222:581–597.
Marks, J.D. et al., (1992) "By–passing Immunization: Building High Affinity Human Antibodies by Chain Shuffling", *Bio/Technology*, 10:779–783.
Hawkins, R.E. et al., (1992) "Selection of Phage Antibodies by Binding Affinity Mimicking Affinity Maturation", *J. Miol. Biol.*, 226:889–896.
Reichman, L. et al., (1993) "Phage Display and Selection of a Site–Directed Randomized Single–Chain Antibody Fv Fragment for Its Affinity Improvement", *Biochemistry*, 32:8848–8855.
McCafferty, J. et al., (1990) "Phage antibodies: filmentous phage displaying antibody variable domains", *Nature*, 348:552–554.
Griffiths, A.D. et al., (1993) "Human anti–self antibodies with high specificity from phage display libraries", *EMBO J.*, 12:725–734.
Clackson, Tim et al., (1991) "Making antibody fragments using phage display libraries", *Nature*, 352:624–628.
Group, E.B.C.T.C., (1992) "Systematic Treatment of Early Breast Cancer by Hormonal, Cytotoxic, or Immune Therapy", *Lancet*, 339:1–15.
Allred, D.C. et al., (1992) "Overexpression of HER–2/neu and its relationship with other prognostic factors change during the progression of in situ to invasive breast cancer", *Hum. Path.*, 23:974–979.
Slamon, D.J. et al., (1987) "Human Breast Cancer: Correlation of Relapse and Survival with Amplification of the HER–2/neu Oncogene", *Scienc*, 235:177–182.
Carter, P. et al., (1994) "Towards and Immunotherapy for p185HER2 overexpressing tumors", *Antigen & Antibody Engineering in Breast Cancer Diagnosis*, pp. 83–94.
Shepard, H.M. et al., (1991) "Monoclonal Antibody Therapy of Human Cancer: Taking the HER2 Protooncogene to the Clinic", *J. Clin. Immunol.*, 11:117–127.
Soderlind, Eskil et al., (1992) "Phase Display Technology in Antibody Engineering: Design of Phagemid Vectors and in vitro Maturation Systems", *Immunological Reviews*, 130:109–124.
Dsis et al (1994) *Cancer Res.* 54:16–20.
Borrebaeck (1989) *J. Immunol.* 123:157–165.

*Primary Examiner*—Paula K. Hutzell
*Assistant Examiner*—Geetha P. Bansal
*Attorney, Agent, or Firm*—Townsend and Townsend and Crew LLP

[57] ABSTRACT

This invention provides novel human antibodies that specifically bind to human c-erbB-2. In one embodiment, the antibodies are single chain antibodies initially developed by phage display against a c-erbB-2 target. The resulting antibodies (designated C6 antibodies) show improved specificity and affinity for c-erbB-2. In addition, since the C6 antibodies are both relatively small and fully human they are less immunogenic in humans than other (e.g., full-size or chimeric) anti-c-erbB-2 antibodies. The C6 antibodies may be used alone or as components of chimeric molecules that specifically target and deliver effector molecules to cells overexpressing c-erbB-2.

40 Claims, 5 Drawing Sheets

```
              10           20            30            40
               *            *             *             *
        CAG GTG CAG CTG TTG CAG TCT GGG GCA GAG TTG AAA AAA CCC GGG GAG
        Gln Val Gln Leu Leu Gln Ser Gly Ala Glu Leu Lys Lys Pro Gly Glu>
        ___a___a___a___a___TRANSLATION OF ERB6 [A]_a___a___a___a___a___>

50           60            70            80            90
           *            *             *             *             *
        TCT CTG AAG ATC TCC TGT AAG GGT TCT GGA TAC AGC TTT ACC AGC TAC
        Ser Leu Lys Ile Ser Cys Lys Gly Ser Gly Tyr Ser Phe Thr Ser Tyr>
        ___a___a___a___a___TRANSLATION OF ERB6 [A]_a___a___a___a___a___>

100          110           120           130           140
              *            *             *             *             *
        TGG ATC GCC TGG GTG CGC CAG ATG CCC GGG AAA GGC CTG GAG TAC ATG
        Trp Ile Ala Trp Val Arg Gln Met Pro Gly Lys Gly Leu Glu Tyr Met>
        ___a___a___a___a___TRANSLATION OF ERB6 [A]_a___a___a___a___a___>

150          160           170           180           190
              *            *             *             *             *
        GGG CTC ATC TAT CCT GGT GAC TCT GAC ACC AAA TAC AGC CCG TCC TTC
        Gly Leu Ile Tyr Pro Gly Asp Ser Asp Thr Lys Tyr Ser Pro Ser Phe>
        ___a___a___a___a___TRANSLATION OF ERB6 [A]_a___a___a___a___a___>

200          210           220           230           240
              *            *             *             *             *
        CAA GGC CAG GTC ACC ATC TCA GTC GAC AAG TCC GTC AGC ACT GCC TAC
        Gln Gly Gln Val Thr Ile Ser Val Asp Lys Ser Val Ser Thr Ala Tyr>
        ___a___a___a___a___TRANSLATION OF ERB6 [A]_a___a___a___a___a___>

250          260           270           280
              *            *             *             *
        TTG CAA TGG AGC AGT CTG AAG CCC TCG GAC AGC GCC GTG TAT TTT TGT
        Leu Gln Trp Ser Ser Leu Lys Pro Ser Asp Ser Ala Val Tyr Phe Cys>
        ___a___a___a___a___TRANSLATION OF ERB6 [A]_a___a___a___a___a___>

290          300           310           320           330
         *            *             *             *             *
        GCG AGA CAT GAC GTG GGA TAT TGC AGT AGT TCC AAC TGC GCA AAG TGG
        Ala Arg His Asp Val Gly Tyr Cys Ser Ser Ser Asn Cys Ala Lys Trp>
        ___a___a___a___a___TRANSLATION OF ERB6 [A]_a___a___a___a___a___>

340          350           360           370           380
         *            *             *             *             *
        CCT GAA TAC TTC CAG CAT TGG GGC CAG GGC ACC CTG GTC ACC GTC TCC
        Pro Glu Tyr Phe Gln His Trp Gly Gln Gly Thr Leu Val Thr Val Ser>
        ___a___a___a___a___TRANSLATION OF ERB6 [A]_a___a___a___a___a___>

390          400           410           420           430
         *            *             *             *             *
        TCA GGT GGA GGC GGT TCA GGC GGA GGT GGC TCT GGC GGT GGC GGA TCG
        Ser Gly Gly Gly Gly Ser Gly Gly Gly Gly Ser Gly Gly Gly Gly Ser>
        ___a___a___a___a___TRANSLATION OF ERB6 [A]_a___a___a___a___a___>

440          450           460           470           480
              *            *             *             *             *
        CAG TCT GTG TTG ACG CAG CCG CCC TCA GTG TCT GCG GCC CCA GGA CAG
        Gln Ser Val Leu Thr Gln Pro Pro Ser Val Ser Ala Ala Pro Gly Gln>
        ___a___a___a___a___TRANSLATION OF ERB6 [A]_a___a___a___a___a___>
```

FIG. 1.

```
              490          500          510          520
               *            *            *            *        .
AAG GTC ACC ATC TCC TGC TCT GGA AGC AGC TCC AAC ATT GGG AAT AAT
Lys Val Thr Ile Ser Cys Ser Gly Ser Ser Ser Asn Ile Gly Asn Asn>
___a___a___a___a___TRANSLATION OF ERB6 [A]_a___a___a___a___a___>

530          540          550          560          570
    *            *            *            *            *    .
TAT GTA TCC TGG TAC CAG CAG CTC CCA GGA ACA GCC CCC AAA CTC CTC
Tyr Val Ser Trp Tyr Gln Gln Leu Pro Gly Thr Ala Pro Lys Leu Leu>
___a___a___a___a___TRANSLATION OF ERB6 [A]_a___a___a___a___a___>

580          590          600          610          620
        *            *            *            *            *
ATC TAT GGT CAC ACC AAT CGG CCC GCA GGG GTC CCT GAC CGA TTC TCT
Ile Tyr Gly His Thr Asn Arg Pro Ala Gly Val Pro Asp Arg Phe Ser>
___a___a___a___a___TRANSLATION OF ERB6 [A]_a___a___a___a___a___>

630          640          650          660          670
        *            *            *            *            *
GGC TCC AAG TCT GGC ACC TCA GCC TCC CTG GCC ATC AGT GGG TTC CGG
Gly Ser Lys Ser Gly Thr Ser Ala Ser Leu Ala Ile Ser Gly Phe Arg>
___a___a___a___a___TRANSLATION OF ERB6 [A]_a___a___a___a___a___>

680          690          700          710          720
            *            *            *            *            *
TCC GAG GAT GAG GCT GAT TAT TAC TGT GCA GCA TGG GAT GAC AGC CTG
Ser Glu Asp Glu Ala Asp Tyr Tyr Cys Ala Ala Trp Asp Asp Ser Leu>
___a___a___a___a___TRANSLATION OF ERB6 [A]_a___a___a___a___a___>

730          740          750          760
          *            *            *            *         .
AGT GGT TGG GTG TTC GGC GGA GGG ACC AAG CTG ACC GTC CTA GGT GCG
Ser Gly Trp Val Phe Gly Gly Gly Thr Lys Leu Thr Val Leu Gly Ala>
___a___a___a___a___TRANSLATION OF ERB6 [A]_a___a___a___a___a___>

770
 *
GCC GCA
Ala Ala>
___a___>
```

HIGH AFFINITY HUMAN ANTIBODIES TO TUMOR ANTIGENS

This application is a continuation-in-part of United States Provisional Applications U.S. Ser. No. 60/000,238 and U.S. Ser. No. 60/000,250, filed on Jun. 14, 1995 and Jun. 15, 1995 respectively. These applications are incorporated by reference for all purposes.

The invention was made by or under a contract with the following agencies of the United States Government: Army Grant No. DAMD17-94-J-4433 and the Department of Health and Human Services, National Institutes of Health, Grant No. U01 CA51880.

BACKGROUND OF THE INVENTION

This invention pertains to the fields of immunodiagnostics and immunotherapeutics. In particular, this invention pertains to the discovery of novel human antibodies that specifically bind to c-erbB-2, and to chimeric molecules containing these antibodies.

Conventional cancer chemotherapeutic agents cannot distinguish between normal cells and tumor cells and hence damage and kill normal proliferating tissues. One approach to reduce this toxic side effect is to specifically target the chemotherapeutic agent to the tumor. This is the rationale behind the development of immunotoxins, chimeric molecules composed of an antibody either chemically conjugated or fused to a toxin that binds specifically to antigens on the surface of a tumor cell thereby killing or inhibiting the growth of the cell (Frankel et al. *Ann. Rev. Med.,* 37: 127 (1986)). The majority of immunotoxins prepared to date, have been made using murine monoclonal antibodies (Mabs) that exhibit specificity for tumor cells. Immunotoxins made from Mabs demonstrate relatively selective killing of tumor cells in vitro and tumor regression in animal models (id.).

Despite these promising results, the use of immunotoxins in humans has been limited by toxicity, immunogenicity and a failure to identify highly specific tumor antigens (Byers et al. *Cancer Res.,* 49: 6153). Nonspecific toxicity results from the failure of the monoclonal antibody to bind specifically and with high affinity to tumor cells. As a result, nonspecific cell killing occurs. In addition, the foreign immunotoxin molecule elicits a strong immune response in humans. The immunogenicity of the toxin portion of the immunotoxin has recently been overcome by using the human analog of RNase (Rybak et al. *Proc. Nat. Acad. Sci., USA,* 89: 3165 (1992)). The murine antibody portion, however, is still significantly immunogenic (Sawler et al., *J. Immunol.,* 135: 1530 (1985)).

Immunogenicity could be avoided and toxicity reduced if high affinity tumor specific human antibodies were available. However, the production of human monoclonal antibodies using conventional hybridoma technology has proven extremely difficult (James et al, *J. Immunol Meth.,* 100: 5 (1987)). Furthermore, the paucity of purified tumor-specific antigens makes it necessary to immunize with intact tumor cells or partially purified antigen. Most of the antibodies produced react with antigens which are also common to normal cells and are therefore unsuitable for use as tumor-specific targeting molecules.

SUMMARY OF THE INVENTION

This invention provides novel human antibodies that specifically bind to the extracellular domain of the c-erbB-2 protein product of the HER2/neu oncogene. This antigen (marker) is overexpressed on many cancers (e.g. carcinomas) and thus the antibodies of the present invention specifically bind to tumor cells that express c-erbB-2.

In a preferred embodiment, the antibody is a C6 antibody derived from the sFv antibody C6.5. The antibody may contain a variable heavy chain, a variable light chain, or both a variable heavy and variable light chain of C6.5 or its derivatives. In addition the antibody may contain a variable heavy chain, a variable light chain or both a variable heavy and variable light chain of C6.5 in which one or more of the variable heavy or variable light complementarity determining regions (CDR1, CDR2 or CDR3) has been altered (e.g., mutated). Particularly preferred CDR variants are listed in the specification and in Examples 1, 2 and 3. Particularly preferred C6 antibodies include C6.5, C6ML3-14, C6L-1 and C6MH3-B1. In various preferred embodiments, these antibodies are single chain antibodies (sFv also known as scFv) comprising a variable heavy chain joined to a variable light chain either directly or through a peptide linker. Other preferred embodiments of the C6 antibodies and C6.5, C6ML3-14, C6L1, and C6MH3-B1, in particular, include Fab, the dimer (Fab')$_2$, and the dimer (sFv')$_2$. Particularly preferred (sFv')$_2$ dimers are fusion proteins where the Sfv' components are joined through a peptide linkage or through a peptide (G$_4$S). Still other preferred C6 antibodies include an antibody selected from the group consisting of an antibody having a V$_L$ domain with one of the amino acid sequences shown in Table 10, an antibody having a V$_H$ domain with one of the amino acid sequences shown in Table 12, an antibody having a V$_L$ CDR3 domain having one of the amino acid sequences shown in Tables 4, 15, and 16, and an antibody having a V$_H$ CDR3 domain having one of the amino acid sequences shown in Tables 13 and 14. Other preferred embodiments are to be found replete throughout the specification.

In a particularly preferred embodiment, the C6 antibody has a K$_d$ ranging from about $1.6\times10^{-8}$ to about $1\times10^{-12}$ M in SK-BR-3 cells using Scatchard analysis or as measured against purified c-erbB-2 by surface plasmon resonance in a BIAcore.

In another embodiment the present invention provides for nucleic acids that encode any of the above-described C6 antibodies. The invention also provides for nucleic acids that encode the amino acid sequences of C6.5, C6ML3-14, C6L1, C6MH3-B1, or any of the other amino acid sequences encoding C6 antibodies and described in Example 1, 2 or 3. In addition this invention provides for nucleic acid sequences encoding any of these amino acid sequences having conservative amino acid substitutions.

In still another embodiment, this invention provides for proteins comprising one or more complementarity determining regions selected from the group consisting of the complementarity determining regions of Tables 10, 12, 13, 14, 15, and 16 and of any of the examples, in particular of Examples 1, 2 or 3. Other particularly preferred antibodies include any of the antibodies expressed by the clones described herein.

In still yet another embodiment, this invention provides for cells comprising a recombinant nucleic acid which is any of the above described nucleic acids.

This invention also provides for chimeric molecules that specifically bind a tumor cell bearing c-erbB-2. The chimeric molecule comprises an effector molecule joined to any of the above-described C6 antibodies. In a preferred embodiment, the effector molecule is selected from the group consisting of a cytotoxin (e.g. PE, DT, Ricin A, etc.), a label, a radionuclide, a drug, a liposome, a ligand, an antibody, and an antigen binding domain). The C6 antibody may be chemically conjugated to the effector molecule or the chimeric molecule may be expressed as a fusion protein.

This invention provides for methods of making C6 antibodies. One method proceeds by i) providing a phage library presenting a C6.5 variable heavy chain and a multiplicity of human variable light chains; ii) panning the phage library on c-erbB-2; and iii) isolating phage that specifically bind c-erbB-2. This method optionally further includes iv) providing a phage library presenting the variable light chain of the phage isolated in step iii and a multiplicity of human variable heavy chains; v) panning the phage library on c-erbB-2; and vi) isolating phage that specifically bind c-erbB-2.

Another method for making a C6 antibody proceeds by i) providing a phage library presenting a C6.5 variable light chain and a multiplicity of human variable heavy chains; ii) panning the phage library on c-erbB-2; and iii) isolating phage that specifically bind c-erbB-2.

Yet another method for making a C6 antibody involves i) providing a phage library presenting a C6.5 variable light and a C6.5 variable heavy chain encoded by a nucleic acid variable in the sequence encoding CDR1, CDR2 or CDR3 such that each phage displays a different CDR; ii) panning the phage library on c-erbB-2; and isolating the phage that specifically bind c-erbB-2.

This invention also provides a method for impairing growth of tumor cells bearing c-erbB-2. This method involves contacting the tumor with a chimeric molecule comprising a cytotoxin attached to a human C6 antibody that specifically binds c-erbB-2.

Finally, this invention provides a method for detecting tumor cells bearing c-erbB-2. This method involves contacting the biological samples derived from a tumor with a chimeric molecule comprising a label attached to a human C6 antibody that specifically binds c-erbB-2.

Definitions

The following abbreviations are used herein: AMP, ampicillin; c-erbB-2 ECD, extracellular domain of c-erbB-2; CDR, complementarity determining region; ELISA, enzyme linked immunosorbent assay; FACS, fluorescence activated cell sorter; FR, framework region; Glu, glucose; HBS, hepes buffered saline, 10 mM hepes, 150 mM NaCl, pH 7.4; IMAC, immobilized metal affinity chromatography; $k_{on}$, association rate constant; $k_{off}$, dissociation rate constant; MPBS, skimmed milk powder in PBS; MTPBS, skimmed milk powder in TPBS; PBS, phosphate buffered saline, 25 mM $NaH_2PO_4$, 125 mM NaCl, pH 7.0; PCR, polymerase chain reaction; RU, resonance units; scFv or sFv, single-chain Fv fragment; sFv': Fv containing cysteine; TPBS, 0.05% v/v Tween 20 in PBS; SPR, surface plasmon resonance; $V_k$, immunoglobulin kappa light chain variable region; $V_1$, immunoglobulin lambda light chain variable region; $V_L$, immunoglobulin light chain variable region; $V_H$, immunoglobulin heavy chain variable region; wt, wild type.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$–$C_H$1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies, more preferably single chain Fv (sFv) antibodies in which a variable heavy and a variable light chain are joined together (directly or through a peptide linker) to form a continuous polypeptide.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. *Sequences of proteins of immunological interest,* 4th ed. U.S. Dept. Health and Human Services, Public Health Services, Bethesda, Md. (1987).

As used herein, the terms "immunological binding" and "immunological binding properties" refer to the non-covalent interactions of the type which occur between an immunoglobulin molecule and an antigen for which the immunoglobulin is specific. The strength or affinity of immunological binding interactions can be expressed in terms of the dissociation constant ($K_d$) of the interaction, wherein a smaller Kd represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) and the "off rate constant" ($k_{off}$) can be determined by calculation of the concentrations and the actual rates of association and dissociation. The ratio of $k_{off}/k_{on}$ enables cancellation of all parameters not related to affinity and is thus equal to the dissociation constant $K_d$. See, generally, Davies et al. *Ann. Rev. Biochem.,* 59: 439–473 (1990).

The term "C6 antibody", as used herein refers to antibodies derived from C6.5 whose sequence is expressly provided herein. C6 antibodies preferably have a binding affinity of about $1.6 \times 10^8$ or better and are preferably derived by screening (for affinity to c-erbB-2) a phage display library in which a known C6 variable heavy ($V_H$) chain is expressed in combination with a multiplicity of variable light ($V_L$) chains or conversely a known C6 variable light chain is expressed in combination with a multiplicity of variable heavy ($V_H$) chains. C6 antibodies also include those antibodies produced by the introduction of mutations into the variable heavy or variable light complementarity determining regions (CDR1, CDR2 or CDR3) as described herein. Finally C6 antibodies include those antibodies produced by any combination of these modification methods as applied to C6.5 and its derivatives.

A single chain Fv ("sFv" or "scFv") polypeptide is a covalently linked $V_H::V_L$ heterodimer which may be expressed from a nucleic acid including $V_H$- and $V_L$-encoding sequences either joined directly or joined by a peptide-encoding linker. Huston, et al. *Proc. Nat. Acad. Sci. USA,* 85: 5879–5883 (1988). A number of structures for converting the naturally aggregated—but chemically separated light and heavy polypeptide chains from an antibody V region into an sFv molecule which will fold into a three dimensional structure substantially similar to the structure of an antigen-binding site. See, e.g. U.S. Pat. Nos. 5,091,513 and 5,132,405 and 4,956,778.

In one class of embodiments, recombinant design methods can be used to develop suitable chemical structures (linkers) for converting two naturally associated—but chemically separate—heavy and light polypeptide chains from an antibody variable region into a sFv molecule which will fold into a three-dimensional structure that is substantially similar to native antibody structure.

Design criteria include determination of the appropriate length to span the distance between the C-terminal of one chain and the N-terminal of the other, wherein the linker is generally formed from small hydrophilic amino acid residues that do not tend to coil or form secondary structures. Such methods have been described in the art. See, e.g., U.S. Pat. Nos. 5,091,513 and 5,132,405 to Huston et al.; and U.S. Pat. No. 4,946,778 to Ladner et al.

In this regard, the first general step of linker design involves identification of plausible sites to be linked. Appropriate linkage sites on each of the $V_H$ and $V_L$ polypeptide domains include those which will result in the minimum loss of residues from the polypeptide domains, and which will necessitate a linker comprising a minimum number of residues consistent with the need for molecule stability. A pair of sites defines a "gap" to be linked. Linkers connecting the C-terminus of one domain to the N-terminus of the next generally comprise hydrophilic amino acids which assume an unstructured configuration in physiological solutions and preferably are free of residues having large side groups which might interfere with proper folding of the $V_H$ and $V_L$ chains. Thus, suitable linkers under the invention generally comprise polypeptide chains of alternating sets of glycine and serine residues, and may include glutamic acid and lysine residues inserted to enhance solubility. One particular linker under the invention has the amino acid sequence $[(Gly)_4Ser]_3$ (SEQ ID NO:1). Another particularly preferred linker has the amino acid sequence comprising 2 or 3 repeats of $[(Ser)_4Gly]$ (SEQ ID NO:2) such as $[(Ser)_4Gly]_3$ (SEQ ID NO:3). Nucleotide sequences encoding such linker moieties can be readily provided using various oligonucleotide synthesis techniques known in the art. See, e.g., Sambrook, supra.

The phrase "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, C6 antibodies can be raised to the c-erbB-2 protein that bind c-erbB-2 and not to other proteins present in a tissue sample. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

A chimeric molecule is a molecule in which two or more molecules that exist separately in their native state are joined together to form a single molecule having the desired functionality of all of its constituent molecules. While the chimeric molecule may be prepared by covalently linking two molecules each synthesized separately, one of skill in the art will appreciate that where the chimeric molecule is a fusion protein, the chimera may be prepared de novo as a single "joined" molecule.

The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

BRIEF DESCRIPTION OF THE DRAWINGS

FIG. 1 illustrates the nucleic (SEQ ID NO:4) and amino acid (SEQ ID NO:5) sequence of the C6 sFv antibody C6.5.

DETAILED DESCRIPTION

Figure 2:
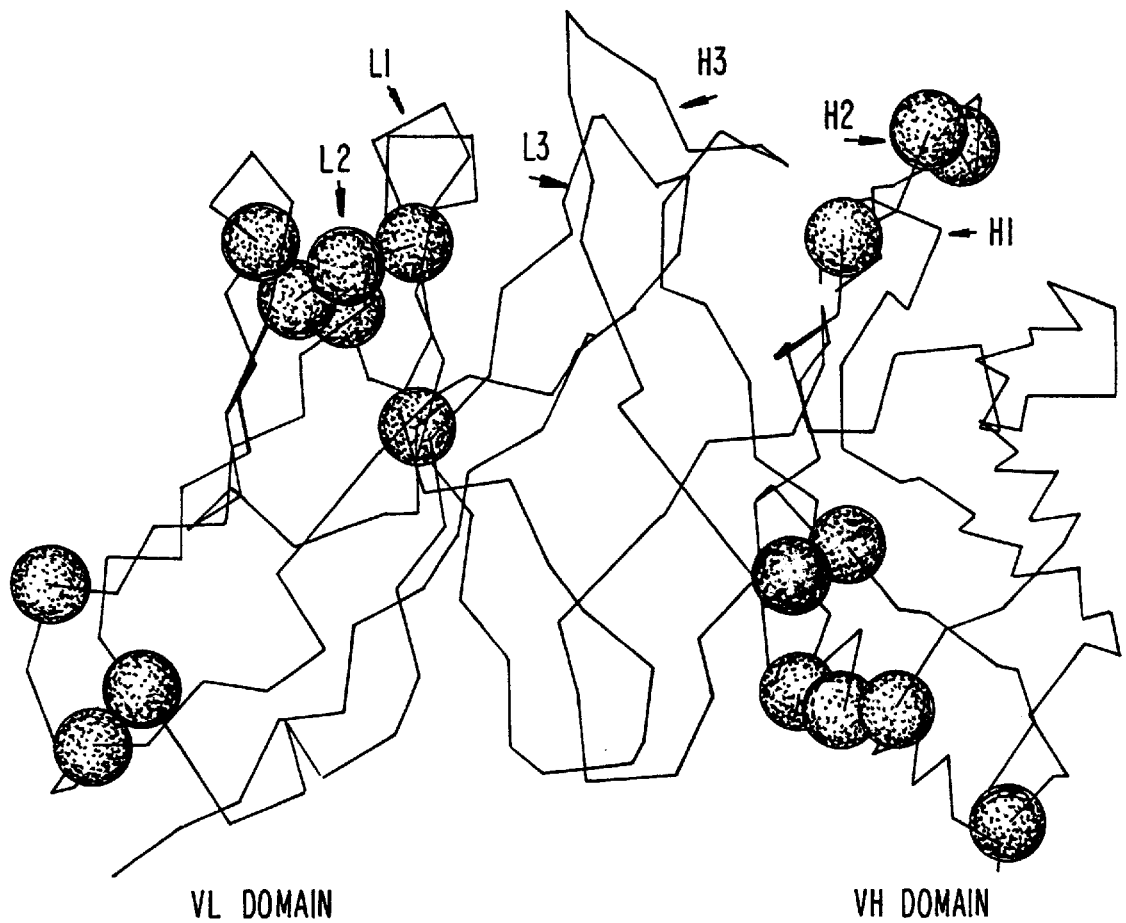
FIG. 2 shows the location of mutations in a light chain shuffled C6L1 and heavy chain shuffled C6H2 sFv. Mutations are indicated as shaded spheres on the Cα-carbon tracing of the Fv fragment of the immunoglobulin KOL (Marquart et al. (1990). H1, H2, H3, L1, L2 and L3 refer to the $V_H$ and $V_L$ antigen binding loops respectively. Mutations in C6L1 are all located in the $V_L$ domain with parental $V_H$ sequence, mutations in C6H2 are all located in the $V_H$ domain with parental $V_L$ sequence. C6L1 has no mutations located in a β-strand which forms part of the $V_H$-$V_L$ interface. C6H2 has 2 conservative mutations located in the β-strand formed by framework 3 residues.
Figure 3A:
FIG. 3 shows the locations of mutations in light chain shuffled sFv which spontaneously form dimers. Mutations are indicated as shaded spheres on the α-carbon tracing of the Fv fragment of the immunoglobulin KOL (Marquart et al., 1980) with the $V_L$ domain located on the left side of each panel. A=C6VLD; B=C6VLE; C=CdVLB; D=C6VLF. Each shuffled sFv has at least 1 mutation located in a β-strand which forms part of the $V_H$-$V_L$ interface.
Figure 3B:
Figure 3C:
Figure 3D:
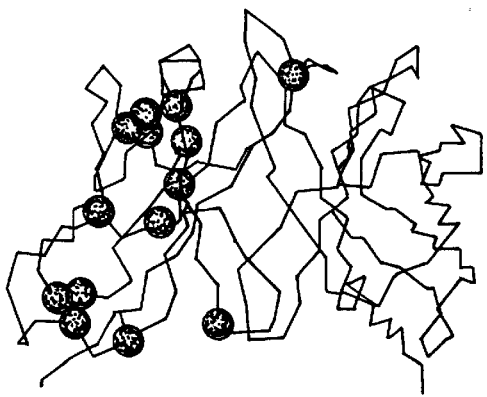

This invention provides for novel human antibodies that specifically bind to the extracellular domain of the c-erbB-2 protein product of the HER2/neu oncogene. The c-erbB-2 marker is overexpressed by 30–50% of breast carcinomas and other adenocarcinomas and thus provides a suitable cell surface marker for specifically targeting tumor cells such as carcinomas. In contrast to previous known anti-cerbB-2 antibodies, the antibodies of the present invention (designated herein as C6 antibodies) are fully human antibodies. Thus, administration of these antibodies to a human host elicits a little or no immunogenic response.

This invention additionally provides for chimeric molecules comprising the C6 antibodies of the present invention joined to an effector molecule. The C6 antibodies act as a "targeting molecule" that serves to specifically bind the chimeric molecule to cells bearing the c-erbB-2 marker thereby delivering the effector molecule to the target cell.

An effector molecule typically has a characteristic activity that is desired to be delivered to the target cell (e.g. a tumor overexpressing c-erbB-2). Effector molecules include cytotoxins, labels, radionuclides, ligands, antibodies, drugs, liposomes, and viral coat proteins that render the virus capable of infecting a c-erbB-2 expressing cell. Once delivered to the target, the effector molecule exerts its characteristic activity.

For example, in one embodiment, where the effector molecule is a cytotoxin, the chimeric molecule acts as a potent cell-killing agent specifically targeting the cytotoxin to tumor cells bearing the c-erbB-2 marker. Chimeric cytotoxins that specifically target tumor cells are well known to those of skill in the art (see, for example, Pastan et al., *Ann. Rev. Biochem.*, 61: 331–354 (1992)).

In another embodiment, the chimeric molecule may be used for detecting the presence or absence of tumor cells in vivo or in vitro or for localizing tumor cells in vivo. These methods involve providing a chimeric molecule comprising an effector molecule, that is a detectable label attached to the C6 antibody. The C6 antibody specifically binds the chimeric molecule to tumor cells expressing the c-erbB-2 marker which are then marked by their association with the detectable label. Subsequent detection of the cell-associated label indicates the presence and/or location of a tumor cell.

In yet another embodiment, the effector molecule may be another specific binding moiety including, but not limited to an antibody, an antigen binding domain, a growth factor, or a ligand. The chimeric molecule will then act as a highly specific bifunctional linker. This linker may act to bind and enhance the interaction between cells or cellular components to which the chimeric protein binds. Thus, for example, where the "effector" component is an anti-receptor antibody or antibody fragment, the C6 antibody component specifically binds c-erbB-2 bearing cancer cells, while the effector component binds receptors (e.g., IL-2, IL-4, FcγI, FcγII and FcγIII receptors) on the surface of immune cells. The chimeric molecule may thus act to enhance and direct an immune response toward target cancer cells.

In still yet another embodiment the effector molecule may be a pharmacological agent (e.g. a drug) or a vehicle containing a pharmacological agent. This is particularly suitable where it is merely desired to invoke a non-lethal biological response. Thus the C6 antibody receptor may be conjugated to a drug such as vinblastine, vindesine, melphalan, N-Acetylmelphalan, methotrexate, aminopterin, doxirubicin, daunorubicin, genistein (a tyrosine kinase inhibitor), an antisense molecule, and other pharmacological agents known to those of skill in the art, thereby specifically targeting the pharmacological agent to tumor cells expressing c-erbB-2.

Alternatively, the C6 antibody may be bound to a vehicle containing the therapeutic composition. Such vehicles include, but are not limited to liposomes, micelles, various synthetic beads, and the like.

One of skill in the art will appreciate that the chimeric molecules of the present invention optionally includes multiple targeting moieties bound to a single effector or conversely, multiple effector molecules bound to a single targeting moiety. In still other embodiment, the chimeric molecules includes both multiple targeting moieties and multiple effector molecules. Thus, for example, this invention provides for "dual targeted" cytotoxic chimeric molecules in which the C6 antibody is attached to a cytotoxic molecule while another molecule (e.g. an antibody, or another ligand) is attached to the other terminus of the toxin. Such a dual-targeted cytotoxin might comprise, e.g. a C6 antibody substituted for domain Ia at the amino terminus of a PE and anti-TAC(Fv) inserted in domain III. Other antibodies may also be suitable effector molecules.

I. Preparation of C6 Antibodies.

The C6 antibodies of this invention are prepared using standard techniques well known to those of skill in the art in combination with the polypeptide and nucleic acid sequences provided herein. The polypeptide sequences may be used to determine appropriate nucleic acid sequences encoding the particular C6 antibody disclosed thereby. The nucleic acid sequence may be optimized to reflect particular codon "preferences" for various expression systems according to standard methods well known to those of skill in the art. Alternatively, the nucleic acid sequences provided herein may also be used to express C6 antibodies.

Using the sequence information provided, the nucleic acids may be synthesized according to a number of standard methods known to those of skill in the art. Oligonucleotide synthesis, is preferably carried out on commercially available solid phase oligonucleotide synthesis machines (Needham-VanDevanter et al. (1984) *Nucleic Acids Res.* 12:6159–6168) or manually synthesized using the solid phase phosphoramidite triester method described by Beaucage et. al. (Beaucage et. al. (1981) *Tetrahedron Letts.* 22(20): 1859–1862).

Once a nucleic acid encoding a C6 antibody is synthesized it may be amplified and/or cloned according to standard methods. Molecular cloning techniques to achieve these ends are known in the art. A wide variety of cloning and in vitro amplification methods suitable for the construction of recombinant nucleic acids, e.g., encoding C6 antibody genes, are known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Nat'l Acad. Sci. USA* 86: 10029–10033.

Examples of techniques sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al., (1987) U.S. Pat. No. 4,683,202; PCR *Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; and Barringer et al. (1990) *Gene* 89, 117. Improved methods of cloning in vitro amplified nucleic acids are described in Wallace et al., U.S. Pat. No. 5,426,039.

Once the nucleic acid for a C6 antibody is isolated and cloned, one may express the gene in a variety of recombinantly engineered cells known to those of skill in the art. Examples of such cells include bacteria, yeast, filamentous fungi, insect (especially employing baculoviral vectors), and mammalian cells. It is expected that those of skill in the art are knowledgeable in the numerous expression systems available for expression of C6 antibodies.

In brief summary, the expression of natural or synthetic nucleic acids encoding C6 antibodies will typically be achieved by operably linking a nucleic acid encoding the antibody to a promoter (which is either constitutive or inducible), and incorporating the construct into an expression vector. The vectors can be suitable for replication and integration in prokaryotes, eukaryotes, or both. Typical cloning vectors contain transcription and translation terminators, initiation sequences, and promoters useful for regulation of the expression of the nucleic acid encoding the C6 antibody. The vectors optionally comprise generic expression cassettes containing at least one independent terminator sequence, sequences permitting replication of the cassette in both eukaryotes and prokaryotes, i.e., shuttle vectors, and selection markers for both prokaryotic and eukaryotic systems. See Sambrook.

To obtain high levels of expression of a cloned nucleic acid it is common to construct expression plasmids which typically contain a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky, C., 1984, *J. Bacteriol.*, 158:1018–1024 and the leftward promoter of phage lambda ($P_L$) as described by Herskowitz and Hagen, 1980, *Ann. Rev. Genet.*, 14:399–445. The inclusion of selection markers in DNA vectors transformed in *E. coli* is also useful. Examples of such markers include genes specifying resistance to ampicillin, tetracycline, or chloramphenicol. See Sambrook for details concerning selection markers, e.g., for use in *E. coli*.

Expression systems for expressing C6 antibodies are available using *E. coli*, Bacillus sp. (Palva et al. (1983) *Gene*

22:229–235; Mosbach et al., *Nature,* 302:543–545 and Salmonella. *E. coli* systems are preferred.

The C6 antibodies produced by prokaryotic cells may require exposure to chaotropic agents for proper folding. During purification from, e.g., *E. coli,* the expressed protein is optionally denatured and then renatured. This is accomplished, e.g., by solubilizing the bacterially produced antibodies in a chaotropic agent such as guanidine HCl. The antibody is then renatured, either by slow dialysis or by gel filtration. See, U.S. Pat. No. 4,511,503.

Methods of transfecting and expressing genes in mammalian cells are known in the art. Transducing cells with nucleic acids can involve, for example, incubating viral vectors containing C6 nucleic acids with cells within the host range of the vector. See, e.g., *Methods in Enzymology,* vol. 185, Academic Press, Inc., San Diego, Calif. (D. V. Goeddel, ed.) (1990) or M. Krieger, *Gene Transfer and Expression—A Laboratory Manual,* Stockton Press, New York, N.Y., (1990) and the references cited therein.

The culture of cells used in the present invention, including cell lines and cultured cells from tissue or blood samples is well known in the art. Freshney (*Culture of Animal Cells, a Manual of Basic Technique,* third edition Wiley-Liss, New York (1994)) and the references cited therein provides a general guide to the culture of cells.

Techniques for using and manipulating antibodies are found in Coligan (1991) *Current Protocols in Immunology* Wiley/Greene, NY; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, NY; and Kohler and Milstein (1975) Nature 256: 495–497. C6 antibodies which are specific for c-erbB-2 bind c-erbB-2 and have a $K_D$ of 1 $\mu$M or better, with preferred embodiments having a $K_D$ of 1 nM or better and most preferred embodiments having a $K_D$ of 0.1 nM or better.

In a preferred embodiment the C6 antibody gene (e.g. C6.5 sFv gene) is subcloned into the expression vector pUC119Sfi/NotHismyc, which is identical to the vector described by Griffiths et al., *EMBO J.,* 13: 3245–3260 (1994), (except for the elimination of an XBaI restriction site). This results in the addition of a hexa-histidine tag at the C-terminal end of the sFv. A pHEN-1 vector DNA containing the C6.5 sFv DNA is prepared by alkaline lysis miniprep, digested with NcoI and NotI, and the sFv DNA purified on a 1.5% agarose gel. The C6 sFv DNA is ligated into pUC119Sfi1/Not1Hismyc digested with NcoI and NotI and the ligation mixture used to transform electrocompetent *E.coli* HB2151. For expression, 200 ml of 2×TY media containing 100 mg/ml ampicillin and 0.1% glucose is inoculated with *E.coli* HB2151 harboring the C6 gene in pUC119Sfi1/Not1Hismyc. The culture is grown at 37° C. to an A600 nm of 0.8. Soluble sFv is expression induced by the addition of IPTG to a final concentration of 1 mM, and the culture is grown at 30° C. in a shaker flask overnight.

The C6 sFv may then be harvested from the periplasm using the following protocol: Cells are harvested by centrifugation at 4000 g for 15 min, resuspended in 10 ml of ice cold 30 mM Tris-HCl pH 8.0, 1 mM EDTA, 20% sucrose, and incubated on ice for 20 minutes. The bacteria are then pelleted by centrifugation at 6000 g for 15 min. and the "periplasmic fraction" cleared by centrifugation at 30,000 g for 20 min. The supernatant is then dialyzed overnight at 4° C. against 8 L of IMAC loading buffer (50 mM sodium phosphate pH 7.5, 500 mM NaCl, 20 mM imidazole) and then filtered through a 0.2 micron filter.

In a preferred embodiment, the C6 sFv is purified by IMAC. All steps are performed at 4° C. A column containing 2 ml of Ni-NTA resin (Qiagen) is washed with 20 ml IMAC column wash buffer (50 mM sodium phosphate pH 7.5, 500 mM NaCl, 250 mM imidazole) and 20 ml of IMAC loading buffer. The periplasmic preparation is then loaded onto the column and the column washed sequentially with 50 ml IMAC loading buffer and 50 ml IMAC washing buffer (50 mM sodium phosphate pH 7.5, 500 mM NaCl, 25 mM imidazole). Protein was eluted with 25 ml IMAC elution buffer (50 mM sodium phosphate pH 7.5, 500 mM NaCl, 100 mM imidazole) and 4 ml fractions collected. The C6 antibody may be detected by absorbance at 280 nm and sFv fraction eluted. To remove dimeric and aggregated sFv, samples can be concentrated to a volume <1 ml in a Centricon 10 (Amicon) and fractionated on a Superdex 75 column using a running buffer of HBS (10 mM Hepes, 150 mM NaCl, pH 7.4).

The purity of the final preparation may be evaluated by assaying an aliquot by SDS-PAGE. The protein bands can be detected by Coomassie staining. The concentration can then be determined spectrophotometrically, assuming that an $A_{280}$ nm of 1.0 corresponds to an sFv concentration of 0.7 mg/ml.

II. Modification of C6 Antibodies.

A) Display of antibody fragments on the surface of bacteriophage (phage display).

Display of antibody fragments on the surface of viruses which infect bacteria (bacteriophage or phage) makes it possible to produce human sFvs with a wide range of affinities and kinetic characteristics. To display antibody fragments on the surface of phage (phage display), an antibody fragment gene is inserted into the gene encoding a phage surface protein (pIII) and the antibody fragment-pIII fusion protein is expressed on the phage surface (McCafferty et al. (1990) *Nature,* 348: 552–554; Hoogenboom et al. (1991) *Nucleic Acids Res.,* 19: 4133–4137). For example, a sFv gene coding for the $V_H$ and $V_L$ domains of an anti-lysozyme antibody (D1.3) was inserted into the phage gene III resulting in the production of phage with the DI.3 sFv joined to the N-terminus of pIII thereby producing a "fusion" phage capable of binding lysozyme (McCafferty et al (1990) *Nature,* 348: 552–554).

Since the antibody fragments on the surface of the phage are functional, phage bearing antigen binding antibody fragments can be separated from non-binding or lower affinity phage by antigen affinity chromatography (McCafferty et al. (1990) *Nature,* 348: 552–554). Mixtures of phage are allowed to bind to the affinity matrix, non-binding or lower affinity phage are removed by washing, and bound phage are eluted by treatment with acid or alkali. Depending on the affinity of the antibody fragment, enrichment factors of 20 fold-1,000,000 fold are obtained by single round of affinity selection. By infecting bacteria with the eluted phage, however, more phage can be grown and subjected to another round of selection. In this way, an enrichment of 1000 fold in one round becomes 1,000,000 fold in two rounds of selection (McCafferty et al. (1990) *Nature,* 348: 552–554). Thus, even when enrichments in each round are low (Marks et al. (1991) *J. Mol. Biol,* 222: 581–597), multiple rounds of affinity selection leads to the isolation of rare phage and the genetic material contained within which encodes the sequence of the binding antibody. The physical link between genotype and phenotype provided by phage display makes it possible to test every member of an antibody fragment library for binding to antigen, even with libraries as large as 100,000,000 clones. For example, after multiple rounds of selection on antigen, a binding sFv that occurred with a frequency of only 1/30,000,000 clones was recovered (Marks et al (1991) *J. Mol. BioL,* 222: 581–597).

Analysis of binding is simplified by including an amber codon between the antibody fragment gene and gene III. This makes it possible to easily switch between displayed and soluble antibody fragments simply by changing the host bacterial strain. When phage are grown in a supE suppresser strain of *E. coli,* the amber stop codon between the antibody gene and gene III is read as glutamine and the antibody fragment is displayed on the surface of the phage. When eluted phage are used to infect a non-supressor strain, the amber codon is read as a stop codon and soluble antibody is secreted from the bacteria into the periplasm and culture media (Hoogenboom et al. (1991) *Nucleic Acids Res.,* 19: 4133–4137). Binding of soluble sFv to antigen can be detected, e.g., by ELISA using a murine IgG monoclonal antibody (e.g., 9E1O) which recognizes a C-terminal myc peptide tag on the sFv (Evan et al. (1985) *Mol. Cell Biol.,* 5: 3610–3616; Munro et al. (1986) *Cell,* 46: 291–300), e.g., followed by incubation with polyclonal anti-mouse Fc conjugated to horseradish peroxidase.

B) Phage display can be used to increase antibody affinity.

To create higher affinity antibodies, mutant sFv gene repertories, based on the sequence of a binding sFv, are created and expressed on the surface of phage. Higher affinity sFvs are selected on antigen as described above and in Examples 1 and 2. One approach for creating mutant sFv gene repertoires has been to replace either the $V_H$ or $V_L$ gene from a binding sFv with a repertoire of nonimmune $V_H$ or $V_L$ genes (chain shuffling) (Clackson et al. (1991) *Nature,* 352: 624–628). Such gene repertoires contain numerous variable genes derived from the same germline gene as the binding sFv, but with point mutations (Marks et al. (1992) *Bio/Technology,* 10: 779–783). Using light chain shuffling and phage display, the binding avidities of a human sFv antibody fragment can be dramatiaclly increased. See, e.g., Marks et al *Bio/Technology,* 10: 779–785 (1992) in which the affinity of a human sFv antibody fragment which bound the hapten phenyloxazolone (phox) was increased from 300 nM to 15 nM (20 fold) (Marks et al. (1992) *Bio/Technology,* 10: 779–783).

C) Isolation and characterization of C6.5. a human sFv which binds c-erbB-2.

Isolation and characterization of C6.5 is described in detail in the Examples below. Human sFvs which bound to c-erbB-2 were isolated by selecting the nonimmune human sFv phage antibody library (described in Example 1) on c-erbB-2 extracellular domain peptide immobilized on polystyrene. After five rounds of selection, 45 of 96 clones analyzed (45/96) produced sFv which bound c-erb-B2 by ELISA. Restriction fragments analysis and DNA sequencing revealed the presence of two unique human sFvs, C4 and C6.5. Both of these sFvs bound only to c-erbB-2 and not to a panel of 10 irrelevant antigens. Cell binding assays, however, indicated that only C6.5 bound c-erb-B2 expressed on cells, and thus this sFv was selected for further characterization.

D) Purification of C6.5.

To facilitate purification, the C6.5 sFv gene was subcloned into the expression vector pUC119 Sfi-NotmycHIS which results in the addition of the myc peptide tag followed by a hexahistidine tag at the C-terminal end of the sFv. The vector also encodes the pectate lyase leader sequence which directs expression of the sFv into the bacterial periplasm where the leader sequence is cleaved. This makes it possible to harvest native properly folded sFv directly from the bacterial periplasm. Native C6.5 sFv was expressed and purified from the bacterial supernatant using immobilized metal affinity chromatography. The yield after purification and gel filtration on a Superdex 75 column was 10.5 mg/L. Other C6 antibodies may be purified in a similar manner.

E) Measurement of C6.5 affinity for c-erbB-2.

As explained above, selection for increased avidity involves measuring the affinity of a C6 antibody (e.g. a modified C6.5) for c-erbB-2. Methods of making such measurements are described in detail in Examples 1 and 2. Briefly, for example, the Kd of C6.5 and the kinetics of binding to c-erbB-2 were determined in a BIAcore, a biosensor based on surface plasmon resonance. For this technique, antigen is coupled to a derivatized sensor chip capable of detecting changes in mass. When antibody is passed over the sensor chip, antibody binds to the antigen resulting in an increase in mass which is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. Rate constant $k_{on}$ is typically measured in the range $1.0 \times 10^2$ to $5.0 \times 10^6$ and $k_{off}$ in the range $1.0 \times 10^{-1}$ to $1.0 \times 10^{-6}$. The equilibrium constant $K_d$ is often calculated as $k_{off}/k_{on}$ and thus is typically measured in the range $10^{-5}$ to $10^{-12}$. Affinities measured in this manner correlate well with affinities measured in solution by fluorescence quench titration.

F) Affinity of C6.5 for c-erbB-2.

The kinetics of binding and affinity of purified C6.5 were determined by BIAcore and the results are shown in Table 2. The $K_d$ of $1.6 \times 10^{-8}$ M determined by BIAcore is in close agreement to the $K_d$ determined by Scatchard analysis after radioiodination ($2.0 \times 10^{-8}$ M). C6.5 has a rapid $k_{on}$, and a relatively rapid $k_{off}$. The rapid $k_{off}$ correlates with the in vitro measurement that only 22% of an injected dose is retained on the surface of SK-OV-3 cells after 30 minutes. Biodistribution of C6.5 was determined and the percent injected dose/gm tumor at 24 hours was 1.1% with tumor/organ ratios of 5.6 for kidney and 103 for bone. These values compare favorably to values obtained for 741F8 sFv. 741F8 is a monoclonal antibody capable of binding c-erbB-2 (see, e.g., U.S. Pat. No. 5,169,774). The $K_d$ of 741F8 was also measured by BIAcore and agreed with the value determined by scatchard analysis (Table 1).

TABLE 1

Characterization of anti-cerbB-2 sFv species. Characteristics of the murine anti-cerbB-2 sFv, 741F8, and the human sFv C6.5 are compared. The affinity and dissociation constants were determined by Scatchard plot analysis, unless otherwise stated. Dissociation from c-erbB-2 positive (SK-OV-3) cells was measured in an in vitro live cell assay. The percentage of injected dose per gram (% ID/g) tumor and tumor to organ ratios were determined in biodistribution studies performed in separate groups of scid mice (n = 10–14) bearing SK-OV-3 tumors overexpressing c-erbB-2. SEM are <35% of the associated values. a = significantly improved (p < 0.05) compared to 741F8 sFv.

| Parameter | 741F8 | C6.5 |
|---|---|---|
| $K_d$ (BIAcore) | $2.6 \times 10^{-8}$ M | $1.6 \times 10^{-8}$ M |
| $K_d$ (Scatchard) | $5.4 \times 10^{-8}$ M | $2.1 \times 10^{-8}$ M |
| $k_{on}$ (BIAcore) | $2.4 \times 10^5$ M$^{-1}$ s$^{-1}$ | $4.0 \times 10^5$ M$^{-1}$ s$^{-1}$ |
| $k_{off}$ (BIAcore) | $6.4 \times 10^{-3}$ s$^{-1}$ | $6.3 \times 10^{-3}$ s$^{-1}$ |
| % associated with cell surface at 15 min | 32.7% | 60.6% |
| % associated with cell surface at 30 min | 8.6% | 22.2% |
| % ID/g Tumor | 0.8 | 1.0 |
| T:Blood | 14.7 | 22.9 |
| T:Kidney | 2.8 | 5.6a |
| T:Liver | 14.2 | 22.3 |
| T:Spleen | 10.3 | 34.1 |
| T:Intestine | 25.0 | 29.7 |
| T:Lung | 9.4 | 15.8 |
| T:Stomach | 8.9 | 11.1 |
| T:Muscle | 78.8 | 158.7 |
| T:Bone | 30.0 | 102.7 |

These results show that a human sFv which binds specifically to c-erbB-2 with moderate affinity was been produced. The sFv expresses at high level in *E. coli* as native sFv, and can be easily purified in high yield in two steps. Techniques are known for the rapid and efficiently purification of sFv from the bacterial periplasm and to measure affinity without the need for labeling.

G) Estimating the affinity of unpurified sFv for c-erbB2.

Phage display and selection generally results in the selection of higher affinity mutant sfvs (Marks et al. (1992) *Bio/Technology*, 10: 779–783; Hawlins et al. (1992) *J. Mol. Biol.* 226: 889–896; Riechmann et al. (1993) *Biochemistry*, 32: 8848–8855; Clackson et al. (1991) *Nature*, 352: 624–628), but probably does not result in the separation of mutants with less than a 6 fold difference in affinity (Riechmann et al. (1993) *Biochemistry*, 32: 8848–8855). Thus a rapid method is needed to estimate the relative affinities of mutant sfvs isolated after selection. Since increased affinity results primarily from a reduction in the $k_{off}$, measurement of $k_{off}$ should identify higher affinity sFv. $k_{off}$ can be measured in the BLkcore on unpurified sFv in bacterial periplasm, since expression levels are high enough to give an adequate binding signal and $k_{off}$ is independent of concentration. The value of $k_{off}$ for periplasmic and purified sFv is in close agreement (Table 2).

TABLE 2

Comparison of $k_{off}$ determined on sFv in bacterial periplasm and after purification by IMAC and gel filtration.

| sFv | $k_{off}$ (s$^{-1}$) |
|---|---|
| C6-5 periplasm | $5.7 \times 10^{-3}$ |
| C6-5 purified | $6.3 \times 10^{-3}$ |
| C6-5ala3 periplasm | $9.3 \times 10^{-3}$ |
| C6-5ala3 purified | $1.5 \times 10^{-3}$ |
| C6-5ala10 periplasm | $3.7 \times 10^{-3}$ |
| C6-5ala10 purified | $4.1 \times 10^{-3}$ |

Ranking of sFv by $k_{off}$, and hence relative affinity, can be determined without purification. Determination of relative affinity without purification significantly increases the rate at which mutant sFv are characterized, and reduces the number of mutant sFv subcloned and purified which do not show improved binding characteristics over C6.5 (see results of light chain shuffling and randomization below).

H) Increasing the affinity of C6.5 by chain shuffling.

To alter the affinity of C6.5, a mutant sFv gene repertoire was created containing the VH gene of C6.5 and a human VL gene repertoire (light chain shuffling). The sFv gene repertoire was cloned into the phage display vector pHEN-1 (Hoogenboom et al. (1991) *Nucleic Acids Res.*, 19: 4133–4137) and after transformation a library of $2 \times 10^5$ transformants was obtained. Phage were prepared and concentrated as described in Example 1 or 2.

Selections were performed by incubating the phage with biotinylated c-erbB-2 in solution. The antigen concentration was decreased each round, reaching a concentration less than the desired $K_d$ by the final rounds of selection. This results in the selection of phage on the basis of affinity (Hawkins et al. (1992) *J. Mol. Biol.* 226: 889–896). After four rounds of selection, 62/90 clones analyzed produced sFv which bound c-erbB-2 by ELISA. Single chain Fv was expressed from 48 ELISA positive clones (24 from the 3rd round of selection and 24 from the 4th round of selection), the periplasm harvested, and the sFv $k_{off}$ determined by BIAcore. Single-chain Fvs were identified with a $k_{off}$ three times slower than C6.5. The light chain gene of 10 of these sFvs was sequenced. One unique light chain was identified, C6L1. This sFv was subcloned into the hexahistidine vector, and expressed sFv purified by IMAC and gel filtration. Affinity was determined by BIAcore (Table 3).

TABLE 3

Affinity and kinetics of binding of C6.5 light and heavy chain shuffled mutant sFv.

| sFv clone | $K_d$ (M) | $k_{on}$ (M$^{-1}$ s$^{-1}$) | $k_{off}$ (s$^{-1}$) |
|---|---|---|---|
| C6.5 | $1.6 \times 10^{-8}$ | $4.0 \times 10^5$ | $6.3 \times 10^{-3}$ |
| C6L1 (light chain shuffle) | $2.6 \times 10^{-9}$ | $7.8 \times 10^5$ | $2.0 \times 10^{-3}$ |
| C6VHB-4 (heavy chain shuffle) | $4.8 \times 10^{-9}$ | $1.25 \times 10^6$ | $6.0 \times 10^{-3}$ |
| C6VHC (heavy chain shuffle) | $3.1 \times 10^{-9}$ | $8.4 \times 10^5$ | $2.6 \times 10^{-3}$ |

For heavy chain shuffling, the C6.5 VH CDR3 and light chain were cloned into a vector containing a human VH gene repertoire to create a phage antibody library of $1 \times 10^6$ transformants. Selections were performed on biotinylated c-erbB-2 and after four rounds of selection, 82/90 clones analyzed produced sFv which bound c-erbB-2 by ELISAsFv was expressed from 24 ELISA positive clones (24 from the 3rd round of selection and 24 from the 4th round of selection), the periplasm harvested, and the sFv $k_{off}$ determined by BIAcore. Two clones were identified which had slower $k_{off}$ than C6.5 (C6VHB-4 and C6VHC-4). Both of these were subcloned, purified, and affinities determined by BIAcore (Table 3). The affinity of C6.5 was increased 5 fold by heavy chain shuffling and 6 fold by light chain shuffling.

I) Increasing the affinity of C6-5 by site directed mutagenesis of the third CDR of the light chain.

The majority of antigen contacting amino acid side chains are located in the complementarity determining regions (CDRs), three in the $V_H$ (CDR1, CDR2, and CDR3) and three in the $V_L$ (CDR1, CDR2, and CDR3) (Chothia et al. (1987) *J. Mol. Biol.*, 196: 901–917; Chothia et al. (1986) *Science*, 233: 755–8; Nhan et al. (1991) *J. Mol. Biol.*, 217: 133–151). These residues contribute the majority of binding energetics responsible for antibody affinity for antigen. In other molecules, mutating amino acids which contact ligand has been shown to be an effective means of increasing the affinity of one protein molecule for its binding partner (Lowman et al. (1993) *J. Mol. Biol.*, 234: 564–578; Wells (1990) *Biochemistry*, 29: 8509–8516). Thus mutation (randomization) of the CDRs and screening against c-erbB-2 may be used to generate C6 antibodies having improved binding affinity.

PCR. The resulting sFv gene repertoire was cloned into pCANTAB5E (Pharmacia) to create a phage antibody library of $1\times10^7$ transformants. The mutant phage antibody library was designated C6VLCDR3.

Selection of the C6.5 mutant VL CDR3 library (C6VLCDR3) was performed on biotinylated c-erbB-2 as described above for light chain shuffling. After three rounds of selection 82/92 clones analyzed produced sFv which bound c-erbB-2 by ELISA and after 4 rounds of selection, 92/92 clones analyzed produced sFv which bound c-erbB-2. Single-chain Fv was expressed from 24 ELISA positive clones from the 3rd and 4th rounds of selection, the periplasm harvested, and the $k_{off}$ determined by BIAcore. The best clones had a $k_{off}$ approximately 5 to 10 times slower than that of C6.5. The light chain genes of 12 sFvs with the slowest $k_{off}$ times from the 3rd and fourth round of selection were sequenced and each unique sFv subcloned into pUC119 Sfi-NotmycHis. Single-chain Fv was expressed, purified by IMAC and gel filtration, and sFv affinity and binding kinetics determined by BIAcore (Table 4). Mutant sFv were identified with 16 fold increased affinity for c-erbB-2.

TABLE 4

Amino acid sequence, affinity, and binding kinetics of sFv isolated from a library of C6.5 mutants. Table identified mutants isolated after the third and fourth rounds of selection. The entire VL CDR3 of C6.5 is shown with the residues subjected to mutagenesis (89-95b) underlined. Rate constants $k_{on}$ and $k_{off}$ were measured on purified and gel filtered sFv by SPR in a BIAcore and the Kd calculated. A hyphen "-"indicates that there is no change from the C6.5 $V_L$ CDR3 sequence at that position.

| sFv clone | $V_L$ CDR3 sequence | $k_d$ (M) | $k_{on}$ (M$^{-1}$ s$^{-1}$) | $k_{off}$ (s$^{-1}$) | SEQ ID NO |
|---|---|---|---|---|---|
| C6.5 | 8          9          9<br>9         5ab       7<br>AAWDDSLSGWV | $1.6 \times 10^{-8}$ | $4.0 \times 10^5$ | $6.3 \times 10^{-3}$ | 6 |
| 3rd Round of selection: | | | | | |
| C6ML3-5 | ———————Y——————— | $3.2 \times 10^{-9}$ | $5.9 \times 10^5$ | $1.9 \times 10^{-3}$ | 7 |
| C6ML3-2 | ————————H—————— | $2.8 \times 10^{-9}$ | $7.1 \times 10^5$ | $2.0 \times 10^{-3}$ | 8 |
| C6ML3-6 | —S———Y——————— | $3.2 \times 10^{-9}$ | $5.9 \times 10^5$ | $1.9 \times 10^{-3}$ | 9 |
| C6ML3-1 | ———————Y——W——— | $6.7 \times 10^{-9}$ | $3.0 \times 10^5$ | $2.0 \times 10^{-3}$ | 10 |
| C6ML3-3 | —T————YA———— | $4.3 \times 10^{-9}$ | $4.6 \times 10^5$ | $2.0 \times 10^{-3}$ | 11 |
| C6ML3-7 | ——————YAV——— | $2.6 \times 10^{-9}$ | $6.5 \times 10^5$ | $1.7 \times 10^{-3}$ | 12 |
| C6ML3-4 | —S—EY———W——— | $3.5 \times 10^{-9}$ | $4.0 \times 10^5$ | $1.4 \times 10^{-3}$ | 13 |
| 4th Round of selection: | | | | | |
| C6ML3-12 | ———————Y—R——— | $1.6 \times 10^{-9}$ | $4.5 \times 10^5$ | $7.2 \times 10^{-4}$ | 14 |
| C6ML3-9 | —S———YT——— | $1.0 \times 10^{-9}$ | $6.1 \times 10^5$ | $9.2 \times 10^{-4}$ | 15 |
| C6ML3-10 | ———E—PWY——— | $2.3 \times 10^{-9}$ | $6.1 \times 10^5$ | $1.4 \times 10^{-3}$ | 16 |
| C6ML3-11 | ———————YA—W——— | $3.6 \times 10^{-9}$ | $6.1 \times 10^5$ | $2.2 \times 10^{-3}$ | 17 |
| C6ML3-13 | —————AT—W——— | $2.4 \times 10^{-9}$ | $8.7 \times 10^5$ | $2.1 \times 10^{-3}$ | 18 |
| C6ML3-8 | —————HLRW——— | $2.6 \times 10^{-9}$ | $6.5 \times 10^5$ | $1.7 \times 10^{-3}$ | 19 |
| C6ML3-23 | —S——H———W——— | $1.5 \times 10^{-9}$ | $6.7 \times 10^5$ | $1.7 \times 10^{-3}$ | 20 |
| C6ML3-19 | —S———RP—W——— | $1.5 \times 10^{-9}$ | $6.7 \times 10^5$ | $1.0 \times 10^{-3}$ | 21 |
| C6ML3-29 | ————GT—W——— | $2.7 \times 10^{-9}$ | $12.9 \times 10^5$ | $2.2 \times 10^{-3}$ | 22 |
| C6ML3-15 | ————RP—W——— | $2.2 \times 10^{-9}$ | $5.9 \times 10^5$ | $1.3 \times 10^{-3}$ | 23 |
| C6ML3-14 | —————P—W——— | $1.0 \times 10^{-9}$ | $7.7 \times 10^5$ | $7.7 \times 10^{-4}$ | 24 |

For example, to increase the affinity of C6.5 for c-erbB-2, nine amino acid residues located in VL CDR3 (residues 89-95b, numbering according to Kabat et al. (1987) supra.; Table 2). were partially randomized by synthesizing a 'doped' oligonucleotide in which the wild type nucleotide occurred with a frequency of 49%. The oligonucleotide was used to amplify the remainder of the C6.5 sFv gene using Partial randomization of a single CDR ($V_L$ CDR3) resulted in the creation of mutant sFvs with 16 fold higher affinity for c-erbB-2, indicating that CDR randomization is an effective means of creating higher affinity sFv. The results also show that the method of selecting and identifying higher affinity sFv by reducing soluble antigen concentration during selections and screening periplasms by BIAcore prior to sequencing, subcloning and purification provides an effective way to isolate high affinity antibodies.

J) Creation of C6.5 (sFv')$_2$ and (sFv)$_2$ homodimers and effect on affinity and binding kinetics for cerbB-2.

To create C6 (sFv')$_2$ antibodies, two C6 sFvs are joined through a disulfide bond, or linker (e.g., a carbon linker) between the two cysteines. To create C6 (sFv)$_2$, two C6 sFv are joined directly through a peptide bond or through a peptide linker. Thus, for example, to create disulfide linked C6.5 sFv', a cysteine residue was introduced by site directed mutagenesis between the myc tag and hexahistidine tag at the carboxy-terminus of C6.5. Introduction of the correct sequence was verified by DNA sequencing. The construct is in pUC119, the pelB leader directs expressed sFv' to the periplasm and cloning sites (NcoI and NotI) exist to introduce C6.5 mutant sFv'. This vector is called pUC119/C6.5 mycCysHis. Expressed sFv' has the myc tag at the C-terminus, followed by 2 glycines, a cysteine, and then 6 histidines to facilitate purification by IMAC. After disulfide bond formation between the two cysteine residues, the two sFv' are separated from each other by 26 amino acids (two 11 amino acid myc tags and 4 glycines). An sFv' was expressed from this construct, purified by IMAC, and analyzed by gel filtration. The majority of the sFv' was monomeric. To produce (sFv')$_2$ dimers, the cysteine was reduced by incubation with 1 MM beta-mercaptoethanol, and half of the sFv' blocked by the addition of DTNB. Blocked and unblocked sFv's were incubated together to form (sFv')$_2$ and the resulting material analyzed by gel filtration. 50% of the monomer was converted to (sFv')$_2$ homodimer as determined by gel filtration and nonreducing polyacrylamide gel electrophoresis. The affinity of the C6.5 sFv' monomer and (sFv')2 dimer were determined by BIAcore (Table 5). The apparent affinity (avidity) of C6.5 increases 40 fold when converted to an (sFv')$_2$ homodimer.

TABLE 5

Affinities and binding kinetics of C6.5 sFv and C6.5 (sFv')$_2$

| Clone | $K_d$ (M) | $k_{on}$ (M$^{-1}$ s$^{-1}$) | $k_{off}$ (s$^{-1}$) |
| --- | --- | --- | --- |
| C6.5 monomer | 1.6 × 10$^{-8}$ | 4.0 × 10$^5$ | 6.3 × 10$^{-3}$ |
| C6.5 dimer | 4.0 × 10$^{-10}$ | 6.7 × 10$^5$ | 2.7 × 10$^{-4}$ |

The C6.5 (sFv')$_2$ exhibits a significant avidity effect compared to the sFv. Thus, this approach increases antibody fragment affinity, while remaining below the renal threshold for excretion.

In a particularly preferred embodiment, the (sFv)$_2$ dimer is expressed as a diabody (Holliger et al. (1993) Proc. Natl. Acad. Sci. USA, 90: 6444–6448; and WO 94/13804). This yields a bivalent molecule consisting of two C6.5 sFv polypeptide chains, since the VH and VL on the same peptide chain cannot pair. The production of a peptide linked C6.5 diabody is described in Example 5, below. In this example, the peptide linker sequence between the VH and VL domains was shortened from 15 amino acids to 5 amino acids. Synthetic oligonucleotides encoding the 5 amino acid linker (Gly$_4$Ser) (SEQ ID NO:25) were used to PCR amplify the C6.5 V$_H$ and V$_L$ genes which were then spliced together to create the C6.5 diabody gene. The gene was then cloned into an appropriate vector, expressed, and purified according to standard methods well known to those of skill in the art. In another preferred embodiment, the (sFv)$_2$ dimer is produced using a longer peptide liner that permits the Vh and Vl to pair, yielding a single polypeptide chain with two C6 binding sites.

K) Effect of sFv affinity on in vitro cell binding and in vivo biodistribution.

As described in the preceding section, chain-shuffled and point-mutation variants of C6.5 have been prepared with $K_d$ ranging from 1.0×10-$^6$ M to 1.0×10-$^9$ M. The mutant sFv have been used to examine the effects of binding affinity and kinetics on in vitro cell binding and on in vivo biodistribution. Cell surface retention assays demonstrate that higher affinity sFv are retained to a much greater extent than lower affinity sFv. For sFv of approximately the same affinity, sFv with slower $k_{off}$ are better retained on the cell surface. In competitive binding assays, all of the molecules compete in a dose dependent fashion with biotinylated C6.5 for c-erbB-2 on the surface of SK-BR-3 cells.

Twenty four hour biodistribution studies were performed in scid micebearing s.c. SK-OV-3 tumors to examine the role of affinity in the specificity and degree of tumorretention. These assays employed $^{125}$I-labeled forms of C6.5, C6G98A, C6ML3-9 and a negative control sFv at a dose of 25 mg. The c-erbB-2-specific sFv were selected to provide the following stepwise increase in affinity; C6G98A (3.2× 10$^{-7}$), C6.5 (1.6×10$^{-8}$) and C6ML3-9 (1.0×10$^{-9}$). The biodistribution studies revealed a close correlation between the affinity and the % ID/g of the radioiodinated sFv retained in tumor. The greatest degree of tumor retention was observed with $^{125}$I-C6ML3-9 (1.42±0.23% ID/g). Significantly less tumor retention was achieved with $^{125}$I-C6.5 (0.80±0.07% ID/g) (p=0.0306). Finally, the tumor retention of the lowest affinity clone $^{125}$I-C6G98A (0.19±0.04% ID/g) was significantly less than that of C6.5 (p=0.00001) and was identical to that of the negative control $^{125}$I-26-10. The T:O ratios also reflected the greater retention of higher-affinity species in tumor. For example, tumor:blood ratios of 17.2, 13.3, 3.5 and 2.6, and tumor to liver ratios of 26.2, 19.8, 4.0 and 3.1 were observed for C6ML3-9, C6.5, C6G98A and 26-10, respectively.

These results demonstrate that selective tumor retention of sFv molecules correlates with their affinity properties. With further increases in affinity, additional improvements in tumor retention are observed.

L) Approach to produce higher affinity human sFv.

As described above and in Examples 1 and 2, a C6 antibody (e.g. C6.5 sFv), which binds specifically to c-erbB-2, is expressed at high level in E. coli as native protein, and can be simply purified in high yield. Optimized techniques for creating large C6.5 mutant phage antibody libraries and developed techniques for efficiently selecting higher affinity mutants from these libraries are provided. These techniques were used to increase C6.5 affinity 16 fold, to 1.0×10$^{-8}$ M, by randomizing VL CDR3, and 5 and 6 fold by heavy and light chain shuffling respectively.

To further increase affinity, mutant C6.5 phage antibody libraries can be created where the other CDRs are randomized (V$_L$ CDR1 and CDR2 and V$_H$ CDR1, CDR2 and CDR3). Each CDR is randomized in a separate library, using, for example, C6ML3-9 as a template ($K_d$=1.0×10$^{-9}$ M). In a preferred embodiment, CDRs can be sequentially randomized, using the highest affinity sFv as the template for the next round of mutagenesis. This approach would be preferred when mutating CDRs that pack on each other, for example VL and VH CDR3. In another embodiment, CDRs could be mutated in parallel, and mutations combined to achieve an additive effect on affinity. This approach has been used to increase the affinity of human growth hormone (hGH) for the growth hormone receptor over 1500 fold from $3.4 \times 10^{-10}$ to $9.0 \times 10^{-13}$ M (Lowman et al. (1993) *J. Mol. Biol.*, 234: 564–578.

$V_H$ CDR3 occupies the center of the binding pocket, and thus mutations in this region are likely to result in an increase in affinity (Clackson et al. (1995) *Science*, 267: 383–386). In one embodiment, four $V_H$ CDR3 residues at a time are randomized using the nucleotides NNS. To create the library, an oligonucleotide is synthesized which anneals to the C6.5 $V_H$ framework 3 and encodes $V_H$ CDR3 and a portion of framework 4. At the four positions to be randomized, the sequence NNS is used, where N=any of the 4 nucleotides, and S=C or T. The oligonucleotide are used to amplify the C6.5 $V_H$ gene using PCR, creating a mutant C6.5 VH gene repertoire. PCR is used to splice the VH gene repertoire with the C6ML3-9 light chain gene, and the resulting sFv gene repertoire cloned into the phage display vector pHEN-1. Ligated vector DNA is used to transform electrocompetent *E. coli* to produce a phage antibody library of $>1.0 \times 10^7$ clones.

To select higher affinity mutant sFv, each round of selection of the phage antibody libraries is conducted on decreasing amounts of biotinylated c-erbB-2, as described in the Examples. Typically, 96 clones from the third and fourth round of selection are screened for binding to c-erbB-2 by ELISA on 96 well plates. Single-chain Fv from twenty to forty ELISA positive clones are expressed in 10 ml cultures, the periplasm harvested, and the sFv $k_{off}$ determined by BIAcore. Clones with the slowest $k_{off}$ are sequenced, and each unique sFv subcloned into pUC119 SfiNotmycHis. Single chain Fv is expressed in 1 L cultures, and purified as described supra. Affinities of purified sFv are determined by BIAcore. Randomization of one four amino acid segment of $V_H$ CDR3 produces a C6 mutant with a $K_D$ of $1.6 \times 10^{-10}$ M (see Example 3).

M) In vitro cell binding assays, in vivo pharmacokinetic and biodistribution studies.

Once higher affinity sFv's are identified, production is scaled up to provide adequate material for in vitro cell binding assays and in vivo pharmacokinetic and biodistribution studies. Techniques for scaling up production are known. Briefly, in one embodiment, sFv is expressed in *E. coli* cultures grown in 2 liter shaker flasks. Single-chain Fv is purified from the periplasm as described above and in Examples 1 and 2. Mutant sFv of higher affinity are tested using the cell retention assay described in Examples 1 and 2. Since the $t_{1/2}$ of retention should be approximately two hours when $k_{off}$ is less than $10^{-4}$, the assay is done at 30, 60, 120, 240 minutes and 18 hour incubations. Scatchard analyses may be performed on selected samples.

These studies show that affinities measured in the BIAcore on immobilized antigen correspond to improved cell binding. The pharmacokinetic and biodistribution properties of sFv molecules with broadly different affinity characteristics are screened using labeled sFv and scid mice bearing human SK-OV-3 tumors. This serves to identify molecules with in vivo properties that make them unsuitable for use as therepeutics i.e., unexpected aggregation, or unacceptable normal organ retention properties.

Twenty four hour biodistribution results are convenient indicators of overall biodistribution properties. C6 antibodies, for example C6.5 mutants, with affinities between $1.6 \times 10^{-8}$ M and $1.0 \times 10^{-11}$ M, and which differ at least 3 to 4 fold in affinity, are screened. Mutants with similar $K_d$ but with dissimilar $k_{off}$ are also studied. A number of C6.5 series affinity variants are tested and more extensive biodistribution studies performed on molecules that differ significantly from C6.5 or the nearest affinity variant in 24 hour biodistribution characteristics. These data are used to generate tissue-specific AUC determinations, as well as tumor-:normal organ AUC ratios and MIRD estimates.

Sample molecules associated with favorable predicted human dosimetry (e.g., based upon the MIRD formulation) are assayed for their in vivo therapeutic efficacy in mice.

An affinity of $1.0 \times 10^{-11}$ can be chosen as an endpoint in this preferred embodiment because the associated $k_{off}(10^{-5})$ results in a $t_{1/2}$ for dissociation from tumor of greater than 20 hours. Higher affinity endpoints can be selected and result in even longer retention. The $t_{1/2}$ for dissociation of C6.5 is approximately 3 minutes. This invention provides optimized techniques for creating large C6.5 mutant phage antibody libraries and techniques for efficiently selecting higher affinity mutants from these libraries. A number of C6.5 mutants with affinities between $1.6 \times 10^{-8}$ M to $1.0 \times 10^{-10}$ M are provided. Combining these mutations into the same sFv produces sFv mutants with $K_d$ between $1.6 \times 10^{-10}$ M and $3.3 \times 10^{-11}$ M.

N) Preparation of C6 $(sFv)_2$, $(sFv')_2$ Fab, and $(Fab')_2$ conjugates and diabodies.

C6 antibodies such as C6.5 sFv, or a variant with higher affinity, are suitable templates for creating size and valency variants. For example, a C6.5 $(sFv')_2$ is created from the parent sFv as described above and in Example 1. An sFv' can be created by excising teh sFv gene, e.g., with NcoI and NotI from pHEN-1 or pUC119 Sfi-NotmycHis and cloned into pUC119C6.5mycCysHis, cut with NcoI and NotI. In one embodiment, expressed sFv' has a myc tag at the C-terminus, followed by 2 glycines, a cysteine, and 6 histidines to facilitate purification. After disulfide bond formation between the two cysteine residues, the two sFv should be separated from each other by 26 amino acids (e.g., two 11 amino acid myc tags and 4 glycines). SFv is expressed from this construct and purified. To produce (sFv')2 dimers, the cysteine is reduced by incubation with 1 Mm beta-mercaptoethanol, and half of the sFv blocked by the addition of DTNB. Blocked and unblocked sFv are incubated together to form (sFv')2, which is purified. This approach was used to produce C6.5 (sFv')2 dimer, which demonstrates a 40 fold higher affinity than C6.5. A (sFv')2 may be constructed for example, from C6L1 ($K_d=2.5 \times 10^{-9}$ M) and C6ML3-9 ($K_d=1.0 \times 10^{-9}$ M). As higher affinity sFv become available, their genes are similarly used to construct $(sFv')_2$.

Alternatively, C6 $(sFv)_2$ can be produced by linking the two sFv by a peptide, as described in Example 5. As higher affinity sFv become available their genes can be used to construct higher affinity (sFv)$_2$.

C6.5 based Fab are expressed in *E. coli* using an expression vector similar to the one described by Better et. al. (Better et al. (1988) *Science,* 240: 1041–1043). To create a C6.5 based Fab, the VH and VL genes are amplified from the sFv using PCR. The VH gene is cloned into a PUC119 based bacterial expression vector which provides the human IgG CH1 domain downstream from, and in frame with, the $V_H$ gene. The vector also contains the lac promoter, a pelb leader sequence to direct expressed $V_H$-CH1 domain into the periplasm, a gene 3 leader sequence to direct expressed light chain into the periplasm, and cloning sites for the light chain gene. Clones containing the correct VH gene are identified, e.g., by PCR fingerprinting. The VL gene is spliced to the $C_L$ gene using PCR and cloned into the vector containing the $V_H$ CH1 gene.

III. Preparation of Chineric Molecules.

In another embodiment this invention provides for chimeric molecules comprising a C6 antibody attached to an effector molecule. As explained above, the effector molecule component of the chimeric molecules of this invention may be any molecule whose activity it is desired to deliver to cells that express c-erbB-2. Suitable effector molecules include cytotoxins such as PE, Ricin, Abrin or DT, radionuclides, ligands such as growth factors, antibodies, detectable labels such as fluorescent or radioactive labels, and therapeutic compositions such as liposomes and various drugs.

A) Cytotoxins.

Particularly preferred cytotoxins include Pseudomonas exotoxins, Diphtheria toxins, ricin, and abrin. Pseudomonas exotoxin and Dipthteria toxin, in particular, are frequently used in chimeric cytotoxins.

i) Pseudomonas exotoxin (PE).

Pseudomonas exotoxin A (PE) is an extremely active monomeric protein (molecular weight 66 kD), secreted by *Pseudomonas aeruginosa,* which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1–252) mediates cell binding. Domain II (amino acids 253–364) is responsible for translocation into the cytosol and domain III (amino acids 400–613) mediates ADP ribosylation of elongation factor 2, which inactivates the protein and causes cell death. The function of domain Ib (amino acids 365–399) remains undefined, although a large part of it, amino acids 365–380, can be deleted without loss of cytotoxicity. See Siegall et al., *J. Biol. Chem.* 264: 14256–14261 (1989).

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, REDLK (SEQ ID NO:26) (as in native PE), REDL (SEQ ID NO:27), RDEL (SEQ ID NO:28), or KDEL (SEQ ID NO:29), repeats of those, or other sequences that function to maintain or recycle proteins into the endoplasmic reticulum, referred to here as "endoplasmic retention sequences". See, for example, Chaudhary et al, *Proc. Natl. Acad. Sci. USA* 87:308–312 and Seetharam et al, *J. Biol. Chem.* 266: 17376–17381 (1991).

The targeting molecule can be inserted in replacement for domain Ia. A similar insertion has been accomplished in what is known as the TGFα-PE40 molecule (also referred to as TP40) described in Heimbrook et al., *Proc. Natl. Acad. Sci., USA,* 87: 4697–4701 (1990). See also, Debinski et al. *Bioconj. Chem.,* 5: 40 (1994) for other PE variants).

The PE molecules can be fused to the C6 antibody by recombinant means. The genes encoding protein chains may be cloned in cDNA or in genomic form by any cloning procedure known to those skilled in the art. See for example Sambrook et al., *Molecular Cloning: A Laboratory Manual,* Cold Spring Harbor Laboratory, (1989). Methods of cloning genes encoding PE fused to various ligands are well known to those of skill in the art. See, for example, Siegall et al., *FASEB J.,* 3: 2647–2652 (1989); Chaudhary et al. *Proc. Natl. Acad. Sci. USA,* 84: 4538–4542 (1987).

Those skilled in the art will realize that additional modifications, deletions, insertions and the like may be made to the chimeric molecules of the present invention or to the nucleic acid sequences encoding the C6 chimeric molecules. Especially, deletions or changes may be made in PE or in a linker connecting an antibody gene to PE, in order to increase cytotoxicity of the fusion protein toward target cells or to decrease nonspecific cytotoxicity toward cells without antigen for the antibody. All such constructions may be made by methods of genetic engineering well known to those skilled in the art (see, generally, Sambrook et al., supra) and may produce proteins that have differing properties of affinity, specificity, stability and toxicity that make them particularly suitable for various clinical or biological applications.

ii) Diphtheria toxin (DT).

Like PE, diphtheria toxin (DT) kills cells by ADP-ribosylating elongation factor 2 (EF-2) thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al., *Science,* 175: 901–903 (1972); Uchida et al. *J. Biol. Chem.,* 248: 3838–3844 (1973)).

The targeting molecule-Diphtheria toxin fusion proteins of this invention may have the native receptor-binding domain removed by truncation of the Diphtheria toxin B chain. DT388, a DT in which the carboxyl terminal sequence beginning at residue 389 is removed is illustrated in Chaudhary, et al., *Bioch. Biophys. Res. Comm.,* 180: 545–551 (1991).

Like the PE chimeric cytotoxins, the DT molecules may be chemically conjugated to the C6 antibody but, may also be prepared as fusion proteins by recombinant means. The genes encoding protein chains may be cloned in cDNA or in genomic form by any cloning procedure known to those skilled in the art. Methods of cloning genes encoding DT fused to various ligands are also well known to those of skill in the art. See, for example, Williams et al. *J. Biol. Chem.*

265: 11885–11889 (1990) which describes the expression of growth-factor-DT fusion proteins.

The term "Diphtheria toxin" (DT) as used herein refers to full length native DT or to a DT that has been modified. Modifications typically include removal of the targeting domain in the B chain and, more specifically, involve truncations of the carboxyl region of the B chain.

B) Detectable labels.

Detectable labels suitable for use as the effector molecule component of the chimeric molecules of this invention include any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, green fluorescent protein, and the like), radiolabels (e.g., $^3$H, $^{125}$I, $^{35}$S, $^{14}$C, or 32P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

C) Ligands.

As explained above, the effector molecule may also be a ligand or an antibody. Particularly preferred ligand and antibodies are those that bind to surface markers of immune cells. Chimeric molecules utilizing such antibodies as effector molecules act as bifunctional linkers establishing an association between the immune cells bearing binding partner for the ligand or antibody and the tumor cells expressing the c-erbB-2. Suitable antibodies and growth factors are known to those of skill in the art and include, but are not limited to, IL-2, IL-4, IL-6, IL-7, tumor necrosis factor (TNF), anti-Tac, TGFα, and the like.

D) Other therapeutic moieties.

Other suitable effector molecules include pharmacological agents or encapsulation systems containing various pharmacological agents. Thus, the C6 antibody may be attached directly to a drug that is to be delivered directly to the tumor. Such drugs are well known to those of sldll in the art and include, but are not limited to, doxirubicin, vinblastine, genistein, antisense molecules, ribozymes and the like.

Alternatively, the effector molecule may comprise an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735 and Connor et al., *Pharm. Ther.,* 28: 341–365 (1985).

E) Attachment of the c6 antibody to the effector molecule.

One of skill will appreciate that the C6 antibody and the effector molecule may be joined together in any order. Thus the effector molecule may be joined to either the amino or carboxy termini of the C6 antibody. The C6 antibody may also be joined to an internal region of the effector molecule, or conversely, the effector molecule may be joined to an internal location of the C6 antibody as long as the attachment does not interfere with the respective activities of the molecules.

The C6 antibody and the effector molecule may be attached by any of a number of means well known to those of skill in the art. Typically the effector molecule is conjugated, either directly or through a linker (spacer), to the C6 antibody. However, where the effector molecule is a polypeptide it is preferable to recombinantly express the chimeric molecule as a single-chain fusion protein.

i) Conjugation of the effector molecule to the targeting molecule.

In one embodiment, the targeting molecule C6 antibody is chemically conjugated to the effector molecule (e.g. a cytotoxin, a label, a ligand, or a drug or liposome). Means of chemically conjugating molecules are well known to those of skill (see, for example, Chapter 4 in *Monoclonal Antibodies: Principles and Applications,* Birch and Lennox, eds. John Wiley & Sons, Inc. N.Y. (1995) which describes conjugation of antibodies to anticancer drugs, labels including radio labels, enzymes, and the like).

The procedure for attaching an agent to an antibody or other polypeptide targeting molecule will vary according to the chemical structure of the agent. Polypeptides typically contain variety of functional groups; e.g., carboxylic acid (COOH) or free amine (—NH$_2$) groups, which are available for reaction with a suitable functional group on an effector molecule to bind the effector thereto.

Alternatively, the targeting molecule and/or effector molecule may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form the desired immunoconjugate. Alternatively, derivatization may involve chemical treatment of the targeting molecule, e.g., glycol cleavage of a sugar moiety attached to the protein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptide, such as antibodies or antibody fragments, are also known (See U.S. Pat. No. 4,659,839).

Many procedure and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. *Cancer Res.* 47: 4071–4075 (1987) which are incorporated herein by reference. In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine,* Academic Press, pp. 168–190 (1982), Waldmann, *Science,* 252: 1657 (1991), U.S. Pat. Nos. 4,545,985 and 4,894,443.

In some circumstances, it is desirable to free the effector molecule from the targeting molecule when the chimeric molecule has reached its target site. Therefore, chimeric conjugates comprising linkages which are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

ii) Production of fusion proteins.

Where the C6 antibody and/or the effector molecule are relatively short (i.e., less than about 50 amino acids) they may be synthesized using standard chemical peptide synthesis techniques. Where both molecules are relatively short the chimeric molecule may be synthesized as a single contiguous polypeptide. Alternatively the C6 antibody and the effector molecule may be synthesized separately and then fused by condensation of the amino terminus of one molecule with the carboxyl terminus of the other molecule thereby forming a peptide bond. Alternatively, the targeting and effector molecules may each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis; pp.* 3–284 in *The Peptides: Analysis, Synthesis, Biology. Vol.* 2: *Special Methods in Peptide Synthesis, Part A.,* Merrifield, et al. *J. Am. Chem. Soc.,* 85: 2149–2156 (1963), and Stewart et al., *Solid Phase Peptide Synthesis, 2nd ed.* Pierce Chem. Co., Rockford, Ill. (1984).

In a preferred embodiment, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins (e.g. C6.5Ab-PE) of this invention may be prepared by any suitable method, including, for example, cloning and restriction of appropriate sequences or direct chemical synthesis by methods such as the phosphotriester method of Narang et al. *Meth. Enzymol.* 68: 90–99 (1979); the phosphodiester method of Brown et al., *Meth. Enzmol.* 68: 109–151 (1979); the diethylphosphoramidite method of Beaucage et al., *Tetra. Lett.,* 22: 1859–1862 (1981); and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of sldll would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In a preferred embodiment, DNA encoding fusion proteins of the present invention may be cloned using DNA amplification methods such as polymerase chain reaction (PCR). Thus, for example, the gene for the C6 antibody may be amplified from a nucleic acid template (clone) using a sense primer containing a first restriction site and an antisense primer containing a second restriction site. This produces a nucleic acid encoding the mature C6 antibody sequence and having terminal restriction sites. A cytotoxin (or other polypeptide effector) may be cut out of a plasmid encoding that effector using restriction enzymes to produce cut ends suitable for annealing to the C6 antibody. Ligation of the sequences and introduction of the construct into a vector produces a vector encoding the C6-effector molecule fusion protein. Such PCR cloning methods are well known to those of skill in the art (see, for example, Debinski et al. *Int. J. Cancer,* 58: 744–748 (1994), for an example of the preparation of a PE fusion protein).

While the two molecules may be directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity. One of skill will appreciate that PCR primers may be selected to introduce an amino acid linker or spacer between the C6 antibody and the effector molecule if desired.

The nucleic acid sequences encoding the fusion proteins may be expressed in a variety of host cells, including E. coli, other bacterial hosts, yeast, and various higher eukaryotic cells such as the COS, CHO and HeLa cells lines and myeloma cell lines. The recombinant protein gene will be operably linked to appropriate expression control sequences for each host. For E. coil this includes a promoter such as the 17, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for E. coli and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes, *Protein Purification,* Springer-Verlag, N.Y. (1982), Deutscher, *Methods in Enzymology Vol.* 182: *Guide to Protein Purification.,* Academic Press, Inc. N.Y. (1990)). In a preferred embodiment, the fusion proteins are purified using affinity purification methods as described in Examples 1 and 2. Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the C6 antibody-effector fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art. (See, Debinski et al. *J. Biol. Chem.,* 268: 14065–14070 (1993); Kreitman and Pastan, *Bioconjug. Chem.,* 4: 581–585 (1993); and Buchner, et al., *Anal. Biochem.,* 205: 263–270 (1992). Debinski et al., for example, describe the denaturation and reduction of inclusion body proteins in guanidine-DTE. The protein is then refolded in a redox buffer containing oxidized glutathione and L-arginine.

One of skill would recognize that modifications can be made to the C6 antibody-effector fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

IV. Diagnostic Assays.

As explained above, the C6 antibodies may be used for the in vivo or in vitro detection of c-erbB-2 and thus, in the diagnosis and/or localization of cancers characterized by the expression of c-erbB-2.

A) In Vivo Detection of c-erbB-2.

The C6 antibodies and/or chimeric molecules of the present invention may be used for in vivo detection and localization of cells (e.g. c-erbB-2 positive carcinoma) bearing c-erbB-2. Such detection involves administering to an organism a chimeric molecule comprising a C6 joined to a label detectable in vivo. Such labels are well known to those of skill in the art and include, but are not limited to, electron dense labels such as gold or barium which may be detected by X-ray or CAT scan, various radioactive labels that may be detected using scintillography, and various magnetic and paramagnetic materials that may be detected using positron emission tomography (PET) and magnetic resonance imaging (MRI). The C6 antibody associates the label with the c-erbB-2 bearing cell which is then detected and localized using the appropriate detection method.

B) In Vitro Detection of c-erbB-2.

The C6 antibodies of this invention are also useful for the detection of c-erbB-2 in vitro e.g., in biological samples obtained from an organism. The detection and/or quantification of c-erbB-2 in such a sample is indicative the presence or absence or quantity of cells (e.g., tumor cells) overexpressing c-erbB-2.

The c-erbB-2 antigen may be quantified in a biological sample derived from a patient such as a cell, or a tissue sample derived from a patient. As used herein, a biological sample is a sample of biological tissue or fluid that contains a c-erbB-2 antigen concentration that may be correlated with and indicative of cells overexpressing c-erbB-2. Preferred biological samples include blood, urine, and tissue biopsies.

In a particularly preferred embodiment, erbB-2 is quantified in breast tissue cells derived from normal or malignant breast tissue samples. Although the sample is typically taken from a human patient, the assays can be used to detect erbB-2 in cells from mammals in general, such as dogs, cats, sheep, cattle and pigs, and most particularly primates such as humans, chimpanzees, gorillas, macaques, and baboons, and rodents such as mice, rats, and guinea pigs.

Tissue or fluid samples are isolated from a patient according to standard methods well known to those of skill in the art, most typically by biopsy or venipuncture. The sample is optionally pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

C) Assay Formats (Detection or Quantification of c-erbB2).

i) Immunological Binding Assays

The c-erbB-2 peptide (analyte) or an anti-c-erb-2 antibody is preferably detected in an immunoassay utilizing a C6 antibody as a capture agent that specifically binds to a c-erbB-2 peptide.

As used herein, an immunoassay is an assay that utilizes an antibody (e.g. a C6 antibody) to specifically bind an analyte (e.g., c-erb-2). The immunoassay is characterized by the use of specific binding to a C6 antibody as opposed to other physical or chemical properties to isolate, target, and quantify the c-erbB-2 analyte.

The c-erbB-2 marker may be detected and quantified using any of a number of well recognized immunological binding assays. (See for example, U.S. Pat. Nos. 4,366,241; 4,376,110; 4,517,288; and 4,837,168, which are hereby incorporated by reference.) For a review of the general immunoassays, see also *Methods in Cell Biology Volume 37: Antibodies in Cell Biology,* Asai, ed. Academic Press, Inc. New York (1993); *Basic and Clinical Immunology* 7th Edition, Stites & Terr, eds. (1991)).

The immunoassays of the present invention are performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology,* Elsevier Science Publishers B. V., Amsterdam; Harlow and Lane, supra; Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non isotopic Immunoassays* Plenum Press, NY.

Immunoassays often utilize a labeling agent to specifically bind to and label the binding complex formed by the capture agent and the analyte (i.e., a C6 antibody-erbB-2 complex). The labeling agent may itself be one of the moieties comprising the antibody/analyte complex. Thus, the labeling agent may be a labeled c-erbB-2 peptide or a labeled C6 antibody. Alternatively, the labeling agent is optionally a third moiety, such as another antibody, that specifically binds to the C6 antibody, the c-erbB-2 peptide, the anti-c-erbB-2 antibody/c-erbB-2 peptide complex, or to a modified capture group (e.g., biotin) which is covalently linked to c-erbB-2 or the C6 antibody.

In one embodiment, the labeling agent is an antibody that specifically binds to the C6 antibody. Such agents are well known to those of skill in the art, and most typically comprise labeled antibodies that specifically bind antibodies of the particular animal species from which the C6 antibody is derived (e.g., an anti-species antibody). Thus, for example, where the capture agent is a human derived C6 antibody, the label agent may be a mouse anti-human IgG, i.e., an antibody specific to the constant region of the human antibody.

Other proteins capable of specifically binding immunoglobulin constant regions, such as streptococcal protein A or protein G are also used as the labeling agent. These proteins are normal constituents of the cell walls of streptococcal bacteria. They exhibit a strong non immunogenic reactivity with immunoglobulin constant regions from a variety of species. See, generally Kronval, et al., (1973) *J. Immunol.,* 111: 1401–1406, and Akerstrom, et al., (1985) *J. Immunol.,* 135:2589–2542.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays are carried out at ambient temperature, although they can be conducted over a range of temperatures, such as 5° C. to 45° C.

(a) Non competitive assay fonnats.

Immunoassays for detecting c-erb-2 are typically either competitive or noncompetitive. Noncompetitive immunoassays are assays in which the amount of captured analyte (in this case, c-erb-2) is directly measured. In one preferred "sandwich" assay, for example, the capture agent (e.g., C6 antibody) is bound directly or indirectly to a solid substrate where it is immobilized. These immobilized C6 antibodies capture c-erb-2 present in a test sample (e.g., a biological sample derived from breast tumor tissue). The c-erb-2 thus immobilized is then bound by a labeling agent, such as a second c-erb-2 antibody bearing a label. Alternatively, the second antibody may lack a label, but it may, in turn, be bound by a labeled third antibody specific to antibodies of the species from which the second antibody is derived. Free labeled antibody is washed away and the remaining bound labeled antibody is detected (e.g., using a gamma detector where the label is radioactive). One of skill will appreciate that the analyte and capture agent is optionally reversed in the above assay, e.g., when the presence, quantity or avidity of a C6 antibody in a sample is to be measured by its binding to an immobilized c-erb-2 peptide.

(b) Competitive assay formats.

In competitive assays, the amount of analyte (e.g., c-erbB-2) present in the sample is measured indirectly by measuring the amount of an added (exogenous) analyte displaced (or competed away) from a capture agent (e.g., C6 antibody) by the analyte present in the sample. In one competitive assay, a known amount of c-erb-2 is added to a test sample with an unquantified amount of c-erbB-2, and the sample is contacted with a capture agent, e.g., a C6 antibody that specifically binds c-erb-2. The amount of added c-erbB-2 which binds to the C6 antibody is inversely proportional to the concentration of c-erbB-2 present in the test sample.

The C6 antibody can be immobilized on a solid substrate. The amount of erbB2 bound to the C6 antibody is determined either by measuring the amount of erbB-2 present in an erbB-2-C6 antibody complex, or alternatively by measuring the amount of remaining uncomplexed erbB-2. Similarly, in certain embodiments where the amount of erbB-2 in a sample is known, and the amount or avidity of a C6 antibody in a sample is to be determined, erbB-2 becomes the capture agent (e.g., is fixed to a solid substrate) and the C-6 antibody becomes the analyte.

(c) Reduction of Non Specific Binding.

One of skill will appreciate that it is often desirable to reduce non specific binding in immunoassays and during analyte purification. Where the assay involves c-erbB-2, C6 antibody, or other capture agent immobilized on a solid substrate, it is desirable to minimize the amount of non specific binding to the substrate. Means of reducing such non specific binding are well known to those of skill in the art. Typically, this involves coating the substrate with a proteinaceous composition. In particular, protein compositions such as bovine serum albumin (BSA), nonfat powdered milk, and gelatin are widely used.

(d) Substrates.

As mentioned above, depending upon the assay, various components, including the erbB-2, C6 or antibodies to erbB-2 or C6, are optionally bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glassess, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed, e.g., as laminates, to obtain various properties. For example, protein coatings, such as gelatin can be used to avoid non specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes,* Ichiro Chibata, Halsted Press, New York, 1978, and Cuatrecasas, *J. Biol. Chem.* 245 3059 (1970).

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

ii) Other Assay Formats

C-erbB-2 polypeptides or C6 antibodies and can also be detected and quantified by any of a number of other means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Western blot analysis and related methods can also be used to detect and quantify the presence of erbB-2 peptides and C6 antibodies in a sample. The technique generally comprises separating sample products by gel electrophoresis on the basis of molecular weight, transferring the separated products to a suitable solid support, (such as a nitrocellulose filter, a nylon filter, or derivatized nylon filter), and incubating the sample with the antibodies that specifically bind either the erbB-2 peptide or the anti-erbB-2 antibody. The antibodies specifically bind to the biological agent of interest on the solid support. These antibodies are directly labeled or alternatively are subsequently detected using labeled antibodies (e.g., labeled sheep anti-human antibodies where the antibody to a marker gene is a human antibody) which specifically bind to the antibody which binds either anti-erbB-2 or erbB-2 as appropriate.

Other assay formats include liposome immunoassays (LIAs), which use liposomes designed to bind specific molecules (e.g., antibodies) and release encapsulated reagents or markers. The released chemicals are then detected according to standard techniques (see, Monroe et al., (1986) *Amer. Clin. Prod. Rev.* 5:34–41).

iii) Labeling of C6 antibodies.

The labeling agent can be, e.g., a monoclonal antibody, a polyclonal antibody, a protein or complex such as those described herein, or a polymer such as an affinity matrix, carbohydrate or lipid. Detection proceeds by any known method, including immunoblotting, western analysis, gel-mobility shift assays, tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., LacZ, CAT, horse radish peroxidase, alkaline phosphatase and others, commonly used as detectable enzymes, either as marker gene products or in an ELISA), and colorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the Like. Similarly, enzymatic labels may be detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of C6 antibodies and C6 antibody-erbB-2 peptides. In this case, antigen-coated particles are agglutinated by samples comprising the target antibodies. In this format, none of the components need be labeled and the presence of the target antibody is detected by simple visual inspection.

V. Pharmaceutical Compositions.

The chimeric molecules of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a solution of the chimeric molecule dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The compositions containing the present fusion proteins or a cocktail thereof (i.e., with other proteins) can be administered for therapeutic treatments. In therapeutic applications, compositions are administered to a patient suffering from a disease, typically a c-erbB-2 positive carcinoma, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

Among various uses of the cytotoxic fusion proteins of the present invention are included a variety of disease conditions caused by specific human cells that may be eliminated by the toxic action of the protein. One application is the treatment of cancer, such as by the use of a C6 antibody attached to a cytotoxin.

Another approach involves using a ligand that binds a cell surface marker (receptor) so the chimeric associates cells bearing the ligand substrate are associated with the c-erbB-2 overexpressing tumor cell. The ligand portion of the molecule is chosen according to the intended use. Proteins on the membranes of T cells that may serve as targets for the ligand includes FcγI, FcγII and FcγIII, CD2 (T11), CD3, CD4 and CD8. Proteins found predominantly on B cells that might serve as targets include CD10 (CALLA antigen), CD19 and CD20. CD45 is a possible target that occurs broadly on lymphoid cells. These and other possible target lymphocyte target molecules for the chimeric molecules bearing a ligand effector are described in *Leukocyte Typing III*, A. J. McMichael, ed., Oxford University Press (1987). Those skilled in the art will realize ligand effectors may be chosen that bind to receptors expressed on still other types of cells as described above, for example, membrane glycoproteins or ligand or hormone receptors such as epidermal growth factor receptor and the like.

VI. Kits For Diagnosis or Treatment.

In another embodiment, this invention provides for kits for the treatment of tumors or for the detection of cells overexpressing c-erbB-2. Kits will typically comprise a chimeric molecule of the present invention (e.g. C6 antibody-label, C6 antibody-cytotoxin, C6 antibody-ligand, etc.). In addition the kits will typically include instructional materials disclosing means of use of chimeric molecule (e.g. as a cytotoxin, for detection of tumor cells, to augment an immune response, etc.). The kits may also include additional components to facilitate the particular application for which the kit is designed. Thus, for example, where a kit contains a chimeric molecule in which the effector molecule is a detectable label, the kit may additionally contain means of detecting the label (e.g. enzyme substrates for enzymatic labels, filter sets to detect fluorescent labels, appropriate secondary labels such as a sheep anti-human antibodies, or the like). The kits may additionally include buffers and other reagents routinely used for the practice of a particular method. Such kits and appropriate contents are well known to those of skill in the art.

EXAMPLES

The following examples are provided by way of illustration only and not by way of limitation. Those of skill will readily recognize a variety of noncritical parameters which could be changed or modified to yield essentially similar results.

Example 1

Isolation and Characterization of Human Single-chain Fvs Binding C-erbb-2 Materials and Methods:

Preparation of c-erbB-2 ECD

The antigen c-erbB-2 ECD with a Ser-Gly-His$_6$ C-terminal fusion was expressed from Chinese Hamster Ovary cells and purified by immobilized metal affinity chromatography (IMAC).

Phage preparation

Phage were prepared from a phagemid library ($3 \times 10^7$ members) expressing sFv as pIII fusions on the phage surface (Marks et al. (1991) *J. Mol. Biol.* 222:581–597). The library was created from a repertoire of sFv genes consisting of human heavy and light chain variable region ($V_H$ and $V_L$) genes isolated from the peripheral blood lymphocytes of unimmunized human volunteers. To rescue phagemid particles from the library, 50 ml of 2×TY media containing 100 μg/ml ampicillin and 1% glucose were inoculated with $10^8$ bacteria taken from the frozen library glycerol stock. The culture was grown at 37° C. with shaking to an $A_{600}$ nm of 0.8, $7.0 \times 10^{11}$ colony forming units of VCS-MI3 (Stratgene) added, and incubation continued at 37° C. for 1 h without shaldng followed by 1 h with shaking. The cells were pelleted by centrifugation at 4500g for 10 min, resuspended in 200 ml of 2×TY media containing 100 μg/ml ampicillin and 2.5 μg/ml kanamycin and grown overnight at 37° C. Phage particles were purified and concentrated by 2 polyethylene glycol precipitations and resuspended in PBS (25 mM NaH$_2$PO$_4$, 125 mM NaCl, pH 7.0) to approximately $10^{13}$ transducing units/ml ampicillin resistant clones.

Selection of binding phage antibodies

Phage expressing sFv which bound c-erbB-2 were selected by panning the phage library on immobilized c-erbB-2 ECD (Marks et al. (1991) supra.). Briefly, immunotubes (Nunc, Maxisorb) were coated with 2 ml (100 μg/ml) c-erbB-2 ECD in PBS overnight at 20° C. and blocked with 2% milk powder in PBS for 2 h at 37° C. 1 ml of the phage solution (approximately $10^{13}$ phage) was added to the tubes and incubated at 20° C. with tumbling on an over and under turntable for 2 h. Nonbinding phage were eliminated by sequential washing (15 times with PBS containing 0.05% Tween followed by 15 times with PBS). Binding phage were then eluted from the immunotubes by adding 1 ml of 100 mM triethylamine, incubating for 10 min at 20° C., transferring the solution to a new tube, and neutralizing with 0.5 ml 1M Tris HCl, PH 7.4. Half of the eluted phage solution was used to infect 10 ml of *E.coli* TG1 (Gibson, T.J. (1984) Studies on the Epstein-Barr virus genome, Cambridge University Ph.D. thesis; Carter et aL (1985) *Nucleic Acids Res.*, 13: 4431–4443) grown to an $A_{600}$ nm of 0.8–0.9. After incubation for 30 min at 37° C., bacteria were plated on TYE plates containing 100 μg/ml ampicillin and 1 % glucose and grown overnight at 37° C. Phage were rescued and concentrated as described above and used for the next selection round. The selection process was repeated for a total of 5 rounds.

Screening for binders

After each round of selection, 10 ml of *E.coli* HB2151 (Carter et al. (1985) *Nucleic Adds Res.*, 13: 4431–43) ($A_{600}$ run~0.8) were infected with 100 μl of the phage eluate in order to prepare soluble sFv. In this strain, the amber codon between the sFv gene and gene III is read as a stop codon and native soluble sFv secreted into the periplasm and media (Hoogenboom et al. (1991) *Nucleic Acids Res.* 19: 4133–4137). Single ampicillin resistant colonies were used to inoculate microtitre plate wells containing 150 μl of 2×TY containing 100 μg/ml ampicillin and 0.1% glucose. The bacteria were grown to an $A_{600}$ nm~1.0, and sFv expression induced by the addition of IPTG to a final concentration of 1 mM (De Bellis et al., (1990) *Nucleic Acids Res.,* 18:1311). Bacteria were grown overnight at 30° C., the cells removed by centrifugation, and the supernatant containing sFv used directly.

To screen for binding, 96-well microtiter plates (Falcon 3912) were coated overnight at 4° C. with 10 μg/ml c-erbB-2 ECD in PBS, blocked for 2 h at 37° C. with 2% milk powder in PBS, and incubated for 1.5 hours at 20° C. with 50 μl of the *E. coli* supernatant containing sFv. Binding of soluble sFv to antigen was detected with a mouse monoclonal antibody (9E1O) which recognizes the C-terminal myc peptide tag (Munro, S. et al., (1986) Cell, 46:291–300) and peroxidase conjugated anti-mouse Fc antibody (Sigma) using ABTS as substrate (Ward et al. (1989) *Nature,* 341: 544–546). The reaction was stopped after 30 min with NaF (3.2 mg/ml) and the $A_{405}$ nm measured. Unique clones were identified by PCR fingerprinting (Marks, J. D. et al., (1991) J. Mol. Biol., 222:581–597) and DNA sequencing. The specificity of each unique sFv was determined by ELISA performed as described above with wells coated with 10 μg/ml of bovine serum albumin, hen egg white lysozyme, bovine glutamyltranspeptidase, c-erbB-2 ECD, VCS M13 ($3.5 \times 10^{12}$/ml) and casein (0.5%). For ELISA with biotinylated c-erbB-2 ECD, microtiter plates (Immunolon 4, Dynatech) were coated with 50 μl immunopure avidin (Pierce; 10 μg/ml in PBS) overnight at 4° C., blocked with 1% bovine serum albumin in PBS for 1 h at 37° C. and incubated with 50 μl biotinylated c-erbB-2 extracellular domain (5 μg/ml) for 30 min at 20° C. To prepare biotinylated antigen, 0.2 ml c-erbB-2 ECD (1 mg/ml in PBS) was incubated with 0.5 mM NHS-LC-biotin (Pierce) overnight at 4° C. and then purified on a presto desalting column (Pierce).

Subcloning, expression and purification.

To facilitate purification, the C6.5 sFv gene was subcloned into the expression vector pUC119Sfi/NotHismyc (Griffiths, et al. (1994) *EMBO J.,* 13: 3245–3260) which results in the addition of a hexa-histidine tag at the C-terminal end of the sFv. Briefly, pHEN-1 vector DNA containing the C6.5 sFv DNA was prepared by alline lysis milliprep, digested with NcoI and NotI, and the sFv DNA purified on a 1.5% agarose gel. C6.5 sFv DNA was ligated into pUC119Sfil/NotIHismyc digested with NcoI and NotI and the legation mixture used to transform electrocompetent *E. coli* HB2151. For expression, 200 ml of 2×TY media containing 100 μg/ml ampicillin and 0.1% glucose was inoculated with *E. coli* HB2151 harboring the C6.5 gene in pUC119Sfil/NotIHismyc. The culture was grown at 37° C. to an $A_{600}$ nm of 0.8, soluble sFv expression induced by the addition of IPTG to a final concentration of 1 mM, and the culture grown at 30° C. in a shaker flask overnight. Single-chain Fv was harvested from the periplasm using the following protocol. Cells were harvested by centrifugation at 4000 g for 15 min, resuspended in 10 ml of ice cold 30 mM Tris-HCl pH 8.0, 1 mM EDTA, 20% sucrose, and incubated on ice for 20 min. The bacteria were pelleted by centrifugation at 6000 g for 15 min. and the "periplasmic fraction" cleared by centrifugation at 30,000 g for 20 min. The supernatant was dialyzed overnight at 4° C. against 8 L of IMAC loading buffer (30 mM sodium phosphate pH 7.5, 500 mM NaCl, 20 mM imidazole) and then filtered through a 0.2 micron filter.

The sFv was purified by IMAC. All steps were performed at 4° C. on a Perceptive Biosystems BIOCAD Sprint. A column containing 2 ml of Ni-NTA resin (Qiagen) was washed with 20 ml IMAC column wash buffer (50 mM sodium phosphate pH 7.5, 500 mM NaCl, 2.50 mM imidazole) and 20 ml of IMAC loading buffer. The periplasmic preparation was loaded onto the column by pump and the column washed sequentially with 50 ml IMAC loading buffer and 50 ml IMAC washing buffer (50 mM sodium phosphate pH 7.5, 500 mM NaCl, 23 mM imidazole). Protein was eluted with 2.5 ml IMAC elution buffer (50 mM sodium phosphate pH 7.5, 300 mM NaCl, 100 mM imidazole) and 4 ml fractions collected. Protein was detected by absorbance at 280 nm and sFv typically eluted between fractions 6 and 8. To remove dimeric and aggregated sFv, samples were concentrated to a volume <1 ml in a Centricon 10 (Amicon) and fractionated on a Superdex 75 column using a running buffer of HBS (10 mM Hepes, 150 mM NaCl, pH 7.4). The purity of the final preparation was evaluated by assaying an aliquot by SDS-PGE. Protein bands were detected by Coomassie staining. The concentration was determined spectrophotometrically, assuming an $A_{280}$ run of 1.0 corresponds to an sFv concentration of 0.7 mg/ml.

Affinity and kinetic measurements

The $K_d$ of C6.5 and 74IF8 sFv were determined using surface plasmon resonance in a BIAcore (Pharmacia) and by Scatchard analysis. In a BlAcore flow cell, 1400 resonance units (RU) of c-erbB-2 ECD (25 μg/ml in 10 mM sodium acetate, pH 4.5) was coupled to a CM5 sensor chip (Johnsson, B. et al., (1991) Anal. Biochem., 198:268–277). Association and dissociation of C6.5 and 741F8 sFv (100 nM–600 nM) were measured under continuous flow of 5 μl/min. Rate constant $k_{on}$ was determined from a plot of (1 n (dR/dt))/t vs concentration (Karlsson et al. (1991) *J. Immunol. Meth.,* 145: 229–240). Rate constant $k_{off}$ was determined from the dissociation part of the sensorgram at the highest concentration of sFv analyzed (Johnsson et al. (1991) *Anal. Biochem.,* 198: 268–277). The $K_d$ of C6.5 was also determined by Scatchard analysis (Scatchard (1949) *Annal. N.Y. Acad. Sci.,* 51: 660). All assays were performed in triplicate. Briefly, 50 μg of radioiodinated sFv was added to $5 \times 10^6$ SK-OV-3 cells in the presence of increasing concentrations of unlabeled sFv from the same preparation. After a 30 minute incubation at 20° C., the samples were washed with PBS at 40° C. and centrifuged at 500 g. The amount of labeled sFv bound to the cells was determined by counting the pellets in a gamma counter and the $K_a$ and $K_d$ were calculated using the EBDA program (V 2.0, G. A. McPherson, 1983).

Radiolabeling

The C6.5 sFv was labeled with radioiodine using the CT method (DeNardo et al. (1986) *Nud. Med. Biol.,* 13: 303–310). Briefly, 1.0 mg of protein was combined with $^{125}$I (14–17 mCi/mg) (Amersham, Arlington Heights, Ill.), or $^{131}$I (9.25 mCi/mg) (DuPont NEN, Wilmington, Del.) at an iodine to protein ratio of 1:10. 10 μg of CT (Sigma, St. Louis, Mo.) was added per 100 μg of protein and the resulting mixture was incubated for three minutes at room temperature. The reaction was quenched by the addition of 10 μg of sodium metabisulfite (Sigma) per 100 μg of protein. Unincorporated radioiodine was separated from the labeled protein by gel filtration using the G-50-80 centrifuged-column method (Adams et al. (1993) Cancer Res. 53: 4026–4034). The final specific activity of the CT labelling was 1.4 mCi/mg for the $^{131}$I-C6.5 sFv and typically about 1.0 mCi/mg for the $^{125}$I-C6.5 sFv.

Quality Control

The quality of the radiopharmaceuticals was evaluated by HPLC, SDS-PAGE, and a live cell binding assay as previously described (Adams et al. (1993) Cancer Res. 53: 4026–4034). The HPLC elution profiles from a Spherogel TSK-3000 molecular sieving column consistently demonstrated that greater than 99% of the radioactivity was associated with the protein peak. Greater than 98% of the nonreduced $^{125}$I-C6.5 sFv preparations migrated on SDS-PAGE as approximately 26 $D_d$ proteins while the remaining activity migrated as a dimer. The immunoreactivity of the radiopharmaceuticals was determined in a live cell binding assay utilizing c-erbB-2 overexpressing SK-OV-3 cells (#HTB 77; American Type Culture Collection, Rockville, Md.) and c-erbB-2 negative CEM cells (#119; American Type Culture Collection) (Adams, G. P. et al., (1993) Cancer Res. 53:4026–4034). Live cell binding assays revealed 49% of the activity associated with the positive cell pelleted less than 3% bound to the negative control cells; these results were lower than those typically seen with 741F8 sFv (60–80% bound) (Adams et al., (1993) supra.).

Cell Surface Dissociation Studies

Cell surface retention of biotinylated forms of the sFv molecules were measured by incubating 2 μg of either sFv with 2×10$^6$ SK-BR-3 cells (#HTB 30; American Type Culture Collection) in triplicate in 20 ml of FACS buffer, with 0.01% azide for 15 min at 4° C. The cells were washed twice with FACS buffer (4° C.) and resuspended in 2 ml of FACS buffer. 0.5 ml of the cell suspension were removed and placed in three separate tubes for incubations under differing conditions; 0 min at 4° C., 15 min at 37° C., and 30 min at 37° C. After the incubations, the cells were centrifuged at 300 g, the supernatants were removed, the cell pellets were washed 2× (4° C.) and the degree of retention of sFv on the cell surface at 37° C. (for 15 or 30 min) was compared to retention at 0 min at 4° C.

Biodistribution and Radioimmunoimaging Studies

Four to six week old C.BI71Icr-scid mice were obtained from the Fox Chase Cancer Center Laboratory Animal Facility. 2.5×10$^6$ SK-OV-3 cells in log phase were implanted s.c. on the abdomens of the mice. After about 7 weeks the tumors had achieved sizes of 100–200 mg and Lugol's solution was placed in the drinking water to block thyroid accumulation of radioiodine. Three days later, biodistribution studies were initiated. $^{125}$I-C6.5 sFv was diluted in PBS to a concentration of 0.2 mg/ml and each mouse was given 100 μL, containing 20 μg of radiopharmaceutical, by tail vein injection. Total injected doses were determined by counting each animal on a Series 30 multichannel analyzer/probe system (probe model #2007, Canaberra, Meridian, Conn.). Blood samples and whole body counts of the mice were obtained at regular intervals. Groups of 8 mice were sacrificed at 24 h after injection and the tumors and organs removed, weighed and counted in a gamma counter to determine the % ID/g (Adams et al. (1993) supra.; Adams et al. (1992) Antibody Inmmunoconj. and Radiopharm., 5: 81–95). The mean and standard error of the mean (SEM) for each group of data were calculated, and T:O ratios determined. Significance levels were determined using Students t-test.

For the radioimmunoimaging studies, tumor-bearing scid mice were injected with 100 μg (100 μl) of $^{131}$I-C6.5. At 24 hours after injection, the mice were euthanized by asphyxiation with CO$_2$ and images were acquired on a Prism 2000XP gamma camera (Picker, Highland Heights, Ohio 44142). Preset acquisitions of 100 k counts were used.

TABLE 6

Deduced Amino Acid Sequence of C4.1 and C6.5 Heavy and Light Chain. Sequences are aligned to the most homologous human germline gene. Dashes indicate sequence indentity, GL = germline sequence. DP58 and DP73 (ref. 22), IGLV3S1 (ref. 23), HUMLV122 and DPL 5.

SEQ ID Nos.

Heavy Chains

|  | Framework 1 | CDR1 | Framework 2 | CDR2 |  |
|---|---|---|---|---|---|
| C4.1 | QVQLVESGGGLVQPGGSLRLSCAASGFTFS | SYEMN | WVRQAPGKGLEWVS | YISSSGSTIYYADSVKG | Seq ID 30 |
| DP58 | E----------------------------- | ---- | -------------- | ----------------- | Seq ID 31 |
| C6.5 | QVQLLQSGAELKKPGESLKISCKGSGYSFT | SYWIA | WVRQMPGKGLEYMG | LIYPGDSDTKYSPSFQG | Seq ID 32 |
| DP73 | E---V-----V------------------- | ----G | -----------W-- | I--------R------- | Seq ID 33 |

|  | Framework 3 | CDR3 | Framework 4 |  |
|---|---|---|---|---|
| C4.1 | RFTISRDNAKNSLYLQMNSLRAEDTAVYYCAR | DLGGYSYGYVGLDY | WGQGTLVTVSS | Seq ID 30 |
| DP58 | ------------------------------- |  |  | Seq ID 31 |
| C6.5 | QVTISVDKSVSTAYLQWSSLKPSDSAVYFCAR | HDVGYCSSSNCAKWPEYFQH | WGQGTLVTVSS | Seq ID 32 |

TABLE 6-continued

Deduced Amino Acid Sequence of C4.1 and C6.5 Heavy and Light Chain. Sequences are aligned to the most homologous human germline gene. Dashes indicate sequence indentity, GL = germline sequence. DP58 and DP73 (ref. 22), IGLV3S1 (ref. 23), HUMLV122 and DPL 5.

|  |  | SEQ ID Nos. |
|---|---|---|
| DB73 | -----A---I-----------A--T-M-Y--- | Seq ID 33 |

Light Chains

|  | Framework 1 | CDR1 | Framework 2 | CDR2 |  |
|---|---|---|---|---|---|
| C4.1 | SELTQDPAVSVALGTVRITC | QGDSLRSYYAS | WYQQKPGQAPVLVIY | GKNNRPS | Seq ID 34 |
| IGLV3S1 | -S------------------ | ----------- | --------------- | ------- | Seq ID 35 |
| C6.5 | QSVLTQPPSVSAAPGQKVTISC | SGSSSNIGNNYVS | WYQQLPGTAPKLLIY | GHTNRPA | Seq ID 36 |
| HUMLV122 | ---------------------- | ------------- | --------------- | DNKK--S | Seq ID 37 |
| DPL5 | ---------A-GT---R----- | --------S---Y | --------------- | RNNQ--S | Seq ID 38 |

|  | Framework 3 | CDR3 | Framework 4 |  |
|---|---|---|---|---|
| C4.1 | GIPDRFSGSSSGNIASLTITGAQAEDEADYYC | NSRDSSGNPYWV | FGGGTKVTVLG | Seq ID 34 |
| IGLV3S1 | --------------T------------------ | --------H V- |  | Seq ID 35 |
| C6.5 | GVPDRFSGSKSGTSASLAISGFRSEDEADYYC | AAWDDSLSG WV | FGGGTKLTVLG | Seq ID 36 |
| humlv122 | -I--------------T-G-T-LQTG------- | GT--S---A |  | Seq ID 37 |
| dp15 | ---------------------L---------- | --------- |  | Seq ID 38 |

Results

After four rounds of selection, 9/190 clones analyzed by ELISA expressed sFv which bound c-erbB-2 ECD (ELISA signals greater than 0.4, 6 times higher than background). After five rounds of selection, 33/190 clones expressed c-erbB-2 binding sFv. PCR fingerprinting of the 42 positive clones identified two unique restriction patterns and DNA sequencing of 6 clones from each pattern revealed two unique human sFv sequences, C4. 1 and C6.5 (Table 6). The $V_H$ gene of C6.5 is from the human $V_H5$ gene family, and the $V_L$ gene from the human $V_\lambda$ family (Table 6). The $V_L$ gene appears to be derived from two different germline genes (HUMLV122 and DPL 5) suggesting the occurrence of PCR crossover (Table 6). The VH gene of C4. 1 is from the human $V_H3$ family, and the $V_L$ gene from the human $V_\lambda3$ family (Table 6). C4. 1 and C6.5 both bound c-erbB-2 specifically, as determined by ELISA against the relevant antigen and a panel of irrelevant antigens. However, when biotinylated c-erbB-2 ECD was bound to avidin coated plates and used in ELISA assays, the signal obtained with C6.5 was 6 times higher than observed when c-erbB-2 ECD was absorbed to polystyrene (1.5 vs 0.25). In contrast, C4.1 was not capable of binding to biotinylated c-erbB-2 ECD captured on avidin microtitre plates. Additionally, biotinylated and iodinated C6.5, but not C4.1, bound SK-BR-3 cells overexpressing c-erbB-2. These results indicate that C6.5 binds the native c-erbB-2 expressed on cells, but C4 binds a denatured epitope that appears when the antigen is adsorbed to polystyrene.

C6.5 was purified in yields of 10 mg/L of E. coli grown in shake flasks and gel filtration analysis indicated a single peak of approximately 27 $K_d$. The $K_d$ of purified C6.3 was determined using both surface plasmon resonance in a BIAcore and by Scatchard. The $K_d$ determined by BIAcore ($1.6 \times 10^{-8}$ M) agreed closely to the value determined by Scatchard ($2.0 \times 10^{-8}$ M) (Table 7). Kinetic analysis by BIAcore indicated that C6.5 had a rapid on-rate ($k_{on}$ $4.0 \times 10^5 M^{-1}s^{-1}$) and a rapid off-rate ($k_{off}$ $6.3 \times 10^{-3} s^{-1}$) (Table 2). Cell retention assay confirmed that C6.5 dissociated rapidly from the cell surface (Table 2).

After injection of $^{125}$I-C6.5 into scid mice bearing SK-OV-3 tumors, 1.47% ID/gm of tumor was retained after 24 hours (Table 7). Tumor:normal organ values ranged from 8.9 (tumor:kidney) to 283 (tumor:muscle). These values were higher than values observed for 741F8 sFv, produced from a murine monoclonal antibody ($K_d$=$2.6 \times 10^{-8}$ M. The high T:O ratios resulted in the highly specific visualization of the tumor by gamma scintigraphy using $^{131}$I-labelled C6.5.

TABLE 7

Characterization of anti-cerbB-2 sFv species. Characteristics of the murine anti-c-erbB-2 sFv, 741F8, and the human sFv C6.5 are compared. The affinity and dissociation constants were determined by Scatchard plot analysis, unless otherwise stated. Dissociation from c-erbB-2 positive (SK-OV-3) cells was measured in an in vitro live cell assay. The percentage of injected dose per gram (% ID/g) tumor M and tumor to organ ratios were determined in biodistribution studies performed in separate groups of scid mice (n = 10–14) bearing SK-OV-3 tumors overexpressing c-erbB-2. SEM are <35% of the associated values a = significantly unproved (p < 0.05) compared to 741F8 sFv.

| Parameter | 741F8 | C6.5 |
|---|---|---|
| $K_d$ (BIAcore) | $2.6 \times 10^{-8}$ M | $1.6 \times 10^{-8}$ M |
| $K_d$ (Scatchard) | $5.4 \times 10^{-8}$ M | $2.1 \times 10^{-8}$ M |

TABLE 7-continued

Characterization of anti-cerbB-2 sFv species. Characteristics of the murine anti-c-erbB-2 sFv, 741F8, and the human sFv C6.5 are compared. The affinity and dissociation constants were determined by Scatchard plot analysis, unless otherwise stated. Dissociation from c-erbB-2 positive (SK-OV-3) cells was measured in an in vitro live cell assay. The percentage of injected dose per gram (% ID/g) tumor M and tumor to organ ratios were determined in biodistribution studies performed in separate groups of scid mice (n = 10–14) bearing SK-OV-3 tumors overexpressing c-erbB-2. SEM are <35% of the associated values a = significantly unproved (p < 0.05) compared to 741F8 sFv.

| Parameter | 741F8 | C6.5 |
| --- | --- | --- |
| $k_{on}$ (BIAcore) | $2.4 \times 10^5$ M$^{-1}$s$^{-1}$ | $4.0 \times 10^5$ M$^{-1}$s$^{-1}$ |
| $k_{off}$ (BIAcore) | $6.4 \times 10^{-3}$s$^{-1}$ | $6.3 \times 10^{-3}$s$^{-1}$ |
| % associated with cell surface at 15 min | 32.7% | 60.6% |
| % associated with cell surface at 15 min | 8.6% | 22.2% |
| % ID/g Tumor | 0.8 | 1.0 |
| T:Blood | 14.7 | 22.9 |
| T:Kidney | 2.8 | 5.6a |
| T:Liver | 14.2 | 22.3 |
| T:Spleen | 10.3 | 34.1 |
| T:Intestine | 25.0 | 29.7 |
| T:Lung | 9.4 | 15.8 |
| T:Stomach | 8.9 | 11.1 |
| T:Muscle | 78.8 | 158.7 |
| T:Bone | 30.0 | 102.7 |

Example 2

Isolation of High Affinity Monomeric Human Anti-cerb-2 Single Chain Fv Using Affinity Driven Selection Materials and Methods Construction of heavy chain shuffled libraries To facilitate heavy chain shuffling, libraries were constructed in pHEN-1 (Hoogenboom et al. (1991) Nucleic Acids Res. 19, 4133–4137) containing human $V_H$ gene repertoires (FR1 to FR3) and a cloning site at the end of $V_H$ FR3 for inserting the $V_H$ CDR3, $V_H$ FR4, linker DNA and light chain from binding sFv as a BssHII-NotI fragment. To create the libraries three $V_H$ gene repertoires enriched for human $V_H1$, $V_H3$, and $V_H5$ gene were amplified by PCR using as a template single stranded DNA prepared from a $1.8 \times 10^8$ member sFv phage antibody library pHEN-1 (Marks et al. (1991) *J. Mol. Biol.* 222: 581–597). For PCR, 50 µl reactions were prepared containing 10 ng template, 25 pmol back primer (LMB3), 25 pmol forward primer (PV$_H$1FOR1, PV$_H$3FOR1, or PV$_H$5FOR1), 250 uM-dNTPs, 1 mM MgCl$_2$, and 0.5 µl (2 units) Taq DNA polymerase (Promega) in the manufacturer's buffer. Primers PV$_H$1For1, PV$_H$3For1, and PV$_H$5For1 were designed to anneal to the consensus $V_H1$, $V_H3$, or, $V_H5$ 3' FR3 sequence respectively (Tomlinson et al. (1992) *J. Mol. Biol.* 227, 776–798; see Table 18). The reaction mixture was subjected to 25 cycles of amplification (94° C. for 30 sec, 55° C. for 30 sec and 72° C. for 30 sec) using a Hybaid OmniGene cycler. The products were gel purified, isolated from the gel using DEAE membranes, eluted from the membranes with high salt buffer, ethanol precipitated, and resuspended in 20 µl of water (Sambrook et al. (1990)).

The DNA fragments from the first PCR were used as templates for a second PCR to introduce a BssHII site at the 3'-end of FR3 followed by a NotI site. The BssHII site corresponds to amino acid residue 93 and 94 (Kabat numbering (Kabat et al (1987) *Sequences of proteins of inununological interest*, 4th ed., US Department of Health and Human Services, Public Health Service, Bethesda, Md.; see, Table 5 in this reference) does not change the amino acid sequence (alanine-arginine). PCR was performed as described above using 200 ng purified first PCR product as template and the back primers PV$_H$1For2, PV$_H$3For2, and PV$_H$5For2. The PCR products were purified by extraction with phenol/chloroform, precipitated with ethanol, resuspended in 50 µl water and 5 µg digested with NotI and NcoI. The digested fragments were gel purified and each $V_H$ gene repertoire ligated separately into pHEN-1 (Hoogenboom et al. 1991 supra.) digested with Noti and NcoI. The ligation mix was purified by extraction with phenol/chloroform, ethanol precipitated, resuspended in 20 µl water, and 2.5 µl samples electroporated (Dower et al. (1988) *Nucleic Acids Res.* 16, 6127–6145) into 50 µl *E. coli* TG1 (Gibson et al (1984) Ph.D. Thesis, University of Cambridge). Cells were grown in 1 ml SOC (Sambrook et al. 1990) for 3 min and then plated on TYE (Miller (1972) *Experiments in Molecular Genetics* Cold Springs Harbor Lab Press, Cold Springs Harbor, N.Y.) media containing 100 µg ampicillin/ml and 1% (w/v) glucose (TYE-AMP-GLU). Colonies were scraped off the plates into 5 ml of 2×TY broth (Miller (1972), supra) containing 100 µg ampicillin/ml, 1% glucose (2×TY-AMP-GLU) and 15 (v/v) glycerol for storage at −70° C. The cloning efficiency and diversity of the libraries were determined by PCR screening (Gussow and Clackson (1989) *Nucleic Acids Res.* 17, 4000) as described (Marks et al. (1991), supra). The resulting phage libraries were termed pHEN-1-V$_H$1rep, pHEN-1-V$_H$3rep and pHEN-1-V$_H$5rep.

Three separate C6.5 heavy chain shuffled phage antibody libraries were made from the pHEN-1-V$_H$1rep, pHEN-1-V$_H$3rep, and pHEN-1-V$_H$5rep phage libraries. The C6.5 light chain gene, linker DNA, and V$_H$ CDR and FR4 were amplified by PCR from pHEN-1-C6.5 plasmid DNA using the primers PC6VL1Back and fdSEQ1. The PCR reaction mixtures were digested with BssHII and NotI and ligated intpHEN-1-V$_H$1rep, pHEN-1-V$_H$3rep, and pHEN-1-V$_H$5rep digested with NotI and BssHII. Transformation and creation of library stocks was as described above.

Construction of light chain shuffled libraries

To facilitate light chain shuffling, a library was constructed in PHEN-1 containing human $V_k$ and $V_\lambda$ gene repertoires, linker DNA, and cloning sites for inserting a $V_H$ gene as an NcoI-XhoI fragment. An XhoI can be encoded at the end of FR4 without changing the amino acid sequence of residues 102 and 103 (serine-serine) (Kabat et al. *Sequences of proteins of immunological interest*, 4th ed. U.S. Dept. Health and Human Services, Public Health Services, Bethesda, Md. (1987)). To create the library, a $V_k$ and $V_\lambda$ gene repertoire was amplified by PCR from a $1.8 \times 10^8$ member sFv phage antibody library in pHEN-1 (Marks et al. (1991), supra). PCR was performed as described above using 10 ng template, 25 pmol Back primer (RJH1/2/6Xho, RJH3Xho, oRJH4/5Xho) and 25 pmol forward primer (fdSEQ1). The back primers were designed to anneal to the first 6 nucleotides of the (Gly$_4$Ser) (SEQ ID NO:25) linker and either the J$_H$1, 2, 6, J$_H$3, or J$_H$4,5 segments respectively. The PCR reaction mixture was purified as described above, digested with XhoI and NotI, gel purified and ligated into pHEN-V$_\lambda$3S1 (Hoogenboom and Winter (1992) *J. Mol. Biol.* 227, 381–388) digested with XhoI and NotI. Transformation of *E. coli,* TG1, PCR screening, and creation of library stocks was as described above. The resulting phage library was termed pHEN-1-V$_L$rep.

The light chain shuffled phage antibody library was made for pHEN-1-V$_L$rep. The C6.5 V$_H$ gene was amplified by PCR from pHEN-1-C6.5 plasmid DNA using the primers PC6V$_H$1For and LMB3. The PCR reaction mixture was purified, digested with XhoI and NcoI, gel purified and ligated into pHEN-1-V$_L$rep digested with Xho and NcoI. Transformation of *E. coli* TG1, PCR screening, and creation of library stocks was as described above.

Construction of sFv containing highest affinity V$_H$ and V$_L$ gene obtained by chain shuffling Two new sFv were made by combining the V$_L$ gene of the highest affinity light chain shuffled sFv (C6L1) with the V$_H$ gene of the highest affinity heavy chain shuffled sFv (C6H1 or C6H2). The C6L1 plasmid was digested with NcoI and XhoI to remove the C6.5 V$_H$ gene and gel purified. The VH gene of C6H1 or C6H2 was amplified by PCR using the primers LMB3 and PC6V$_H$1For, digested with NcoI and XhoI and ligated into the previously digested C6L1 vector. Clones were screened for the presence of the correct insert by PCR fingerprinting and confirmed by DNA sequencing.

Preparation of phage

To rescue phagemid particles from the libraries, 10 ml of 2 TY-AMP-GLU were inoculated with an appropriate volume of bacteria (approximately 50 to 100 µl) from the library stocks to give an A$_{600}$ of 0.3 to 0.5 and grown for 30 min, shaking at 37° C. About 1×10$^{12}$ plaque-forming units of VCS-M13 (Stratagene) particles were added and the mixture incubated at 37° C. for 30 min without shaking followed by incubation at 37° C. for 30 min with shaking. Cells were spun down, resuspended in 50 ml 2×TY broth containing 100 µg ampicillin/ml and 50 µg kanamycin/ml (2×TY-AMP-KAN), and grown overnight, shaking at 25° C. Phage particles were purified and concentrated by two PEG-precipitations (Sambrook et al., 1990), resuspended in 5 ml phosphate buffered saline (25 mM NaH$_2$PO$_4$, 125 mM NaCl, pH 7.0, PBS) and filtered through a 0.45 u filter. The phage preparation consistently resulted in a titre of approximately 1013 transducing units/ml ampicillin-resistant clones.

Selection of phage antibody libraries

The light chain shuffled library was selected using immunotubes (Nunc; Maxisorb) coated with 2 ml c-erbB-2 ECD (25 µg/ml) in PBS overnight at room temperature (Marks et al. (1991) supra). The tube was blocked for 1 h at 37° C. with 2% skimmed milk powder in PBS (2% MPBS) and the selection, washing, and elution were performed as described (Marks et al. (1991), supra) using phage at a concentration of 5.0×10$^{12}$/ml. One third of the eluted phage was used to infect 1 ml log phase *E. coli* TG1, which were plated on TYE-AMP-GLU plates and described above. The rescue-selection-plating cycle was repeated 3 times, after which clones were analyzed for binding by ELISA.

All libraries were also selected using biotinylated c-erbB-2 ECD and streptavidin-coated paramagnetic beads as described (Hawkin et al. (1992) *J. Mol. Biol.* 226, 889–896) with some modifications. To prepare biotinylated antigen, 0.2 ml c-erbB-2 ECD (1 mg/ml) was incubated with 5 mM NHS-LC-Biotin (Pierce) overnight at 4° C. and then purified on a presto desalting column. For each round of selection, 1 ml of phage (approximately 10$^{13}$ t.u.) were mixed with 1 ml PBS containing 4% skimmed milk powder, 0.05% Tween 20, and biotinylated c-erbB-2 ECD. Affinity-driven selections were performed by decreasing the amount of biotinylated c-erbB-2 ECD used for selection. Two selection schemes were used.

In selection scheme 1 (S1) antigen concentrations of 10 nM, 50 nM, 10 nM, and 1 nM were used for selection rounds 1, 2, 3, and 4 respectively. In selection scheme 2 (S2) antigen concentrations of 40 nM, 1 nM, 100 pM, and 10 pM were used for selection rounds 1, 2, 3, and 4 respectively. The mixture of phage and antigen was gently rotated on an under-and-over-turntable for 1 hour at room temperature. To capture phage binding biotinylated antigen, streptavidin coated M280 magnetic beads (Dynabeads, Dynal) were blocked with 2% MPBS for 1 h at 37° C., and then added to the mixture of phage and antigen. In S1, 200 µl (round 1), 100 µl (round 2) or 50 µl (rounds 3 and 4) of beads were incubated with the phage-antigen mixture for 15 min, rotating on an under-and-over-turntable at room temperature. In S2, 100 µl (round 1) or 50 µl (rounds 2, 3, and 4) of beads were incubated with the phage-antigen mixture for 15 min (round 1), 10 min (round 2), or 5 min (rounds 3 and 4). After capture of phage, Dynabeads were washed a total of 10 times (3×PBS containing 0.05% Tween 20 (TPBS), 2×TPBS containing 2% skimmed milk powder, x PBS, 1×2% MPBS, and 2×PBS) using a Dynal magnetic particle concentrator. The Dynabeads were resuspended in 1 ml PBS, and 300 µl were used to infect 10 ml log phase *E. coli* TG1 which were plated on TYE-AMP-GLU plates.

Initial sFv characterization

Initial analysis of chain shuffled sFv clones for binding tc-erbB-2 was performed by ELISA using bacterial supernatant containing expressed sFv. Expression of sFv (De Bellis and Schwartz (1990) *Nucleic Acids Res.* 18, 1311) was performed in 96 well microtitre plates as described (Marks et al. (1991), supra) with the following exception. After overnight growth and expression at 30° C., 50 µl 0.5% Tween 20 was added to each well and the plates incubated for 4 h at 37° C. with shaking to induce bacterial lysis and increase the concentration of sFv in the bacterial supernatant. For selection performed on Immunotubes, ELISA plates (Falcon 3912) were incubated with c-erbB-ECD (2.5 µg/ml) in PBS at 4° C. overnight. For selections performed with biotinylated protein, Immunolon 4 plates (Dynatech) were incubated overnight at 4° C. with Immunopure avidin (10 µg/ml in PBS; Pierce). After washing 3 times with PBS to remove unbound avidin, wells were incubated with biotinylated c-erbB-2 ECD as in Example 1. In both cases, binding of sFv to c-erbB-2 ECD was detected with the mouse monoclonal antibody 9E10 (1 µg/ml), which recognizes the C-terminal peptide tag (Munro and Pelham (1986), *Cell* 46, 291–300) and peroxidase-conjugated anti-mouse Fc antibody (Sigma), as described (Marks et al., 1991, supra). Selected binders were further characterized by sequencing of the V$_H$ and V$_L$ genes (Sanger et al. (1977) *Proc. Nati. Acad. Sci. USA,* 74: 5463–5467). Sequence data has been deposited with the GenBank Data Library.

Screening of sFv for relative affinity was performed essentially as described (Friguet et al. (1985) *J. Immunol. Meth.* 77: 305–319). Immunolon 4 ELISA plates (Dynatech) were coated with avidin in PBS (10 μg/ml) at 4° C. overnight. Biotinylated c-erbB-2 ECD (5 μg/ml) was added to the wells and incubated for 30 min at room temperature. Bacterial supernatant containing sFv was incubated with varying concentrations of c-erbB-2 (0 to 100 nM) at 4° C. for 1 h. The amount of free sFv was then determined by transferring 100 μl of each mixture into the wells of the previously prepared ELISA plate and incubating for lh at 4° C. Binding of sFv was detected as under ELISA screening and the IC50 calculated as described (Friguet et al. (1985), supra)

Screening of sFv by dissociation rate constant ($k_{off}$) was performed using real-time biospecific interaction analysis based on surface plasmon resonance (SPR) in a BIAcore (Pharmacia). Typically 24 ELISA positive clones from each of the final two rounds of selection were screened. A 10 ml culture of *E. coli* TG1 containing the appropriate phagemid was grown and expression of sFv induced with IPTG (De Bellis and Schwartz, 1990). Cultures were grown overnight at 25° C., sFv harvested from the periplasm (Breitling et al. (1991) *Gene* 104, 147–153), and the periplasmic fraction dialyzed for 24 h against HEPES buffered saline (10 mM Hepes, 150 mM NaCl, pH 7.4, HBS). In a BlAcore flow cell, approximately 1400 resonance units (RU) of c-erbB-ECD (25 μg/ml) in 10 mM acetate buffer pH 4.5 were coupled to a CM5 sensor chip (Johnsson et al. (1991) *Anal. Biochem.* 198, 268–277). Association and dissociation of undiluted sFv in the periplasmic fraction was measured under a constant flow of 5 μl/min. An apparent dissociation rate constant ($k_{off}$) was determined from the dissociation part of the sensorgram for each sFv analyzed (Karlsson et al. (1991) *J. Immunol. Methods* 145, 229–240). Typically 30 to 40 samples were measured during a single BIAcore run, with C6.5 periplasmic preparations analyzed as the first and final samples to ensure stability during the run. The flow cell was regenerated between samples using 2.6 M $MgCl_2$ in 10 mM glycine, pH 9.5 without significant change in the sensorgram baseline after analysis of more than 100 samples.

Subcloning, expression and purification of Single-chain Fv.

To facilitate purification, shuffled sFv genes were subcloned (Example 1) into the expression vector pUC11Sfi-NotmycHis, which results in the addition of a hexa-histidine tag at the C-terminal end of the sFv. 200 ml cultures of *E.coli* TG1 harboring one of the C6.5 mutant phagemids were grown, expression of sFv induced with IPTG (De Bellis and Schwartz (1990), supra) and the culture grown at 25° C. overnight. Single-chain Fv was harvested from the periplasm (Breitling et al. (1991), supra) dialyzed overnight at 4° C. against 8 L of IMAC loading buffer (50 mM sodium phosphate, pH 7.5, 500 mNaCl, 20 mM imidazole) and then filtered through a 0.2 micron filter.

Single-chain Fv was purified by immobilized metal affinity chromatography (IMAC) (Hochuli et al. (1988) *Bio/Technology*, 6, 1321–1325) as described in Example 1. To remove dimeric and aggregated sFv, samples were concentrated to a volume <1 ml in a Centricon 10 (Amicon) and fractionated on a Superdex 75 column using a running buffer of HBS. The purity of the final preparation was evaluated by assaying an aliquot by SDS-PAGE. Protein bands were detected by Coomassie staining. The concentration was determined spectrophotometrically assuming an $A_{280}$ nm of 1.0 corresponds to an sFv concentration of 0.7 mg/ml.

Measurement of affinity, kinetics, and cell suface retention

The $K_d$ of light chain shuffled C6.5 mutants isolated from phage selection using Immunotubes (Nunc) were determined by Scatchard analysis. All assays were performed in triplicate. Briefly, 50 mg of radioiodinated sFv was added to $5 \times 10^6$ SK-OV-cells in the presence of increasing concentrations of unlabeled sFv from the same preparation. After a 30 minute incubation at 20° C., the samples were washed with PBS at 4° C. and centrifuged at 500 g. The amount of labeled sFv bound to the cells was determined by counting the pellets in a gamma counter and the $K_a$ and $K_d$ were calculated using the EBDA program (V 2.0, G. A. McPherson, 1983). The $K_d$ of all the other isolated sFv were determined using surface plasmon resonance in a BIAcore (Pharmacia). In a BIAcore flow cell, approximately 1400 resonance units (RU) of c-erbB-2 ECD (25 μg/ml in 10 mM sodium acetate, pH 4.5) was coupled to a CM5 sensor chip (Johnsson et al. (1991), supra). Association and dissociation-rates were measured under continuous flow of 5 ml/min using a concentration range from 50 to 800 nM. Rate constant $k_{on}$ was determined from a plot of (1(dR/dt))/t vs concentration (Karlsson et al. (1991), supra). Rate constant $k_{off}$ was determined from the dissociation part of the sensorgram at the highest concentration of sFv analyzed. Cell surface retention of C6.5 and C6L1 was determined as described in Example 1.

Modeling of location of mutations

The location of mutations in shuffled sFv was modeled on the structure of the Fab KOL (Marquart et al. (1980) *J. Mol. Biol.* 141, 369–391) using Maclmdad v5.0 (Molecular Applications Group, Palo Alto, Calif.) running on an Apple MacIntosh Quadra 650.

Results

Construction of shuffled phage antibody libraries

To facilitate heavy chain shuffling, libraries were constructed in pHEN-1 (Hoogenboom et al. (1991), supra) containing human VH gene repertoires (FR1 to FR3) and cloning sites for inserting the $V_H$ CDR3FR4, single chain linker, and light chain gene from a binding sFv as a BssHII-NotI fragment. Three heavy chain shuffling libraries were created (pHEN-1-$V_H$1rep, pHEN-1-$V_H$3rep, and pHEN-1-$V_H$5rep), each enriched for $V_H$1, $V_H$3, or $V_H$5 genes by using PCR primers designed to anneal to the consensus sequence of the 3' end of $V_H$1, $V_H$3, or $V_H$FR3 (Tomlinson et al. (1992), supra). These primers also introduced a BssHII site at the end of FR3, without changing the amino acid sequence typically observed at these residues. Libraries of $5.0 \times 10^5$ clones for pHEN-1-$V_H$1rep, $1.0 \times 10^6$ clones for pHEN-1-$V_H$3rep and $1.5 \times 10^6$ clones for pHEN-1-$V_H$5rep were obtained. Analysis of 50 clones from each library indicated that greater than 80% of the clones had inserts, and the libraries were diverse as shown by the BstNI restriction pattern (Marks et al. (1991), supra). Three heavy chain shuffled libraries were made by cloning the C6.5 $V_H$ CDR3, FR4, linker, and light chain genes into the previously created $V_H$1. $V_H$3, or $V_H$5 repertoire using the BssHII and NotI restriction sites. After transformation, libraries of 1.0–2.0×10⁶ clones were obtained. PCR screening revealed that 100% of clones analyzed had full length insert and diverse BstNI restriction pattern. Prior to selection, 20/92 clones selected at random from the $V_H5$ library expressed sFv which bound c-erbB-2. 0/92 clones selected at random from the $V_H1$ or $V_H$ repertoire expressed sFv which bound c-erbB-2.

To facilitate light chain shuffling, a library was constructed in pHEN-1 containing human $V_k$ and $V_l$ gene repertoires, single chain linker DNA, and cloning sites for inserting the $V_H$ gene from binding sFv as an NcoI-XhoI fragment. The resulting library (pHEN-1-V₁rep) consisted of 4.5×10⁶ clones. PCR screening revealed that 95% of clones analyzed had full length insert and a diverse BstNI restriction pattern. A light chain shuffled library was made by cloning the C6.5 $V_H$ gene into pHEN-1-V₁rep. After transformation a library of 2.0×10⁶ clones was obtained. PCR screening revealed that 100% of clones analyzed had full length insert and a diverse BstNI restriction pattern. Prior to selection, 0/92 clones selected at random expressed sFv which bound c-erbB-2.

Isolation and characterization of higher affinity light chain shuffled scF

In a first approach to increase affinity, c-erbB-2 ECD coated polystyrene tubes were used for selecting the light chain shuffled library. Phage were subjected to three rounds of the rescue-selection-infection cycle. One hundred and eighty clones from the 2nd and the 3rd round of selection were analyzed for binding to recombinant c-erbB-2 ECD by ELISA. After the 3rd round of selection, greater than 50% of the clones were positive by ELISA (Table 8).

TABLE 8

Frequency of binding sFv and percent of binding sFv with slower $k_{off}$ than C6.5. binding was determined by ELISA. Rate constant $k_{off}$ was determined by BIAcore on unpurified sFv in bacterial periplasm.

| Library and method of selection | ELISA Round of Selection | | | sFv with slower $k_{off}$ than C6.5 (parental sFv) Round of Selection | | |
|---|---|---|---|---|---|---|
| | 2 | 3 | 4 | 2 | 3 | 4 |
| $V_L$-shuffling, selected on: antigen coated immunotubes | 41/180 | 97/180 | ND | ND | ND | ND |
| soluble antigen (rd 1, 100 nM; rd 2, 50 nM; rd 3 10 nM; rd 4, 1 nM). | 74/90 | 22/90 | 13/90 | ND | 0% | 42% |
| soluble antigen (rd 1, 40 nM; rd 2, 1 nM,; rd 3, 0.1 nM; rd 4, 0.01 nM) | ND | 65/90 | 62/90 | ND | 25% | 84% |
| $V_H$-shuffling, selected on: soluble antigen; (rd 1, 100 nM; rd 2, 50 nM; rd 3, 10 nM; rd 4, 1 nM) | ND | 43/90 | 56/90 | ND | 0% | 0% |
| soluble antigen (rd 1, 40 nM; rd 2, 1 nM; rd 3, 0.1 nM; rd 4, 0.01 nM) | ND | 90/90 | 82/90 | ND | 0% | 12% | rd = round, ND = not determined, nM = 1.0 × 10⁻⁹M

TABLE 9

$IC_{50}$ and $K_d$ of C6.5sFv and 4 chain shuffled mutant sFvs. $IC_{50}$ was determined by competition ELISA and $K_d$ by Scatchard after radioiodination.

| sFv | $IC_{50}$ (M) | $K_d$ (M) |
|---|---|---|
| C6.5 | 2.0 × 10⁻⁸ | 2.0 × 10⁻⁸ |
| C6VLB | 1.0 × 10⁻⁸ | 3.0 × 10⁻⁸ |
| C6VLD | 5.8 × 10⁻⁹ | 2.6 × 10⁻⁸ |
| C6VLE | 2.8 × 10⁻⁹ | 7.1 × 10⁻⁸ |
| C6VLF | 7.5 × 10⁻⁹ | 7.9 × 10⁻⁸ |

TABLE 10

Deduced protein sequences of light chain variable region genes of C6.5 and chain shuffled mutants.

```
                                                                           SEQ ID NO:
            Framework 1              CDR1         Framework 2    CDR2
            10        20             30        35        40        50
C6.5    QSVLTQPPSVSAAPGQKVTISC  SGSSSNIGNNYVS  WYQQLPGTAPKLLIY  GHTNRPA     36

Light chain shuffled mutants selected on polystyrene adsorbed antigen:

C6VLB   ---------------------  -------------  ---------------  SDNQ--S     39

C6VLD   ---------------------  --TN---------  ---------------  TNDQ--S     40

C6VLE   -------------A-------  -----S--R----  -N------  -----W RNNQ--S     41

C6VLF   ---------M-----------  -------------  ----F---------H  DNNK--S     42

Light chain shuffled mutant selected on biotinylated antigen:

C6L1    -----------G----W----  -------------  ---------------  DNNK--S     43
```

```
                                                                           SEQ ID NO:
            Framework 3                 CDR3        Framework 4
            60      70       80        90         100
C6.5    GVPDRFSGSKSGTSASLAISGFRSEDEADYYC  AAWDDSLSG WV  FGGGTKLTVLG         36

Light chain shuffled mutants selected on polystyrene adsorbed antigen:

C6VLB   ---------------------L----------  ---------H--  ------------        39

C6VLD   ---------------------LQ---------  -------N- -M  ------------        40

C6VLE   ---------------------V----------  -S--N---- --  ------------        41

C6VLF   -I---I---------------LQ-D-------  -------N- --  ------------        42

Light chain shuffled mutant selected on biotinylated antigen:

C6L1    ---------Q-----------L----------  --------- --  ------------        43
```

CDR, complementarity determining region; dashes indicate sequence identity. Numbering is according to Kabat etal., 1987, supra.. Underlined residues are those that form the β-sheet interface that packs on the VH domain (Chothia etal., 1985 supra).

Positive clones were ranked by $IC_{50}$ as determined by competition ELISA (Table 9). Sixteen sFv with $IC_{50}$s less than the $IC_{50}$ of the parental sfv were sequenced and four unique DNA sequences identified (Table 10). These clones were purified by IMAC after subcloning into PUC119SFI/ NotmycHis, and the affinity determined by Scatchard analysis.

Despite their lower $IC_5$0s, none of these 4 sfv had a higher affinity for c-erbB-2 (Table 9). Gel filtration analysis of the four purified sfv demonstrated the presence of two species, with size consistent for monomeric and dimeric sfv. In contrast, the parental sFv existed only as monomer.

As a result of these observations, it was hypothesized that selection on immobilized antigen favored the isolation of lower affinity dimeric sFv which could achieve a higher apparent affinity due to avidity. In addition, determination of $IC_{50}$ by inhibition ELISA using native sFv in periplasm did not successfully screen for sFv of higher affinity. To avoid the selection of lower affinity dimeric sFv, subsequent selections were performed in solution by incubating the phage with biotinylated c-erbB-2 ECD, followed by capture on streptavidin coated magnetic beads. To select phage on the basis of affinity, the antigen concentration was reduced each round of selection to below the range of the desired sFv $K_d$ (Hawkins et al. (1992), supra). To screen ELISA positive sFv for improved binding to c-erbB-2, a BIAcore was used. Periplasm preparations containing unpurified native sFv can be applied directly to a c-erbB-2 coated BIAcore flow cell, and the $k_{off}$ determined from the dissociation portion of the sensorgram. This permitted ranking the chain shuffled clones by $k_{off}$. Moreover, by plotting In $(Rn/R_0)$ vs t, the presence of multiple $k_{off}$ can be detected, indicating the presence of mixtures of monomeric and dimeric sFv. This strategy of selecting on antigen in solution, followed by BIAcore screening of ELISA positive sFv, was used to isolate higher affinity chain shuffle mutants.

The light chain shuffled library was subjected to four rounds of selection on decreasing soluble antigen concentration (100 Nm, 50 Nm, 10 Nm, and, 1 Nm). In a separate set of experiments, the 4 rounds of selection were performed using 40 nM, 1 nM, 0.1 nM, and 0.01 nM antigen concentration. Using the higher set of antigen concentrations for selection, 13/90 clones were positive for c-erbB-binding by ELISA after the 4th round of selection. In the BIAcore, 42% of these clones had a slower $k_{off}$ than the parental sFv. Using the lower set of antigen concentrations for selection, more clones were positive for c-erbB-2 binding by ELISA (62/90) after the 4th round of selection, and 84% had a slower $k_{off}$ than the parental sFv. Sequencing of the $V_L$ gene of ten of these sFv revealed one unique sFv (C6L1) (Table 10). The $V_\lambda$ gene of C6L1 was derived from the same germline gene as the parental sFv, but had 9 amino acid substitutions. The C6L1 gene was subcloned and the sFv purified by IMAC and gel filtration. C6L1 sFv was monomeric as determined by gel filtration and had an affinity 6 times higher than parental (Table 11). The increased affinity was due to both a faster $k_{on}$ and a slower $k_{off}$ (Table 11). The slower $k_{off}$ was associated with a three fold increase in the retention of sFv on the surface of SK-OV-3 cells (28% at 30 minutes for C6L1 compared to 10% at 3 minutes for the parental sFv).

TABLE 11

Affinities and binding kinetics of c-erbB-2 binding Single-chain Fv, $K_d$, $k_{on}$ and $k_{off}$ were determined by surface plasmon resonance in a BIAcore. Combined Single-chain Fv result from combining the $V_L$ of C6L1 with the $V_H$ of either C6H1 or C6H2.

| sFv source and clone name | $K_d$ (M) | $k_{on}$ (M$^{-1}$s$^{-1}$) | $k_{off}$ (M$^{-1}$s$^{-1}$) |
|---|---|---|---|
| Parental C6.5 | $1.6 \times 10^{-8}$ | $4.0 \times 10^{-5}$ | $6.3 \times 10^{-3}$ |
| Light Chain Shuffled C6L | $2.6 \times 10^{-9}$ | $7.8 \times 10^{-5}$ | $2.0 \times 10^{-3}$ |
| Heavy Chain Shuffled | | | |
| C6H1 | $5.9 \times 10^{-9}$ | $1.1 \times 10^{-6}$ | $6.2 \times 10^{-3}$ |
| C6H2 | $3.1 \times 10^{-9}$ | $8.4 \times 10^{-5}$ | $2.6 \times 10^{-3}$ |
| Combined sFv | | | |
| C6H1L1 | $1.5 \times 10^{-8}$ | $4.1 \times 10^{-5}$ | $6.2 \times 10^{-3}$ |
| C6H2L1 | $6.0 \times 10^{-9}$ | $3.0 \times 10^{-5}$ | $1.8 \times 10^{-3}$ |

Isolation and characterization of higher affinity heavy chain shuffled scf.

The VH5 heavy chain shuffled library was subjected to four rounds of selection on decreasing soluble antigen concentration (100 Nm, 5 nM, 10 Nm, and, 1 Nm). In a separate set of experiments, the rounds of selection were performed using 40 Nm, 1 Nm, 0.1 Nm, and 0.01 Nm antigen concentration. Using the higher set of antigen concentrations for selection, 56/90 clones were positive for c-erbB-binding by ELISA after the 4th round of selection. None of these clones, however, had a slower $k_{off}$ than the parental sFv. Using the lower set of antigen concentrations for selection, more clones were positive for c-erbB-2 binding by ELISA (82/90) after the 4th round of selection, and 12% had a slower $k_{off}$ than the parental sFv. No binders were isolated from either the $V_H1$ or $V_H3$ shuffled libraries. Sequencing of the $V_H$ gene of all slower $k_{off}$ clones revealed two unique sFv, C6H1 and C6H2 (Table 12). The $V_H$ genes of C6H1 and C6H2 were derived from the same germline gene as the parental sFv, but differed by 7 and 9 amino acids respectively. C6H1 also had a stop codon in the heavy chain CDR1 and was expressed as a PIII fusion due to read through, albeit at very low levels. The two sFv were subcloned and purified by IMAC and gel filtration. Both sFv were monomeric as determined by gel filtration C6H1 had 3 fold higher affinity for c-erbB2 than C6.5 and C6H2 had 5 fold higher affinity than C6.5 (Table 11). The increased affinity of C6H($5.9 \times 10^{-9}$ M) was due to a faster $k_{on}$, whereas the increased affinity of C6H2 ($3.1 \times 10^{-9}$ M) was due to both a faster $k_{on}$ and slower $k_{off}$ (Table 11).

Location of mutations in chain shuffled scf

Mutations in chain shuffled sFv were modeled on the Fv fragment of the immunoglobulin KOL (Marquart et al. (1980), supra) (FIGS. 2 and 3). KOL was selected as the model because it has a $V_\lambda$ gene derived from the same family as C6.5, and a $V_H$ gene with the same length CDR2. Mutations in higher affinity sFv were located both in surface residues at the antigen combining site, as well as residues located far from the binding site (FIG. 2). Except for two conservative mutations in $V_H$ framework 3 (V89M and F91Y), no mutations were located in residues which form the two 5 stranded B-sheets that form the $V_H$–$V_L$ interface (Chothia et al. (1985) *J. Mol. Biol.* 186, 651–663) (FIG. 2 and Tables 10 and 12). In contrast, all 4 light chain shuffled sFv which formed mixtures of monomer and dimer had mutations in residues which formed the β-sheet that packs on the $V_H$ domain (Table 4 and FIG. 3).

TABLE 12

Deduced protein sequences of heavy chain variable region genes of C6.5 and chain shuffled mutants.

```
         Framework 1           CDR1    Framework 2     CDR2         Framework 3             CDR3       Framework 4
         10        20          30      40       50     60     70    80 abc    90       100
         QVQLLQSGAELKKPGESLKISCKGSGYSFT SYWIA WVRQMPGKGLEYMG LIYPGDSDTKYSPSFQG QVTISVDKSVSTAYLQWSSLKPSDSAVYFCAR HDVGYCSSNCAKWPFYFQH WGQGTLV    SEQ ID NO:
C6.5                                                                                                                                           44

Heavy chain shuffled mutants selected on high concentration biotinylated antigen:

C6VHA2   ----V---G-M-------------------- T----- -------------- ---L--D--------- --------------------R---T-M-Y--- ------------------- -------    45
C6VHB2   ----Q---G-M-------------------- T----- -------------- ---L--D--------- --------------------------T-M-Y- ------------------- -------    46
C6VHC2   ----Q---G-M-------------------- -E---S -------------- ---------------- --A-E-I----------E--------A-T-M-Y- ------------------- -------    47
C6VHD2   ---VE---M---------------------- ---F-D-S -------------- ---------------- -------T--------------R---T---Y--- ------------------- -------    48
C6VHE2   ---VE---G-M---R---------------- T----- -------------- ---L--D--------- --------------------------T-M-Y- ------------------- -------    49
C6VHF2   ---VE---G-M-------------------- T----- -------------- ---L--D-S------- --------------------R-----T-M-Y- ------------------- -------    50
C6VHG2   ---VE---G-M-------------------- T----- -------------- ---L--D--------- --------------------R-----T-M-Y- ------------------- -------    51
C6VHH2   ---VE---M---------------------- ---F-D-S -------------- ---------------- --------------------R-----T-M-Y- ------------------- -------    52
C6VHA3   ----V---G-M-------------------- T----- -------------- ---L--D--------- --------------------R-----T-M-Y- ------------------- -------    45
C6VHB3   ----V---G-M-------------------- T----- -------------- ---L--D-S------- --A-E-I----------E--------A-T-M-Y- ------------------- -------    53
C6VHC3   ----V---G-M-------------------- T----- -------------- ---------------- --------------------R-----T-M-Y- ------------------- -------    45
C6VHD3   ----V---G-M-------------------- T----- -------------- -----IR------E-- --R-I------------T--------A-T-M-Y- ------------------- -------    54
C6VHE3   ---VE---G-M---R---------------- T----- -------------- ---L--D--------- --------------------R-----T-M-Y- ------------------- -------    49
C6VHF3   ---------M--------------------- ---F-D-S -------------- ---------------- --------------------------T-M-Y- ------------------- -------    55
C6VHG3   --------V-------Q--------------- -----D--T-Y- -------------- -I-----R-I------- --R-A---------------A-----T-M-Y- ------------------- -------    56
C6VHH3   -----E---V-E-Q------F-D-S -------------- ---------------- --------------------------T-M-Y- ------------------- -------    57

Heavy chain shuffled mutants selected on lower concentration biotinylated antigen:

(E)
C6H1     ----VE----v--R----------------- ----*- -------------- ---------------- --------------------------T-M-Y- ------------------- -------    58
C6H2     ----V-----v--R----------------- ------ -------------- -----A-K-I------ --------------------T-----T-M-Y- ------------------- -------    59
```

CDR, complementarity determining region; dashes indicate sequence identity. Numbering is according to Kabat et al. 1987, supra. Underlined residues are those that form the β-sheet interface that packs on the V_L domain (Chothia et al. 1985 supra.).

Affinities of sFv resulting from combining higher affinity $V_H$ and $V_L$ genes obtained by chain shuffling.

In an attempt to further increase affinity, shuffled $V_H$ and $V_L$ genes from higher affinity sFv were combined into the same sFv. Combining the $V_L$ gene from C6L1 with the $V_H$ gene from C6H1 resulted in an sFv (C6H1L1) with lower affinity than either C6L1 or C6H2 (Table 11). No additional reduction in $k_{off}$ was achieved, and the $k_{on}$ was reduced approximately 2 fold. Similarly, combining the $V_L$ gene from C6L1 with the $V_H$ gene from C6H2 resulted in an sFv (C6H2L1) with lower affinity than C6L1 or C6H2 (Table 11). No additional reduction in $k_{off}$ was achieved, and the $k_{on}$ was reduced approximately 2 fold. Thus, in both instances, combining the independently isolated higher affinity $V_H$ and $V_L$ genes had a negative effect on affinity.

Example 3

Production of Higher Affinity Mutants

In order to prepare higher affinity mutants derived from C6.5 part of the light chain and heavy chain CDR3 were sequentially randomized. The C6.5 VL CDR3 was modified by randomizing the sequence AAWDDSLSG (SEQ ID NO:60). The heavy chain CDR3 domain was randomized. The variable heavy chain CDR3 was randomized 4 amino acids at a time: In other words, the CDR3 sequence of HDVGYCSSSNCAKWPEYFQH (SEQ ID NO:61) was modified by randomizing SSSN (SEQ ID NO:62) (library B), DVGY (SEQ ID NO:63) (library A), AKPE (SEQ ID NO:64) (library C) and YFQH (SEQ ID NO:65) (library D) respectively as described below.

I. Materials and Methods

Construction of phage antibody libraries

As explained above, mutant sFv phage antibody libraries were constructed based on the sequence of C6.5, a human sFv isolated from a non-immune phage antibody library which binds to the tumor antigen c-erbB-2 with a Kd of $1.6 \times 10^{-8}$ M (see Example 1). For construction of a library containing $V_L$ CDR3 mutants, an oligonucleotide (VL1; Table 18) was designed which partially randomized nine amino acid residues located in $V_L$ CDR3 (Table 4, above). For the nine amino acids randomized, the ratio of nucleotides was chosen so that the frequency of wild-type (wt) amino acid was 49%.

To create the library, C6.5 sFv DNA (10 ng) was amplified by PCR in 50 µl reactions containing 25 pmol LMB3 (Marks et al., 1991 *J. Mol. Biol.* 222: 581–597), 25 pmol VL1, 250 µM dNTPs, 1.5 mM $MgCl_2$, and 1 µl (5 units) Taq DNA polymerase (Promega) in the manufacturers buffer. The reaction mixture was subjected to 30 cycles of amplification (94° C. for 30 s, 50° C. for 30 s and 72° C. for 1 min) using a Hybaid OmniGene cycler.

To introduce a NotI restriction site at the 3' end of the sFv gene repertoire, the PCR fragment (850 bp) was gel purified and reamplified using the primers LMB3 and VL2 (Table 18). The PCR product was purified, digested with SfiI and NotI, and ligated into pCANTAB5E (Pharmacia) digested with SfiI and NotI.

Ligation mixtures were purified as previously described above and aliquots electroporated (Dower et al. (1988) *Nucleic Acids Res.*, 16: 6127–45) into 50 µl *E. coli* TG1 (Gibson (1984) Studies on the Epstein-Barr virus genome. PhD thesis, University of Cambridge). Cells were grown in 1 ml SOC (Sambrook et al., (1990) supra.) for 30 min and then plated on TYE (Miller, J. H. (1972) *Experiments in Molecular Genetics,* Cold Springs Harbor Lab Press, Cold Springs Harbor, N.Y.) media containing 100 µg ampicillin/ml and 1 % (w/v) glucose (TYE-AMP-Glu). Colonies were scraped off the plates into 5 ml of 2×TY broth (Miller (1972) supra.) containing 100 µg ampicillin/ml, 1% glucose (2×TY-AMP-Glu) and 15% (v/v) glycerol for storage at –70° C. The cloning efficiency and diversity of libraries was determined by PCR screening (Gussow & Clackson (1989) *Nucleic Acids Res.* 17) exactly as described in (Marks et al., (1991) supra.) and by DNA sequencing (Sanger et al. (1977) *Proc. Natl. Acad. Sci. USA,* 74: 5463–7). The mutant phage antibody library was designated C6VLCDR3.

Four libraries of $V_H$ CDR3 mutants were constructed. For construction of each $V_H$ CDR3 library, oligonucleotides (VHA, VHB, VHC, and VHD; Table 18) were designed which completely randomized four amino acid residues located in $V_H$ CDR3 (amino acid residues 96 to 99, library A; residues 100a to 100d, library B; residues 100f, 100g, 100i, and 100j, library C; and residues 100k to H102, library D; Table 13). To create the libraries, DNA encoding the $V_H$ gene of C6.5 sFv DNA (10 ng) was amplified by PCR in 50 µl reactions containing 25 pmol LMB3 (Marks et al., 1991) and 25 pmol of either VHA, VHB, VHC, or VHD exactly as described above. The resulting PCR fragments were designated VHA1, VHB1, VHC1, and VHD1, based on the mutagenic oligonucleotide used for amplification. In four separate PCR reactions, DNA encoding the light chain, sFv linker, $V_H$ framework 4 (FR4), and a portion of $V_H$ CDR3 of C6ML3-9 was amplified by PCR as described above using the primers C6hisnot and either RVHA, RVHB, RVHC, or RVHD (Table 18).

These amplifications yielded PCR fragments VHA2, VHB2, VHC2, and VHD2. The 5' end of primers RVHA, RVHB, RVHC, and RVHD were designed to be complementary to the 5' ends of primers VHA, VHB, VHC, and VHD respectively. This complementarity permits joining of the VH1 and VH2 PCR fragments together to create a full length sFv gene repertoire using splicing by overlap extension. To create the mutant sFv gene repertoires, 200 ng of each PCR fragment (VHA1 and VHA2, VHB1 and VHB2, VHC1 and VHC2, or VHD1 and VHD2) were combined in 50 ml PCR reaction mixtures (as described above) and cycled seven times to join the fragments (94° C. for 30 s, 60° C. for 5 s, 40° C. for 5 s (RAMP: 5 s), 72° C. for 1 min). After seven cycles, outer primers LMB3 and C6hisnot were added and the mixtures amplified for 30 cycles (94° C. for 30 s, 50° C. for 30 s, 72° C. for 1 min). The PCR products were purified as described above, digested with SfiI and NotI, and separately ligated into pCANTAB5E (Pharmacia) digested with SfiI and NotI. The four ligation mixtures were purified as described above and electroporated into 50 µl *E. coli* TG1. Transformed cells were grown and plated, and libraries characterized and stored, as described above. The mutant phage antibody libraries were designated C6VHCDR3A, C6VHCDR3B, C6VHCDR3C, and C6VHCDR3D.

Preparation of phage and selection of phage antibody libraries.

Preparation of phage for selection was performed exactly as described in Examples 1 and 2. Phage particles were purified and concentrated by two PEG-precipitations (Sambrook et al., 1990), resuspended in 5 ml phosphate buffered saline (25 mM $NaH_2PO_4$, 125 mM NaCl, pH 7.0, PBS) and filtered through a 0.45 $\mu$ filter. All libraries were selected using biotinylated c-erbB-2 ECD and streptavidin-coated paramagnetic beads M280 (Dynal) as described above. For selection of the C6VLCDR3 library, c-erbB-2 ECD concentrations of $4.0\times10^{-8}$ M, $1.0\times10hu -9$ M, $1.0\times10^{-10}$ M, and $1.0\times10^{-11}$ M were used for selection rounds 1, 2, 3, and 4 respectively. The mixture of phage and antigen was gently rotated for 1 h at room temperature and phage bound to biotinylated antigen captured using 100 $\mu$l (round 1) or 50 $\mu$l (rounds 2, 3, and 4) of streptavidin-coated M280 magnetic beads. After capture of phage, Dynabeads were washed a total of ten times (three times in PBS containing 0.05% Tween 20 (TPBS), twice in TPBS containing 2% skimmed milk powder (2% MTPBS), twice in PBS, once in 2% MPBS, and twice in PBS) using a Dynal magnetic particle concentrator. The Dynabeads were resuspended in 1 ml PBS, and 300 $\mu$l were used to infect 10 ml log phase $E. coli$ TG1 which were plated on TYE-AMP-Glu plates. For selection of the C6VHCDR3 libraries, c-erbB-2 ECD concentrations of $5.0\times10^{-9}$ M, $5.0\times10^{-11}$ M, $5.0\times10^{-12}$ M, and $5.0\times10^{-13}$ M were used for selection rounds 1, 2, 3, and 4 respectively and the phage captured by incubating with 50 $\mu$l of Dynabeads for 5 min.

The washing protocol was altered to select for sFv with the lowest $k_{off}$ (Hawkins et al. (1992) $J.\ Mol.\ Biol.$ 226: 889–896). Dynabeads with bound phage were initially subjected to five rapid washes (4×TPBS, 1×MPBS) followed by six 30 min incubations in one of three washing buffer (2×TPBS, 2×MPBS, 2×PBS) containing $1.0\times10^{-7}$ M c-erbB-2 ECD. Bound phage were eluted from the Dynabeads by sequential incubation with 100 $\mu$l of 4 M $MgCl_2$ for 15 min followed by 100 $\mu$l of 100 mM HCl for 5 min. Eluates were combined and neutralized with 1.5 ml of 1 M Tris HCl, pH 7.5 and one third of the eluate used to infect log phase $E.\ coli$ TG1.

Initial sFv characterization.

Initial analysis of selected sFv clones for binding to c-erbB-2 ECD was determined by phage ELISA. To prepare phage for ELISA, single ampicillin resistant colonies were transferred into microtitre plate wells containing 100 $\mu$l 2×TY-AMP-0.1% glucose and grown for three hours at 37° C. to an $A_{600}$ of approximately 0.5. VCSM13 helper phage ($2.5\times10^8$ phage) were added to each well, and the cells incubated for 1 hour at 37° C.

Kanamycin was then added to each well to a final concentration of 25 $\mu$g/ml and the bacteria grown overnight at 37° C. Supernatants containing phage were used for ELISA. For ELISA, Immunolon 4 plates (Dynatech) were incubated overnight at 4° C. with ImmunoPure avidin (10 $\mu$g/ml in PBS; Pierce). After washing three times with PBS to remove unbound avidin, wells were incubated with biotinylated c-erbB-2 ECD as described above.

Binding of sFv phage to c-erbB-2 ECD was detected with peroxidase-conjugated anti-M13 antibody (Pharmacia) and ABTS (Sigma) as substrate. Selected binders were further characterized by DNA sequencing of the $V_H$ and $V_L$ genes.

Ranking of sFv by $k_{off}$ was performed using SPR in a BIAcore as described above. Briefly, 10 ml cultures of 24 ELISA positive clones from the third and fourth round of selection were grown to an $A_{600}$ of approximately 0.8, sFv expression induced (De Bellis et al. (1990). $Nucleic\ Acids\ Res.$, 18: 1311) and the culture grown overnight at 25° C. Single-chain Fv were harvested from the periplasm (Breitling et al. (1991) $Gene$, 104: 147–153), and the periplasmic fraction dialyzed for 48 h against hepes buffered saline (10 mM hepes, 150 mM NaCl, pH 7.4, HBS). In a BIAcore flow cell, approximately 1400 resonance units (RU) of c-erbB-2 ECD were coupled to a CM5 sensor chip using NHS-EDC chemistry (Johnsson et al. (1991) $Anal.\ Biochem.$ 198: 268–277). Association and dissociation of undiluted sFv in the periplasmic fraction were measured under a constant flow of 5 $\mu$l/min and HBS as running buffer. An apparent $k_{off}$ was determined from the dissociation part of the sensorgram for each sFv analyzed (Karlsson et al. (1993) $J.\ Immunol.\ Meth.$ 166: 75–84). The flow cell was regenerated between samples using sequential injections of 4 M $MgCl_2$ and 100 mM triethylamine without significant change in the sensorgram baseline after analysis of more than 100 samples.

Subvloning, expression and purification of sFv.

To facilitate purification of sFv selected from the C6VLCDR3 library, the sFv genes were subcloned into the expression vector pUC119 Sfi-NotmycHis, which results in the addition of a hexa-histidine tag at the C-terminal end of the sFv. The sFv selected from the C6VHCDR3 library already have a C-terminal hexa-histidine tag and therefore could be purified without subcloning. 500 ml cultures of $E.\ coli$ TG1 harboring one of the C6.5 mutant phagemids were grown, expression of sFv induced (De Bellis et al. (1990) supra.), and the culture grown at 25° C. overnight. Single-chain Fv were harvested from the periplasm (Breitling et al. (1991) supra.), dialyzed overnight at 4° C. against 8 L of IMAC loading buffer (50 mM sodium phosphate, pH 7.5, 500 mM NaCl, 20 mM imidazole) and then filtered through a 0.2 micron filter. Single-chain Fv was purified by IMAC (Hochuli et al. (1988) $Bio/Technology$, 6: 1321–1325) as described above.

To separate monomeric, dimeric and aggregated sFv, samples were concentrated to a volume <1 ml in a Centricon 10 (Amicon) and fractionated on a Superdex 75 column using a running buffer of HBS. The purity of the final preparation was evaluated by assaying an aliquot by SDS-PAGE. Protein bands were detected by Coomassie staining. The concentration was determined spectrophotometrically, assuming an $A_{280}$ nm of 1.0 corresponds to an sFv concentration of 0.7 mg/ml.

Measurement of affinity and binding kinetics.

The $K_d$ of sFv were determined using SPR in a BlAcore. In a BIAcore flow cell, approximately 1400 RU of c-erbB-2 ECD (90 kDa, McCartney et al. (1995) $Protein\ Eng.$ 8: 301–314) were coupled to a CM5 sensor chip (Johnsson et al. (1991) supra.). Association rates were measured under continuous flow of 5 ml/min using concentrations ranging from $5.0\times10^{-8}$ to $8.0\times10^{-7}$ M. Rate constant $k_{on}$ was determined from a plot of (ln (dR/dt))/t vs concentration (Karlsson et al., 1991).

To verify that differences in $k_{on}$ were not due to differences in immunoreactivity, the relative concentrations of functional sFv was determined using SPR in a BIAcore (Karlsson et al. (1993) supra.). Briefly, 4000 RU of c-erbB-2 ECD were coupled to a CM5 sensor chip and the rate of binding of C6.5 (RU/s) determined under a constant flow of 30 ml/min. Over the concentration range of $1.0\times10^{-9}$ to $1.0\times10^{-7}$ M, the rate of binding was proportional to the log of the sFv concentration. Purified sFv were diluted to the same concentration ($1.0\times10^{-8}$ M and $2.0\times10^{-8}$ M) as determined by $A_{280}$. The rate of binding to c-erbB-2 ECD was measured and used to calculate the concentration based on the standard curve constructed from C6.5. Dissociation rates were measured using a constant flow of 25 μl/min and a sFv concentration of $1.0\times10^{-6}$ M. $k_{off}$ was determined during the first 2 min of dissociation for sFv mutated in $V_L$ CDR3 (Karlsson et al. (1991) supra.) and during the first 15 to 60 min for clones with $k_{off}$ below $5\times10^{-4}$ s$^{-1}$ (sFv mutated in $V_H$ CDR3 and combined sFv). To exclude rebinding, $k_{off}$ was determined in the presence and absence of $5.0\times10^{-7}$ M c-erbB-2 ECD as described above in Examples 1 and 2.

Cell surface retention assay.

The cell surface retention of selected sFv was determined on live SK-OV-3 cells using a fluorescence activated cell sorter (FACS). Purified sFv were labeled with NHS-LC-Biotin (Pierce) using the manufacturers instructions. The concentration of immunoreactive biotinylated sFv was calculated using SPR as described above. The efficiency of biotinylation was also determined in a BIAcore using a flow cell to which 5000 RU of streptavidin was coupled. The total responses after association were compared between samples and concentrations of sFv were adjusted using the results obtained from the BIAcore. For the assay, aliquots of SK-OV-3 cells ($1.2\times10^7$ c-erbB-2 positive cells) were incubated with 14 μg biotinylated sFv in a total volume of 0.5 ml (1 μM sFv) FACS buffer (PBS containing 1% BSA and 0.1% $NaN_3$) for 1 h at 37° C. Cells were washed twice with 10 ml FACS buffer (4° C.) and resuspended in 12 ml FACS buffer and further incubated at 37° C. Aliquots of cells (0.5 ml from 12 ml containing $5\times10^5$ cells) were taken after 5 min, every 15 min for the first hour and after two hours repeating the wash and resuspension cycle. Washed cell aliquots were fixed with 1% paraformaldehyde, washed twice with FACS buffer, and incubated for 15 min at 4° C. with a 1:800 dilution of phycoerythrine-labeled streptavidin (Pierce). Fluorescence was measured by FACS and the percent retained fluorescence on the cell surface plotted versus the time points. Single-chain Fv used for the cell surface retention assay were C6.5 ($K_d$=$1.6\times10^{-8}$ M), C6ML3-9 ($K_d$=$1.0\times10^{-9}$ M), C6MH3-B1 ($K_d$=$1.2\times10^{-10}$ M), and the anti-digoxin sFv 26-10 (Huston et al. (1988) *Proc. Natl. Acad. Sci. USA*, 85: 5879–83) as negative control.

High resolution functional scan of C6. 5 $V_H$ CDR3.

A high resolution functional scan of the C6.5 $V_H$ CDR3 was performed by individually mutating residues 95–99, 100a–100d, and 100g–102 to alanine. The pair of cysteine r esidues (100 and 100e) were sim u ltaneously mutated to serine. Residue 100f (alanine) was not studied. Mutations were introduced by oligonucleotide directed mutagenesis using the method of Kunkel et al. (1987)*Meth. Enzymol.*, 154: 367–82.

Insertion of the correct mutation was verified by DNA sequencing, and sFv was expressed (De Bellis et al. (1990) supra.; Breitling et al. (1991) supra.) and purified by IMAC (Hochuli et al. (1988) supra.). Affinities were determined by SPR as described above and compared to C6.5 sFv.

Modeling of location of mutations.

The location of mutations in mutated sFv was modeled on the structure of the Fab KOL (Marquart et al. (1980) *J. Mol. Biol.*, 141: 369–391) using the program O (Jones et al. (1991). *Acta Cryst.*, A47: 110–119) on a Silicon Graphics workstation.

II. Results

1) Mutation of C6.5 sFv $V_L$ CDR3

Library construction and selection.

As explained above, 9 amino acids in $V_L$ CDR3 were partially randomized by synthesizing a "doped" oligonucleotide in which the wild-type nucleotide occurred with a frequency of 49%. After transformation, a library of $1.0\times10^7$ clones was obtained. The mutant phage antibody library was designated C6VLCDR3.

Polymerase chain reaction (PCR) screening revealed that 100% of clones analyzed had full length insert and diversity was confirmed by sequencing the $V_L$ CDR3 of ten clones from the unselected library. Prior to selection, 5/92 clones selected at random expressed sFv which bound c-erbB-2 ECD by enzyme linked immunosorbent assay (ELISA).

The C6VLCDR3 library was subjected to four rounds of selection using decreasing concentrations of biotinylated c-erbB-2 ECD. A relatively high antigen concentration ($4.0\times10^{-8}$ M) was used for the first round to capture rare or poorly expressed phage antibodies. The concentration was decreased 40 fold for the second round ($1.0\times10^{-9}$ M), and decreased a further tenfold each of the subsequent two rounds ($1.0\times10^{-10}$ M, 3rd round; $1.0\times10^{-11}$ M, 4th round). After each round of selection, the concentration of binding phage in the polyclonal phage preparation was determined by measuring the rate of binding of polyclonal phage to c-erbB-2 ECD under mass transport limited conditions using surface plasmon resonance (SPR) in a BIAcore. The results were used to guide the antigen concentration for the subsequent round of selection. After both the third and fourth rounds of selection, 92/92 clones bound c-erbB-2 ECD by ELISA.

Characterization of mutant sFv.

To identify sFv with a lower $K_d$ than wild-type sFv, apparent $k_{off}$ was determined by SPR in a BIAcore on unpurified native sFv in bacterial periplasm. Twenty-four sFv from the third and fourth rounds of selection were ranked by $k_{off}$. After the third round of selection, 80% of sFv had a lower $k_{off}$ than wt and after four rounds, 100% of sFv had a lower $k_{off}$ than wild-type sFv. The twelve sFv with the lowest $k_{off}$ from each of these rounds of selection were sequenced and each unique sFv gene was subcloned for purification. Single-chain Fv were purified by immobilized metal affinity chromatography (IMAC), followed by gel filtration to remove any dimeric or aggregated sFv.

The $k_{on}$, and $k_{off}$ were determined by BIAcore, and the $K_d$ calculated. After the third round of selection, seven unique sFv were identified, all with higher affinity than wild-type sFv. Single-chain Fv had on average 1.8 amino acid substitutions/sFv, with a single substitution at residue 92 the most frequently observed mutation. These single amino acid substitutions would have occurred with a frequency of 1/12,000 in the original library, assuming equal nucleotide coupling efficiency. The average sFv affinity was $3.6 \times 10^{-9}$ M (4.4 fold increase), with the highest affinity $2.6 \times 10^{-9}$ M (sixfold increase).

After four rounds of selection, six sFv were identified, and none of these sequences were observed in the sFv sequenced from the third round. Single-chain Fv from the fourth round had on average 2.9 amino acid substitutions/sFv, with expected frequencies of between 1/590,000 and 1/24,000,000 in the original library. The average sFv affinity after the fourth round was $1.9 \times 10^{-9}$ M (8.4 fold increase), with the highest affinity $1.0 \times 10^{-9}$ M (16 fold increase). The results demonstrate the efficiency of the selection technique for isolating very rare high affinity clones from a library. Additional high affinity sFv (Table 14; C6ML3-14, -15, -19, -23, and -29) were isolated from the C6VLCDR3 library by using a different elution solution after capture of antigen bound phage.

Location of mutations in higher affinity sFv.

Significant sequence variability (six different amino acids) was observed at residues 93, and 94, with less variability (three different amino acids) at residues 95 and 95a. Thus a subset of the randomized residues appear to be more important in modulating affinity. All but one of these four residues ($V_1L95$) appear to have solvent accessible side chains in the C6.5 model. Three of the residues randomized (A89, W91, and G96) were 100% conserved in all mutants sequenced. Two additional residues (A90S and D92E) showed only a single conservative substitution. These conserved residues appear to have a structural role in the variable domain, either in maintaining the main chain conformation of the loop, or in packing on the $V_H$ domain. Residues A89, W91, and D92 are identical in both C6.5 and KOL, with conservative substitutions A90S and G96A observed at the other two positions in KOL, consistent with a structural role.

In the model of C6.5 indicated by this invention, G95b is in a turn and A89, A90, and W91 pack against the $V_H$ domain at the $V_H$–$V_L$ interface. Hydrogen bonds between $V_1D92$ and $V_1S27a$ and $V_1N27b$ bridge L3 and L1 to stabilize the L3 and L1 conformations.

2) Mutation of C6ML3-9 sFv $V_H$ CDR3

Library construction and selection.

To further increase the affinity of C6.5, we chose to mutate the $V_H$ CDR3 of the highest affinity sFv (C6ML3-9, $K_d = 1.0 \times 10^{-9}$ M) isolated from the C6VLCDR3 library, rather than mutate C6.5 $V_H$ CDR3 independently and combine mutants. This sequential approach was taken since the kinetic effects of independently isolated antibody fragment mutations are frequently not additive (Yang et al. (1995) *J. Mol. Biol.*, 254: 392–403).

Due to the length of the C6.5 $V_H$ CDR3 (20 amino acids), a high resolution functional scan was performed on C6.5 sFv in an attempt to reduce the number of amino acids subjected to mutation. Residues 95–99, 100a-100d, and 100g–102 were separately mutated to alanine, and the $K_d$ of the mutated sFv determined. Residue 100f (alanine) was not studied. Residues 100 and 100e are a pair of cysteines separated by four amino acids. A homologous sequence in KOL (Marquardt et al. (1980) supra.) results in a disulfide bond between the two cysteines and a four residue miniloop. Therefore the two cysteines were simultaneously mutated to serine.

Results of the alanine scan are shown in Table 13. No detectable binding to c-erbB-2 ECD could be measured by BIAcore for C6.5H95A, C6.5W100hA, and C6.5E100jA. Three additional alanine mutants (G98A, Y100kA, and F1001A) yielded sFv with 20 fold to 100 fold higher $K_d$ than wt sFv. Substitution of the two cysteines by alanine (100, 100e) yielded an sFv with an 17.5 fold higher $K_d$, and a much faster $k_{off}$ ($1.38 \times 10^{-1} s^{-1}$) than wt C6.5. The remainder of the alanine substitutions yielded only minor (0.5 to 3.7 fold) increases or decreases in $K_d$.

Based on the results of the alanine scan and a model of C6.5 based on the Fab KOL (Marquardt et al., 1980), residues H95A, C100, and C100e were not mutated due to their probability of having an important structural role. H95 is likely to be buried at the $V_H$–$V_L$ interface where it makes critical packing contacts with the $V_L$ domain. The two cysteine residues also are likely to have a structural role in maintaining the miniloop conformation. W100h was also not mutated given the unique features of tryptophan in antibody combining sites (Mian et al. (1991) *J. Mol. Biol.*, 217: 133–151).

The remaining 16 amino acids were completely randomized four residues at a time in four separate C6VHCDR3 libraries (96–99, library A; 100a–100d, library B; 100f, 100g, 100i, and 100j, library C, and 100k–102, library D; see Table 14). After transformation, libraries were obtained with sizes $1.7 \times 10^7$ (library A), $1.3 \times 10^7$ (library B), $3.0 \times 10^6$ (library C), and $2.4 \times 10^7$ (library D). The mutant phage antibody libraries were designated C6VHCDR3 libraries A, B, C, and D. PCR screening and DNA sequencing

TABLE 13

Binding kinetics of C6.5 $V_H$ CDR3 mutants obtained by high resolutions functional scan. Amino acid residues 95–99, 100a–100d, and 100g–102 of C6.5 $V_H$ CDR3 were mutated to alanine using site directed mutagenesis. Cysteine residues, C100 and C100e, were simultaneously mutated to serine. $k_{on}$ and $k_{off}$ were measured by SPR in a BIAcore, and the $K_d$ calculated. Numbering is according to Kabat et al. (1987). NB = no binding.

| sFv clone | Kd (mutant) / Kd (C6.5) | $K_d$ [$10^{-8}$ M] | $k_{on}$ [$10^5$ M$^{-1}$ s$^{-1}$] | $k_{off}$ [$10^{-2}$ s$^{-1}$] |
|---|---|---|---|---|
| C6.5H95A | NB | NB | NB | NB |
| C6.5D96A | 2.8 | 4.5 | 2.2 ± 0.34 | 1.0 ± 0.02 |
| C6.5V97A | 3.0 | 4.8 | 3.1 ± 0.62 | 1.5 ± 0.02 |
| C6.5G98A | 19.8 | 31.7 | 4.1 ± 0.71 | 13 ± 0.55 |
| C6.5Y99A | 3.7 | 5.9 | 9.0 ± 0.17 | 5.3 ± 0.07 |
| C6.5C100S/C100eS | 17.5 | 28.0 | 5.0 ± 0.25 | 13.8 ± 0.71 |
| C6.5S100aA | 1.8 | 2.8 | 4.7 ± 0.55 | 1.3 ± 0.04 |
| C6.5S100bA | 2.9 | 4.7 | 3.4 ± 0.49 | 1.6 ± 0.07 |
| C6.5S100cA | 1.5 | 2.4 | 4.5 ± 0.62 | 1.1 ± 0.03 |
| C6.5N100dA | 1.8 | 2.9 | 4.1 ± 0.34 | 1.2 ± 0.05 |
| C6.5K100gA | 0.6 | 0.98 | 4.3 ± 0.31 | 0.42 ± 0.01 |
| C6.5W100hA | NB | NB | NB | NB |
| C6.5P100iA | 0.6 | 1.0 | 10.5 ± 0.12 | 1.1 ± 0.02 |
| C6.5E100jA | NB | NB | NB | NB |
| C6.5Y100kA | 101.0 | 161.6 | 0.73 ± 0.07 | 11.8 ± 0.25 |
| C6.5F100lA | 28.4 | 45.4 | 1.1 ± 0.13 | 5.0 ± 0.06 |
| C6.5Q101A | 0.5 | 0.82 | 12.0 ± 0.02 | 0.98 ± 0.02 |
| C6.5H102A | 1.2 | 1.9 | 5.9 ± 0.57 | 1.1 ± 0.02 | revealed that 100% of clones from all four libraries had full length insert and that the sequences were diverse (results not shown). Prior to selection, the percent of clones expressing sFv which bound c-erbB-2 ECD by ELISA was 1% for C6VHCDR3 library A, 57%, library B, 2% library C, and 3% library D. The C6VHCDR3 libraries A, B, C, and D were selected on biotinylated c-erbB-2 ECD as described above, but using lower antigen concentration. The first round of selection was performed using $5.0 \times 10^{-9}$ M c-erbB-2 ECD, tenfold lower than for the first round of Characterization of mutant sFv.

After four rounds of selection, positive clones were identified by ELISA and at least 24 sFv from the fourth round of selection were ranked by $k_{off}$ using SPR in a BIAcore. The ten sFv with the lowest $k_{off}$ from C6VHCDR3 libraries A, C, and D were sequenced.

TABLE 14

Sequences, affinities and binding kinetics of scFv isolated from heavy chain CDR3 libraries A, B, C, and D. $k_{on \text{ and } koff}$ were determined in a BIAcore using purified scFv, and $k_d$ calculated.
Dashes indicate sequence identity. Mutations arising from PCR error and located outside $V_H$ CDR3 are listed under the heading "other mutations". F = frequency of isolated scFv. *$k_{off}$ determined from unpurified scFv samples. Underline indicates mutated residue.

| Clone Name | VH CDR3 sequence | Other Mutations | $K_d$ ($10^{-10}$M) | $K_{off}$ ($10^{-4}s^{-1}$) | SEQ ID NO |
|---|---|---|---|---|---|
| C6.5 | HDVGYCSSSNCAKWPEYFQH | | 1.60 | 63.0 | 61 |
| VH CDR3 library A: | | | | | |
| C6ML3-9 (wt) | —DVGY—————————— | | | | 61 |
| C6ML3-A2 | HDVGFCSSSNCAKWPEYFQH | | | | 66 |
| C6ML3-A3 | HDVGYCSSSDCAKWPEYFQH | | 160.0 | 63.0 | 67 |
| VH CDR3 library B: | | | | | |
| C6ML3-9 (wt) | ————————SSSN————————— | | 10.0 | 7.6 | 61 |
| C6MH3-B1 | HDVGYCTDRTCAKWPEYFQH | | 1.6 | 0.67 | 68 |
| C6MH3-B15 | HDVGYCESSRCAKWPEYFQH | | 7.7 | 2.9 | 69 |
| C6MH3-B11 | HDVGYCSDRSCAKWPEYFQH | | 2.2 | 2.3 | 70 |
| C6MH3-B9 | HDVGYCKTAACAKWPEYFQH | | 8.7 | 3.3 | 71 |
| C6MH3-B8 | HDVGYC*TERCAKWPEYFQH | | 7.2 | 2.9 | 72 |
| C6MH3-B2 | HDVGYCTDPRCAKWPEYFQH | | 3.1 | 3.1 | 73 |
| C6MH3-B39 | HDVGYCTDPTCAKWPEYFQH | | 3.2 | 1.9 | 74 |
| C6MH3-B25 | HDVGYCLTTRCAKWPEYFQH | | 3.6 | 1.9 | 75 |
| C6MH3-B21 | HDVGYCTTPLCAKWPEYFQH | | 7.3 | 2.4 | 76 |
| C6MH3-B20 | HDVGYCSPARCAKWPEYFQH | | 8.7 | 1.6 | 77 |
| C6MH3-B16 | HDVGYCADVRCAKWPEYFQH | | 3.1 | 2.8 | 78 |
| C6MH3-B47 | HDVGYCTDRSCAKWPEYFQH | | 1.1 | 0.75 | 79 |
| C6MH3-B48 | HDVGYCTDPSCAKWPEYFQH | | 2.3 | 1.3 | 80 |
| C6MH3-B5 | HDVGYCTDATCAKWPEYFQH | | 3.4 | 2.3 | 81 |
| C6MH3-B41 | HDVGYCTDRPCAKWPEYFQH | | 5.3 | 2.7 | 82 |
| C6MH3-B2 | HDVGYCTDPRCAKWPEYFQH | | 5.8 | 3.2 | 73 |
| C6MH3-B27 | HDVGYCKNSRCAKWPEYFQH | | 4.7 | 4.0 | 83 |
| C6MH3-B34 | HDVGYCQDTRCAKWPEYFQH | VL Q1R | ND | ND | 84 |
| C6MH3-B43 | HDVGYCEDYTCAKWPEYFQH | | ND | ND | 85 |
| C6MH3-B46 | HDVGYCTTPRCAKWPEYFQH | VH K23Q VH V76G | ND | ND | 86 |
| C6MH3-B33 | HDVGYCSDQTTCAKWPEYFQH | | ND | ND | 87 |
| C6MH3-B31 | HDVGYCDDYTCAKWPEYFQH | VL P7L | ND | ND | 88 |
| VH CDR3 library C: | | | | | |
| C6ML3-9 (wt) | ——————————AKWPE———— | | 10.0 | 7.6 | 61 |
| C6MH3-C4 | HDVGYCSSSNCAVWPEYFQH | | 3.7 | 2.0 | 89 |
| C6MH3-C3 | HDVGYCSSSNCAKWPEYFQH | VH G15E | 6.5 | 3.2 | 61 |
| VH CDR3 library D: | | | | | |
| C6ML3-9 (wt) | HDVGYCSSSNCAKWPEYFQH | | 10.0 | 7.6 | 61 |
| C6MH3-D2 | HDVGYCSSSNCAKWPEWLGV | | 1.6 | 2.0 | 90 |
| C6MH3-D3 | HDVGYCSSSNCAKWPEWLDN | | 2.7 | 2.5 | 91 |
| C6MH3-D6 | HDVGYCSSSNCAKWPEWMYP | | 3.5 | 1.8 | 92 |
| C6MH3-D5 | HDVGYCSSSNCAKWPEWMQM | | 3.8 | 2.1 | 93 |
| C6MH3-D1 | HDVGYCSSSNCAKWPEWLHV | | 3.1 | 1.1 | 94 |
| C6MH3-D7 | HDVGYCSSSNCAKWPEWQDP | | ND | 3.1 | 95 | selection of the C6VLCDR3 library. This concentration was chosen because the parental sFv for these libraries (C6ML3-9) had a greater than tenfold lower $K_d$ than the parental clone for the C6VLCDR3 library (C6.5). Biotinylated c-erbB-2 ECD concentration was then decreased 100 fold for the second round of selection ($5.0 \times 10^{-11}$ M) and tenfold for the third and fourth rounds ($5.0 \times 10^{-12}$ M and $5.0 \times 10^{-13}$ M). As for the C6VLCDR3 library, the rate of binding of polyclonal phage was measured in a BIAcore to determine the antigen concentration used for the subsequent round of selection as discussed below.

Due to the diversity of isolated sFv in C6VHCDR3 library B, 48 sFv were ranked by $k_{off}$ using SPR, and 22 clones with the lowest $k_{off}$ were sequenced. Single-chain Fv were purified by IMAC, followed by gel filtration to remove any dimeric or aggregated sFv. The $K_{on}$, and $k_{off}$ were determined by BIAcore and the $K_d$ calculated.

Very different results were obtained from the four libraries with respect to the number of higher affinity sFv isolated, and the value of the highest affinity sFv. The best results were obtained from library B (Table 14). Fifteen sFv were isolated with a $K_d$ lower than wt C6ML3-9 and no wt sequences were observed (Table 14). The best sFv (C6MH3-B47) had a $K_d$=1.1×10$^{-10}$ M, ninefold lower than C6ML3-9 and 145 fold lower than C6.5. The $k_{off}$ of this sFv was 7.5×10$^{-5}$ s$^{-1}$, tenfold lower than C6ML3-9 and 84 fold lower than C6.5. While a wide range of sequences was observed (Table 14, library B), a subset of sFv had the consensus sequence TDRT (SEQ ID NO:96) (first eight sFv, Table 14). The consensus sequence is identical with the sequence of C6MH3-B1, which is the sFv with the lowest $k_{off}$ (6.0×10$^{-5}$ s$^{-1}$).

Five sFv were isolated that had a $k_{off}$ 2.5 to 3.75 fold lower than C6ML3-9, however expression levels were too low to obtain adequate purified sFv for measurement of the $K_d$ (last five sequences, Table 14, library B). The next best results were obtained from library D (Table 14). Five higher affinity sFv were isolated, with the best having a $K_d$ sevenfold higher than wt C6ML3-9. An additional sFv was isolated that had a $k_{off}$ lower than wt sFv, however the expression level was too low to obtain adequate purified sFv for measurement of the $K_d$ (last sequence, Table 14, library D). There was selection for a consensus mutation of Y100kW and replacement of F1001 with hydrophobic methionine or leucine. No higher affinity sFv were isolated from either the A or C libraries. From library A, 8/10 sFv were wild-type, with one higher affinity sFv, a contaminant from library B. A single mutant sFv with the conservative replacement of Y99F had an apparent $k_{off}$ 2.5 times lower than wt, but expression levels were too low to obtain adequate purified sFv to measure the $K_d$. From library C, 8/10 sFv were wt sFv, with one higher affinity sFv having mutations located in the $V_H$ and $V_L$ genes, but not in the region intentionally mutated. The isolated mutant sFv K100gV had a $K_d$ 2.7 fold lower than wt ($k_{off}$ 3.8 fold lower than C6ML3-9), correlating with the data of the alanine scan, in which K100gA was the only sFv with decreased $k_{off}$.

Ability of alanine scanning to identify residues which modulated affinity.

Residue E100j, the only residue that when converted to alanine had no detectable binding, was 100% conserved. Otherwise, there was no correlation between the frequency with which the wt amino acid was recovered and the extent to which binding was reduced by substitution to alanine. Similarly, there was no correlation between residues shown to modulate affinity by alanine scanning and mutations exhibiting improved binding. This is clear when comparing the results obtained from library B (where no alanine mutant had more than a 2.9 fold increase in $K_d$) and library D (where $K_d$ was markedly increased for two alanine mutants, Y100kA and F1001A). Despite the different alanine scan results, both libraries yielded similar nine and sevenfold increases in affinity. This result appears to be different than the results of Lowman et al. (1993) *J. Mol. Biol.*, 234: 564–578, who found a mild ($R^2$=0.71) positive correlation between the frequency with which the wt amino acid was recovered from a phage library of human growth hormone mutants and the extent to which binding was reduced by alanine scanning. In addition, their largest improvements in affinity were for those residues shown by alanine scanning to significantly affect binding.

The reason for the different results is unclear, however in two of the $V_H$ CDR3 libraries where alanine scanning indicated a significant effect on binding (libraries A and C), expression levels of mutants were generally low. This could have affected the selection results.

3) Correlation between affinity and cell surface retention of sFv.

The retention of biotinylated C6.5, C6ML3-9, and C6MH3-B1 sFv on the surface of SK-OV-3 cells expressing c-erbB-2 was determined, both to verify the observed differences in $k_{off}$, and to confirm that the antigen as presented in the BIAcore had biologic significance. The half life ($t_{1/2}$) of the sFv on the cell surface was much less than 5 min for C6.5, 11 min for C6ML3-9, and 102 min for C6MH3-B1. These values agree closely with the $t_{1/2}$ calculated from the $k_{off}$ as determined by SPR in a BIAcore (1.6 min for C6.5, 13 min for C6ML3-9, and 135 min for C6MH3-B1). The anti-digoxin sFv 26-10 (Huston et al. (1988) supra.) was used as negative control, and no binding to c-erbB-2 ECD in a BIAcore or to c-erbB-2 on SK-OV-3 cells was observed.

Example 4

Elution of Antibodies

As higher affinity phage antibodies are generated, it becomes more difficult to elute them from c-erbB-2. Selection of the highest affinity mutants is enhanced when elution conditions are optimized. To determine optimal elution conditions, the C6.5 V1 CDR3 mutant library was selected on c-erbB-2, and a number of different elution conditions studied (infecting directly off of magnetic beads, 10 mM HCl, 50 mM HCl, 100 mM HCl, 2.6 M MgCl$_2$, 4 M MgCl$_2$, 100 mM TDA, and with 1 μM c-erbB-2). The greatest percentage of clones with a $k_{off}$ slower than C6.5 was obtained when eluting with 50 mM HCl, 100 mM HCl, or 4 M MgCl$_2$. Even after the eluted clones were screened by BIAcore to identify those with the slowest $k_{off}$, the highest affinity clones resulted from elutions performed with 100 mM HCl as shown in Table 15 (in this experiment 4 mM MgCl$_2$ was not examined).

These results correlated with the amount of phage antibody library that remained bound in the BIAcore after using one of the different elution conditions. For the $V_H$ CDR3 elutions phage were eluted sequentially with 4 mM MgCl$_2$ and 100 mM HCl. As affinity increases urther more stringent elution conditions may be required. This can be determined by analyzing phage libraries in the BIAcore.

TABLE 15

Results of C6.5 L3 randomization 4th round off-rate selection and elution. Underlines indicate mutated amino acids.

| Clones | F | $V_H$ CDR3 Sequence | $K_d$ (M) | $K_{off}$ (s$^{-1}$) | SEQ ID NO: |
|---|---|---|---|---|---|
| C6.5 | | AAWDDSLSGWV | $1.6 \times 10^{-8}$ | $6.3 \times 10^{-3}$ | 6 |
| Elution with 100 mM HCl: | | | | | |
| C6ML3-5 | 4 | AAWDYSLSGWV | $3.7 \times 10^{-9}$ | $6.3 \times 10^{-3}$ | 7 |
| C6ML3-9 | | ASWDYTLSGWV | $1.0 \times 10^{-9}$ | $1.9 \times 10^{-4}$ | 15 |
| C6ML3-14 | 2 | AAWDDPLWGWV | $1.1 \times 10^{-9}$ | $7.6 \times 10^{-4}$ | 24 |
| C6ML3-15 | | AAWDRPLWGWV | $2.2 \times 10^{-9}$ | $7.7 \times 10^{-3}$ | 23 |
| Elution with 2.6 M MgCl$_2$: | | | | | |
| C6ML3-5 | 2 | AAWDYSLSGWV | $3.7 \times 10^{-9}$ | $1.9 \times 10^{-3}$ | 7 |
| C6ML3-7 | 2 | AAWDYAVSGWV | $2.6 \times 10^{-9}$ | $1.7 \times 10^{-3}$ | 12 |
| C6ML3-12 | | AAWDYSRSGWV | $1.6 \times 10^{-9}$ | $7.2 \times 10^{-4}$ | 14 |
| C6ML3-16 | 2 | ASWDYYRSGWV | $5.0 \times 10^{-9}$ | $1.7 \times 10^{-3}$ | 97 |
| C6ML3-15 | | AAWDRPLWGWV | $2.2 \times 10^{-9}$ | $1.3 \times 10^{-3}$ | 23 |
| Elution with 100 mM triethylamine: | | | | | |
| C6ML3-5 | 3 | AAWDYSLSGWV | $3.7 \times 10^{-9}$ | $1.9 \times 10^{-3}$ | 7 |
| C6ML3-12 | 2 | AAWDYSRSGWV | $1.6 \times 10^{-9}$ | $7.2 \times 10^{-4}$ | 14 |
| C6ML3-18 | | ASWDASLWDWV | $2.4 \times 10^{-9}$ | $6.2 \times 10^{-4}$ | 98 |
| C6ML3-19 | | ASWDRPLWGWV | $1.5 \times 10^{-9}$ | $1.0 \times 10^{-3}$ | 21 |
| C6ML3-20 | | AAWEQSLWGWV | $3.0 \times 10^{-9}$ | $1.4 \times 10^{-3}$ | 99 |
| Elution with 10 mM HCl: | | | | | |
| C6ML3-5 | | AAWDYSLSGWV | $3.7 \times 10^{-9}$ | $1.9 \times 10^{-3}$ | 7 |
| C6ML3-7 | | AAWDYAVSGWV | $2.6 \times 10^{-9}$ | $1.7 \times 10^{-3}$ | 12 |
| C6ML3-21 | | AAWDYSQSGWV | $4.5 \times 10^{-9}$ | $2.2 \times 10^{-3}$ | 100 |
| C6ML3-22 | | AAWDASLSGWV | $8.3 \times 10^{-9}$ | $3.6 \times 10^{-3}$ | 101 |
| C6ML3-23 | | ASWDHSLWGWV | $1.5 \times 10^{-9}$ | $1.0 \times 10^{-3}$ | 20 |
| C6ML3-24 | | AAWDEQIFGWV | $12.4 \times 10^{-9}$ | $7.9 \times 10^{-3}$ | 102 |
| C6ML3-25 | | AAWDNRHSGWV | $7.4 \times 10^{-9}$ | $4.4 \times 10^{-3}$ | 103 |
| C6ML3-26 | | AAWDDSRSGWV | $8.3 \times 10^{-9}$ | $5.0 \times 10^{-3}$ | 104 |
| Elution with 50 mM HCl: | | | | | |
| C6ML3-6 | | ASWDYSLSGWV | $3.2 \times 10^{-9}$ | $1.9 \times 10^{-3}$ | 9 |
| C6ML3-7 | | AAWDYAVSGWV | $2.6 \times 10^{-9}$ | $1.7 \times 10^{-3}$ | 12 |
| C6ML3-12 | | AAWDYSRSGWV | $1.6 \times 10^{-9}$ | $7.2 \times 10^{-4}$ | 14 |
| C6ML3-17 | | ASWDYYRSGWV | $5.0 \times 10^{-9}$ | $1.7 \times 10^{-3}$ | 105 |
| C6ML3-27 | | TAWDYSLSGWV | no expression | | 106 |
| C6ML3-28 | | ASWDYALSGWV | $2.5 \times 10^{-9}$ | $1.7 \times 10^{-3}$ | 107 |
| C6ML3-29 | | AAWDGTLWGWV | $1.7 \times 10^{-9}$ | $2.2 \times 10^{-3}$ | 22 |
| Elution with 1 µM c-erbB-2 ECD for 30 minutes | | | | | |
| C6ML3-5 | 5 | AAWDYSLSGWV | $3.7 \times 10^{-9}$ | $1.9 \times 10^{-3}$ | 7 |
| C6ML3-17 | | AAWDYALSGWV | no expression | | 108 |
| C6ML3-30 | 3 | ASWDYYLIGWV | no expression | | 109 |

For example, in a second experiment, polyclonal phage were prepared after three rounds of selection of the C6VLCDR3 library and studied using SPR in a BIAcore. After an initial bulk refractive index change, binding of phage to immobilized c-erbB-2 ECD was observed, resulting in an average of 189 RU bound. Phage were then allowed to either spontaneously dissociate from c-erbB-2 ECD using hepes buffered saline (HBS) as running buffer, or were eluted with either 100 mM HCl, 50 mM HCl, 10 mM HCl, 2.6 M MgCl$_2$, or 100 mM TEA.

Major differences were observed between eluents in their ability to remove bound phage. The most effective solutions in removing bound phage antibodies were 100 mM HCl and 50 mM HCl, followed by 100 mM TEA. 2.6 M MgCl$_2$ (which removes 100% of wild type C6.5) and 10 mM HCl were only minimally more effective than the running buffer in removing bound phage.

These results demonstrate the important effect of eluent choice on the affinities of selected antibodies, even when using limiting antigen concentration and BIAcore screening to identify the highest affinity sFv. Two previously described elution regimens were found to be the least effective for selecting higher affinity antibodies; infecting without elution by adding magnetic beads with antigen-bound phage directly to E. coli cultures (Figini et al. (1994) J. Mol. Biol., 239: 68) and competitive elution of sFv with soluble antigen (Hawkins et al. (1992) J. Mol. Biol., 226: 889; Clackson et al. (1991) Nature, 352: 624; Riechmann et al. (1993) Biochemistry, 32: 8848).

When eluting by incubating phage bound to antigen with E. coli, it is believed the phage must dissociate from antigen for infection to occur. Steric hindrance, due to the size of paramagnetic beads, blocks the attachment of pill on antigen bound phage to the f-pilus on E. coli. This would result in preferential selection of sFv with rapid $k_{off}$, consistent with the present results. Since a reduction in $k_{off}$ is the major mechanism for decreases in $K_d$, this results in the selection of lower affinity sFv.

Eluting with soluble antigen has a similar effect on the kinetics of selected sFv. The phage must first dissociate from immobilized antigen, then rebinding is blocked by binding of the phage to soluble antigen. Phage antibodies with the lowest $k_{off}$ will remain bound to immobilized antigen and therefore are not available for infection of E. coli.

The optimal type of eluent (acidic, basic, chaotropic) and concentration required will depend on the phage antibody affinity (Lewis et al. (1985) J. Steroid. Biochem. 22: 387; Parini et al. (1995) Analyst, 120: 1153) and the type of bonds that need to be interrupted. This will vary considerably between libraries, depending on the nature of the antigen-antibody interaction.

In this example, significantly higher affinity sFv were obtained eluting with HCl, pH 1.3 compared to HCl, pH 2.0. In fact, the affinities of sFv isolated after elution with HCl, pH 2.0 were no different than results obtained without eluting. Similarly, 2.6 M $MgCl_2$ was studied because it was previously determined (see above) that it would remove 100% of bound wild type C6.5. This concentration of $MgCl_2$, however, was ineffective in eluting C6.5 $V_L$ CDR3 mutants. Eluting with higher concentrations of $MgCl_2$ would have resulted in the selection of higher affinity sFv. For example, 3 M $MgCl_2$ was required to elute 100% of C6L1 sFv ($K_d$=2.5×10$^{-9}$ M) from a c-erbB-2 ECD BIAcore sensor chip and 4 M $MgCl_2$ was required to elute 100% of C6ML3-9 ($K_d$=1.0×10$^{-9}$ M).

A convenient way to predict the optimal eluent is to analyze polyclonal phage in a BIAcore. The results can then be used to design elution conditions to achieve optimal enrichment for high affinity clones. One approach is to elute sequentially, using a less stringent eluent to remove low affinity binders, followed by a more stringent eluent to remove high affinity binders. Thus the BIAcore information is used to select 'washing' reagents which remove low affinity phage antibodies more effectively than PBS. This will reduce the number of selection rounds and amount of screening required to select and identify the highest affinity binders.

This strategy is also be useful to isolate antibodies to low density antigens on intact cells or tissue. A mild eluent could be used to remove low affinity phage antibodies, which are preferentially selected due to high density antigen present on the cell surface, as well as non-specifically bound phage. Phage specific for lower density antigens would then be removed using a more stringent solution.

An alternative to eluting with stringent solutions is to use antigen biotinylated with NHS-SS-Biotin (Pierce) (Griffiths et al. (1994) EMBO J., 13: 3245). All of the bound phage can be released from the magnetic beads by reducing the disulfide bond between antigen and biotin. One advantage of this approach is that elution of all phage is guaranteed. Use of NHS-SS-Biotin could be combined with use of a milder eluent for washing (determined by BIAcore analysis) to increase enrichment for higher affinity phage antibodies.

The present experiments suggest, however, that use of stringent eluents that are chemically different (acidic, basic, or chaotropic) results in the selection of sFv of equally high affinity, but of different sequence. Isolation of sFv of different sequences has a number of advantages. Single amino acid changes can affect expression levels in E. coli dramatically. For example, expression level of C6ML3-5 (100 μg/L) was 100 times less than for wild type C6.5 (10 mg/L). Furthermore, different sFv might have different physico-chemical characteristics (dimerization, stability, or immunoreactivity) or even different effects in vivo (specificity, biodistribution, or clearance). Thus parallel selections using different stringent eluents should result in a greater number of high affinity binders than use of a single eluent.

Example 5

Production of Antibodies Combining C6MH3-B1 or C6MH3-B47 with D Library (YFQH) (SEQ Id NO:65) Mutations I. Methods.

Construction of sFv combining higher affinity $V_H$ and $V_L$ genes.

The $V_L$ CDR3 gene sequences of the two highest affinity sFv isolated from the C6VLCDR3 library (C6ML3-9 or C6ML3-12) were combined with the highest affinity sFv previously obtained from light chain shuffling (C6L1, $K_d$=2.5×10$^{-9}$ M). The C6L1 plasmid (10 ng/μl) was used as a template for PCR amplification using primers LMB3 and either PML3-9 or PML3-12 (Table 18). The gel purified PCR fragments were reamplified using primers LMB3 and HUJ1 2-3ForNot (Marks et al. (1991) supra.) to introduce a NotI restriction site at the 3'-end of the sFv. The gel purified PCR fragments were digested with NcoI and NotI and ligated into pUC119 Sfi-NotmycHis digested with NcoI and NotI. The resulting sFv were designated C6-9L1 and C6-12L1. The $V_L$ genes of C6-9L1 and C6-12L1 were combined with the $V_H$ genes of the two highest affinity sFv from the C6VHCDR3 libraries (C6MH3-B1 and C6MH3-B47). The rearranged $V_H$ genes of C6MH3-B1 and -B47 were amplified by PCR using the primer LMB3 and PC6VH1FOR, digested with NcoI and XhoI (located in FR4 of the heavy chain) and ligated into C6-9L1 or C6-12L1 digested with NcoI and XhoI to create C6-B1L1 and C6-B47L1. The heavy chain of C6MH3-B1 or C6MH3-B47 was amplified by PCR using LMB3 and one of the PCD primer (PCD1, PCD2, PCD3, PCD5, or PCD6; Table 18) to construct combinations of sFv from the C6VHCDR3B and D libraries. The purified PCR fragments were spliced with the $V_L$ fragment of C6ML3-9 (VHD2) that was used to create the C6VHCDR3D library exactly as described above. The full length sFv gene was digested with NcoI and NotI and ligated into pUC119 Sfi-NotmycHis. Clones were termed C6-B1D1, -B1D2, -B1D3, -B1D5, -B1D6, -B47D1, -B47D2, -B47D3, -B47D5, and -B47D6. Colonies were screened for the presence of the correct insert by PCR fingerprinting and confirmed by DNA sequencing. Single-chain Fv were expressed, purified, and affinities determined by SPR, as described above.

II. Results.

Effects on binding kinetics by combining mutations from high affinity sFv.

As described above, to further increase affinity, the sequences of the two highest affinity sFv obtained from the VH CDR3B library (C6MH3-B1 or C6MH3-B47) were combined with the sequences of sFv isolated from the C6VHCDR3D library (C6MH3-D1, -D2, -D3, -D5, or -D6). An increase in affinity from wild-type was obtained for all these combinations, yielding an sFv (C6-B1D3) that had a 1230 fold lower $K_d$ than wt C6.5 (Table 16). The extent of additivity varied considerably, however, and could not be predicted from the parental $k_{on}$, $k_{off}$, or $K_d$. In some combinations, cooperativity was observed, with a negative $\Delta\Delta G_I$. Additional combinations were made between a previously described light chain shuffled C6.5 mutant (C6L1, sixfold decreased $K_d$) and one of two $V_L$ CDR3 mutants (C6ML3-9 and C6ML3-12). These combinations yielded sFv with 49 and 84 fold improved affinity (Table 16). Introducing the same rearranged $V_L$ gene into the highest affinity $V_H$ CDR3 mutants (C6MH3-B1 or C6MH3-B47) resulted in decreased affinity compared to C6MH3-B1 (Table 5).

TABLE 16

Binding kinetics of sFv derived from C6.5 $V_L$ CDR3 and $V_H$ CDR3 mutants. Mutants obtained by combining mutations of C6MH3-B1 or C6MH3-B47 with mutations from D library clones (D1, D2, D3, D5, D6). Rate constants $k_{on}$, and $k_{off}$ were measured by SPR in a BIAcore, and the $K_d$ calculated.

| Clone | $K_d$ [$10^{-10}$ M] | $k_{on}$ [$10^5$ s$^{-1}$ M$^{-1}$] | $k_{off}$ [$10^{-4}$ s$^{-1}$] | $K_d$ (parent) $K_d$ (mut) | $K_d$ (C6.5) $K_d$ (mut) | $\Delta\Delta G_I$ [kcal/mol] |
|---|---|---|---|---|---|---|
| A. Combined mutants: C6ML3–9 or C6ML3–12 with light chain shuffled C6L1: | | | | | | |
| C6-9L1 | 3.3 | 9.2 ± 0.20 | 3.0 ± 0.40 | 3.0 | 49 | +0.42 |
| C6-12L1 | 1.9 | 6.7 ± 0.12 | 1.3 ± 0.32 | 8.4 | 84 | −0.18 |
| B. Combined mutants: C6MH3-B1 or C6MH3-B47 with light chain shuffled C6L1: | | | | | | |
| C6-B1L1 | 6.3 | 3.8 ± 0.19 | 2.4 ± 0.01 | 0.19 | 25 | +0.43 |
| C6-B47L1 | 6.0 | 3.0 ± 0.16 | 1.8 ± 0.01 | 0.18 | 27 | +0.45 |
| C. Combined mutants: C6MH3-B1 or C6MH3-B47 with D library mutants: | | | | | | |
| C6-B1D1 | 0.32 | 4.7 ± 0.31 | 0.15 ± 0.005 | 3.8 | 500 | −0.61 |
| C6-B1D2 | 0.15 | 6.9 ± 0.42 | 0.10 ± 0.014 | 8.0 | 1067 | −0.07 |
| C6-B1D3 | 0.13 | 6.4 ± 0.20 | 0.08 ± 0.002 | 9.2 | 1231 | −0.53 |
| C6-B1D5 | 0.35 | 5.1 ± 0.36 | 0.18 ± 0.001 | 3.4 | 457 | −0.40 |
| C6-B1D6 | 0.32 | 4.1 ± 0.17 | 0.13 ± 0.002 | 3.8 | 500 | −0.16 |
| C6-B47D1 | 0.68 | 7.1 ± 0.95 | 0.48 ± 0.001 | 1.6 | 235 | −0.11 |
| C6-B47D2 | 0.44 | 9.8 ± 0.72 | 0.43 ± 0.001 | 2.5 | 364 | +0.62 |
| C6-B47D3 | 0.48 | 6.6 ± 0.26 | 0.32 ± 0.001 | 2.3 | 333 | +0.29 |
| C6-B47D5 | 0.63 | 6.2 ± 0.31 | 0.39 ± 0.002 | 1.7 | 254 | −0.01 |
| C6-B47D6 | 0.51 | 5.9 ± 0.30 | 0.30 ± 0.001 | 2.2 | 314 | +0.17 |

Example 6

Production of C6.5-Based Diabodies.

To improve tumor retention sFv dimers (sFv')$_2$ were created as described above by introducing a free cysteine at the C-terminus of the sFv. The dimer had a 40 fold improved affinity compared to the monomer ($K_d$=4.0×10$^{-10}$ M). However, evaluation of the C6.5 (sFv')$_2$ in vivo, showed no significantly improved tumor retention at 24 hours. Without being bound to a theory, it is believed that the disulfide bond is being reduced in vivo, yielding monomeric sFv.

To obtain a stable molecule for evaluation in vivo, a C6.5 diabody (also a (sFv)$_2$) was produced without introducing a cysteine and crosslinking. Instead, the diabody was produced as described in Holliger et al., Proc. Natl. Acad. Sci. USA., 90: 6444–6448 (1993) (see also WO 94/13804). To produce the C6.5 diabody, the peptide linker sequence between the $V_H$ and $V_L$ domains was shortened from 15 amino acids to 5 amino acids. This was done at the genetic level. Synthetic oligonucleotides encoding the 5 amino acid linker (Gly$_4$Ser) (SEQ ID NO:25) were used to PCR amplify the C6.5 $V_H$ and $V_L$ genes, which were then spliced together to create the C6.5 diabody gene. The diabody gene was cloned into pUC119mycHis, the diabody expressed, and purified by IMAC followed by gel filtration as described above.

The affinity of the diabody was measured using surface plasmon resonance in a BIAcore and found to be 4.2×10$^{-10}$ M, with a $k_{off}$ of 3.2×10$^{-4}$ s$^{-1}$. The retention of the FITC labeled diabody on the surface of c-erbB-2 expressing cells was determined by FACS. After 180 minutes, 77% was still retained on the cell surface. Assuming an exponential decay for binding, this value for cell surface retention correlates with a $k_{off}$ of 7×10$^{-5}$ s$^{-1}$. This is significantly slower than the $k_{off}$ measured on the BIAcore, and suggests that c-erbB-2 density is higher on the cell surface than the density used for the BIAcore measurements.

Figure 4:
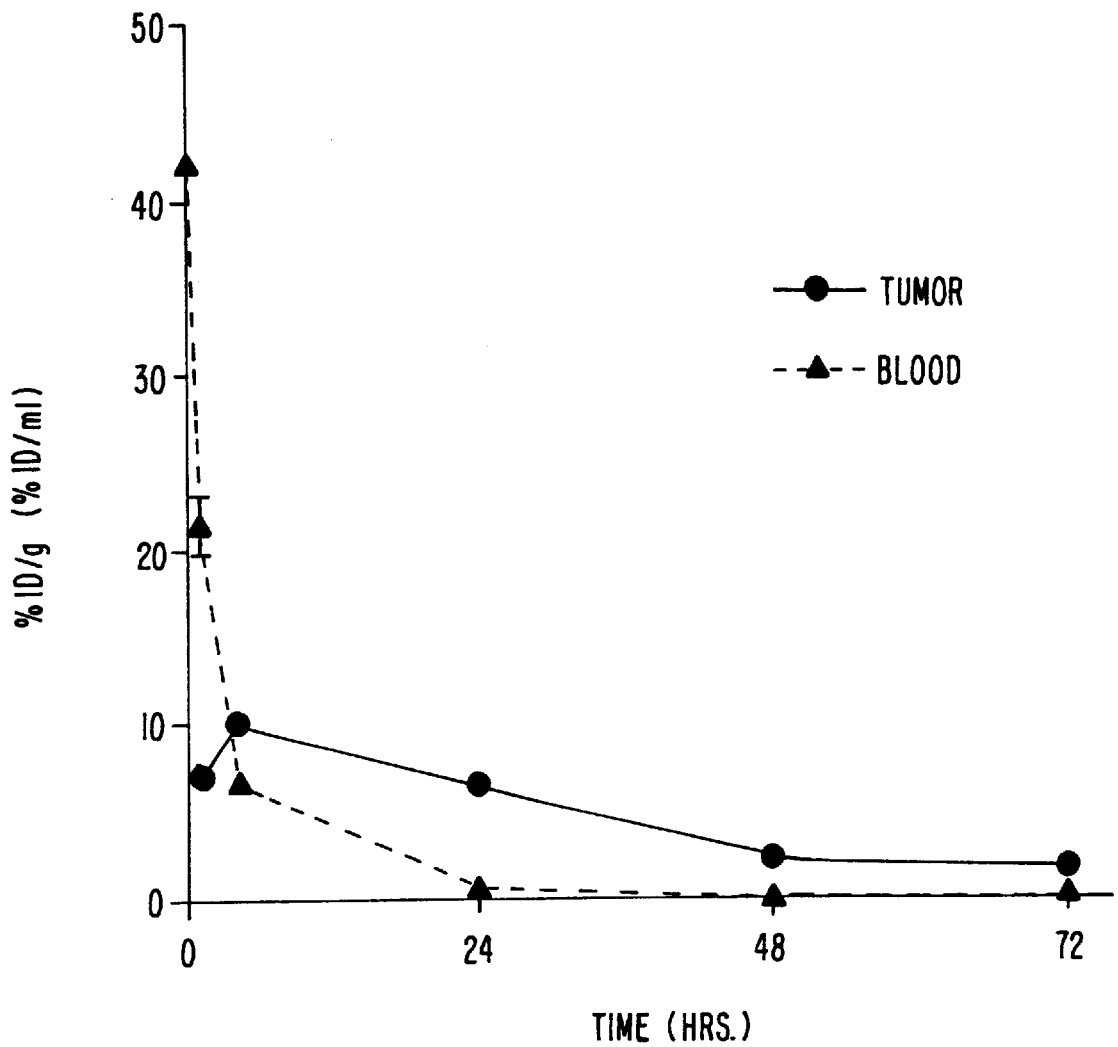
FIG. 4 illustrates the 72 hour biodistribution of a C6.5 diabody in SK-OV-3 tumor-bearing scid mice.

The retention of the C6.5 diabody in scid mice bearing subcutaneous SK-OV-3 tumors was compared to C6.5. Single chain Fv were radio-iodinated using the chloramine-T method, and 25 μg injected into mice. Values are shown in Table 17 and plotted in FIG. 4. At 24 hours, tumor retention was 6.48% of the injected dose/gm of tumor, compared to 0.98% for C6.5. Tumor:blood ratios were 9.7:1 for the diabody and 19.6:1 for the C6.5 sFv. Significant amounts (1.41%) of the diabody was retained at 72 hours. The total area under the curve (AUC) for tumor: blood was 2.3:1.

The ability of the C6.5 diabody to be internalized into c-erbB-2 expressing cells was compared to C6.5 sFv and higher affinity C6.5 mutants. Only the diabody was internalized, consistent with studies using monoclonal antibodies to c-erbB-2 which show that crosslinking of c-erbB-2 results in internalization. This does not occur with all anti-c-erbB-2 antibodies, but rather is epitope dependent. Thus C6.5 recognizes an internalizing epitope, but internalization only results when the receptor is crosslinked by the diabody. This opens up the possibility of creating diabody-toxin fusions (since toxins must be internalized to be active). It is believed that C6.5 also causes signalling through c-erbB-2 via cross-linking of the receptor and activation of the tyrosine kinase activity. It has been shown that activation of the cell through c-erbB-2 signalling increases the sensitivity of the cell to conventional cancer chemotherapeutics. Through activation of the kinase, C6.5 is expected to have therapeutic properties when combined with a conventional cancer chemotherapeutic.

TABLE 17

Tissue distribution of diabody as a function of time.

| Time (Hrs) | Tumor mean ± se | Blood mean ± se | C6.5 Tumor mean ± se | C6.5 Blood mean ± se |
|---|---|---|---|---|
| 0.08 |  | 42.08 ± 0.77 |  |  |
| 1 | 6.93 ± 0.39 | 21.47 ± 1.67 |  |  |
| 4 | 10.06 ± 0.63 | 6.73 ± 0.29 | 0.98 ± 0.08 | 0.05 ± 0.001 |
| 24 | 6.48 ± 0.77 | 0.67 ± 0.05 |  |  |
| 48 | 2.42 ± 0.18 | 0.11 ± 0.01 |  |  |
| 72 | 1.41 ± 0.13 | 0.06 ± 0 |  |  |

TABLE 18

Sequences of primers used in the foregoing examples. Nucleotide mixtures used, molar fraction:
1: A (0.7), C, G, and T (0.1); 2: C (0.7), A, G, and T (0.1); 3: G (0.7), A, T, and C (0.1); 4: T (0.7), A, C, and G (0.1); 5: C and G (0.5); 6: C (0.7) and G (0.3); 7: C (0.3) and 3: G (0.7), A, T, and C (0.1); 8: A, C, G, and T (0.25).

| Primer | Sequence | SEQ ID NO. |
|---|---|---|
| LMB3 | 5'-CAGGAAACAGCTATGAC-3' | 110 |
| fd-seq1 | 5'-GAATTTTCTGTATGAGG-3' | 111 |
| PHEN=1seq | 5'-CTATGCGGCCCCATTCA-3' | 112 |
| Linkseq | 5'-CGATCCGCCACCGCCAGAG-3' | 113 |
| PVH1For1 | 5'-TCGCGCGCAGTAATACACGGCCGTGTC-3' | 114 |
| PVH3For1 | 5'-TCGCGCGCAGTAATACACAGCCGTGTCCTC-3' | 115 |
| PVH5For1 | 5'-TCGCGCGCAGTAATACATGGCGGTGTCCGA-3' | 116 |
| PVH1For2 | 5'-GAGTCATTCTCGACTTGCGGCCGCTCGCGCGCAGTAATACACGGCCGTGTC-3' | 117 |
| PVH3For2 | 5'-GAGTCATTCTCGACTTGCGGCCGCTCGCGCGCAGTAATACACAGCCGTGTCCTC-3' | 118 |
| PVH5For2 | 5'-GAGTCATTCTCGACTTGCGGCCGCTCGCGCGCAGTAATACATGGCGGTGTCCGA-3' | 119 |
| PC6VL1back | 5'-AGCGCCGTGTATTTTTGCGCGCGACATGACGTGGGATATTGC-3' | 120 |
| RJH1/2/6Xho | 5'-ACCCTGGTCACCGTCTCGAGTGGTGGA-3' | 121 |
| RJH3Xho | 5'-ACAATGGTCACCGTCTCGAGTGGTGGA-3' | 122 |
| RJH4/5Xho | 5'-ACCCTGGTCACCGTCTCGAGTGGTGGA-3' | 121 |
| PC6VH1For | 5'-GAGTCATTCTCGTCTCGAGACGGTGACCAGGGTGCC-3' | 123 |
| VL1 | 5'-GTCCCTCCGCCGAACACCCA,5,2,2,5,3,1,6,1,3,5,3,1,7,4,2,7,4,2,2,2,1,5,3,2,5,3,2,ACAGTAAT AATCAGCCTCAT-3' | 124 |
| VL2 | 5'-GAGTCATTCTCGACTTGCGGCCGCACCTAGGACGGTCAGCTTGGTCCCTCCGCCGAACACCGA-3' | 125 |
| VHA | 5'-GCGCAGTTGGAACTACTGCA,5,8,8,5,8,8,5,8,8,5,8,8,ATGTCTCGCACAAAAATACACGGC-3' | 126 |
| RVHA | 5'-TGCAGTAGTTCCAACTGCGC-3' | 127 |
| VHB | 5'-GTATTCAGGCCACTTTGCGCA,5,8,8,5,8,8,5,8,8,5,8,8,GCAATATCCCACGTCATGTC-3' | 128 |
| RVHB | 5'-TGCGCAAAGTGGCCTGAATAC-3' | 129 |
| VHC | 5'-CTGGCCCCAATGCTGGAAGTA,5,8,8,5,8,8,CCA,5,8,8,5,8,8,GCAGTTGGAACTACTGCAATATCC-3' | 130 |

TABLE 18-continued

Sequences of primers used in the foregoing examples. Nucleotide mixtures used, molar fraction:
1: A (0.7), C, G, and T (0.1); 2: C (0.7), A, G, and T (0.1); 3: G (0.7), A, T, and C (0.1); 4: T (0.7), A, C, and G (0.1); 5: C and G (0.5); 6: C (0.7) and G (0.3); 7: C (0.3) and 3: G (0.7), A, T, and C (0.1); 8: A, C, G, and T (0.25).

| Primer | Sequence | SEQ ID NO. |
| --- | --- | --- |
| RVHC | 5'-TACTTCCAGCATTGGGGCCAG-3' | 131 |
| VHD | 5'-GACCAGGGTGCCCTGGCCCCA,5,8,8,5,8,8,5,8,8,5,8,8,TTCAGGCCACTTTGCGCAGTTGG-3' | 132 |
| RVHD | 5'-TGGGGCCAGGGCACCCTGGTC-3' | 133 |
| C6hisnot | 5'-GATACGGCACCGGCGCACCTGCGGCCGCATGGTGATGATGGTGATGTGCGGCACCTAGGACGGTCAGCTTGG-3' | 134 |
| PML3-9 | 5'-CCTAGGACGGTCAGCTTGGTCCCTCCGCCGAACACCCAACCACTCAGGGTGTAATCCCAGGATGCACAGTAATAATCAGC-3' | 135 |
| PML3-12 | 5'-CCTAGGACGGTCAGCTTGGTCCCTCCGCCGAACACCCAACCACTCCGGCTGTAATCCCATGCTGCACAG-3' | 136 |
| PCD1 | 5'-GACGGTGACCAGGGTGCCCTGGCCCCAAACGTGCAGCCATTCAGGCCACTTTGCGCA-3' | 137 |
| PCD2 | 5'-GACGGTGACCAGGGTGCCCTGGCCCCATACGCCCAGCCATTCAGGCCACTTTGCGCA-3' | 138 |
| PCD3 | 5'-GACGGTGACCAGGGTGCCCTGGCCCCAGTTGTCCAACCATTCAGGCCACTTTGCGCA-3' | 139 |
| PCD5 | 5'-GACGGTGACCAGGGTGCCCTGGCCCCACATCTGCATCCATTCAGGCCACTTTGCGCA-3' | 140 |
| PCD6 | 5'-GACGGTGACCAGGGTGCCCTGGCCCCAGGGGTACATCCATTCAGGCCACTTTGCGCA-3' | 141 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference.

What is claimed is:

1. An isolated human antibody that specifically binds to c-erbB-2, said antibody being a C6 antibody, wherein said C6 antibody has the variable heavy ($V_H$) chain of C6.5 (SEQ ID NO. 32) or the variable light ($V_L$) chain of C6.5 (SEO ID NO. 36).

2. The antibody of claim 1, wherein said antibody has the variable heavy ($V_H$) chain of C6.5 (SEQ ID NO. 32).

3. The antibody of claim 1, wherein said antibody has the variable light ($V_L$) chain of C6.5 (SEQ ID NO. 36).

4. The antibody of claim 1, wherein said antibody has the amino acid sequence of C6.5 ($V_H$ SEQ ID NO. 32 linked to $V_L$ SEQ ID NO.36).

5. The antibody of claim 1, wherein said antibody has the amino acid sequence of C6ML3-14 ($V_H$ SEQ ID NO. 43 linked to $V_L$ SEQ ID NO. 36 where $V_L$ CDR3, residues 90–100 of SEQ ID NO. 36 are substituted with SEQ ID NO. 24).

6. The antibody of claim 1, wherein said antibody has the amino acid sequence of C6L1 (SEQ ID NO. 43).

7. The antibody of claim 1, wherein said antibody has the amino acid sequence of C6MH3-B1 ($V_H$ SEQ ID NO. 32 linked to $V_L$ SEO ID NO. 36 where $V_H$ CDR3, residues 99–118 of SEQ ID NO. 32 are substituted with SEQ ID NO. 68).

8. The antibody of claim 1, wherein said antibody has the amino acid sequence of C6ML3-9 ($V_H$ SEO ID NO. 32 linked to $V_L$ SEQ ID NO. 36 where $V_H$ CR3 residues 99–118 of SEO ID NO. 32 are substituted with SEQ ID NO. 61).

9. The antibody of claim 1, wherein said antibody is selected from the group consisting of an antibody having a $V_L$ domain with one of the amino acid sequences shown in Table 10, (SEO ID NOs. 36 and 39–43) an antibody having a $V_H$ domain with one of the amino acid sequences shown in Table 12 (SEQ ID NOs. 44–59), an antibody having a $V_L$ CDR3 domain having one of the amino acid sequences shown in Tables 4 (SEQ ID NOs. 6–24) and 15 (SEQ ID NOs. 6, 7, 9, 12, 14, 15, 20–24, and 97–109), and an antibody having a $V_H$ CDR3 domain having one of the amino acid sequences shown in Table 14 (SEQ ID NOs. 61 and 68–95).

10. The antibody of claim 1, wherein said antibody expressed by any of the clones listed in Table 16.

11. The antibody of claim 1, wherein said antibody is a Fab.

12. The antibody of claim 1, wherein said antibody is a (Fab')$_2$.

13. The antibody of claim 1, wherein said antibody is an (SFv')$_2$.

14. The antibody of claim 13, wherein said (Sfv')$_2$ is a fusion protein of two sFv' fragments.

15. The antibody of claim 1, wherein said antibody is C6.5 ($V_H$ SEQ ID NO. 32 linked to $V_L$ SEO ID NO. 36) Fab.

16. The antibody of claim 1, wherein said antibody is C6.5 ($V_H$ SEQ ID NO. 32 linked to $V_L$ SEQ ID NO. 36) (Fab')$_2$.

17. The antibody of claim 1, wherein said antibody is C6.5 ($V_H$ SEO ID NO. 32 linked to VT SEO ID NO. 36) (SFv')$_2$.

18. The antibody of claim 1, wherein said antibody has a binding affinity ($K_d$) ranging from about $1.6 \times 10^{-8}$ M to $1.0 \times 10^{-11}$ M for a c-erbB-2 on an SK-BR-3 cell as determined using a Scatchard assay or for a purified c-erbB-2 as determined by surface plasmon resonance in a BIAcore.

19. The antibody of claim 1, wherein said $K_d$ for a purified c-erbB-2 is about $1.6 \times 10^{-8}$ M.

20. A polypeptide comprising one or more of the complementarity determining regions (CDRs) whose amino acid sequence contains a CDR sequence selected from the group consisting of the CDRs listed in Tables 4 (SEQ ID NOs. 6–24), 10 (SEQ ID NOs. 36 and 39–43), 12 (SEQ ID NOs. 44–59), 14 (SEQ ID NOs. 61 and 68–95), and 15 (SEQ ID NOs. 6, 7, 9, 12, 14, 15, 20–24, and 97–109).

21. An antibody selected from the group consisting of an antibody having a $V_L$ domain with one of the amino acid sequences shown in Table 10, (SEQ ID NOs. 36 and 39–43) an antibody having a $V_H$ domain with one of the amino acid sequences shown in Table 12 (SEQ ID NOs. 44–59), an antibody having a $V_L$ CDR3 domain having one of the amino acid sequences shown in Tables 4 (SEQ ID NOs. 6–24) and 15 (SEQ ID NOs. 6, 7, 9, 12, 14, 15, 20–24, and 97–109), and an antibody having a $V_H$ CDR3 domain having one of the amino acid sequences shown in Table 14 (SEQ ID NOs. 61 and 68–95).

22. The antibody of claim 21, wherein said antibody has a $V_L$ domain with one of the amino acid sequences shown in Table 10 (SEQ ID NOs. 36 and 39–43).

23. The antibody of claim 21, wherein said antibody has a $V_H$ domain with one of the amino acid sequences shown in Table 12. (SEQ ID NOs. 44–59).

24. The antibody of claim 21, wherein said antibody has a $V_L$ CDR3 domain having one of the amino acid sequences shown in Tables 4 (SEQ ID NOs. 6–24) and 15 (SEQ ID NOs. 6, 7, 9, 12, 14 15, 20–24, and 97–109).

25. The antibody of claim 21, wherein said antibody has a $V_H$ CDR3 domain having one of the amino acid sequences shown in Table 14 (SEQ ID NOs. 61 and 68–95).

26. The antibody of claim 21, wherein said antibody expressed by any of the clones listed in Table 16.

27. The antibody of claim 21, wherein said antibody is a Fab.

28. The antibody of claim 21, wherein said antibody is a (Fab')$_2$.

29. The antibody of claim 21, wherein said antibody is an (SFv')$_2$.

30. The antibody of claim 29, wherein said (Sfv')$_2$ is a fusion protein of two SFv' fragments.

31. The antibody of claim 21, wherein said antibody has a binding affinity ($K_d$) ranging from about $1.6 \times 10^{-8}$ M to $1.0 \times 10^{-11}$ M for a c-erbB-2 on an SK-BR-3 cell as determined using a Scatchard assay or for a purified c-erbB-2 as determined by surface plasmon resonance in a BIAcore.

32. The antibody of claim 31, wherein said $K_d$ is about $1.6 \times 10^{-8}$ M.

33. An isolated human antibody that specifically binds to c-erbB-2, said antibody being a C6 antibody, wherein said C6 antibody comprises a framework region of C6.5 ($V_H$ SEO ID NO. 32 linked to $V_L$ SEO ID NO.36).

34. The antibody of claim 33, wherein said antibody further comprises a C6.5 complementarity determining region (CDR) (amino acids 31–35, 50–66, or 99–118 of SEO ID NO. 32 or amino acids 23–35, 51–57, and 90–98 of SEQ ID NO. 36).

35. An isolated human antibody that specifically binds to c-erbB-2, said antibody being a C6 antibody, wherein said C6 antibody comprises a C6.5 complementarity determining region (amino acids 31–35, 50–66, or 99–118 of SEQ ID NO. 32 or amino acids 23–35, 51–57, and 90–98 of SEQ ID NO. 36).

36. An isolated human single chain antibody that has a binding affinity ($K_d$) of $1 \times 10^{-9}$ or greater for a c-erbB-2 on an SK-BR-3 cell as determined by a Scatchard assay or for a purified c-erbB-2 as determined by surface plasmon resonance in a BIAcore.

37. The antibody of claim 36, wherein said antibody specifically binds to c-erbB-2 with a binding affinity ($K_d$) of $1 \times 10^{-10}$ or better.

38. The antibody of claim 36, wherein said antibody has the variable heavy ($V_H$) chain of C6.5 (SEQ ID NO. 32).

39. The antibody of claim 36, wherein said antibody has the variable light ($V_L$) chain of C6.5 (SEO ID NO. 36).

40. The antibody of claim 36, wherein said antibody is selected from the group consisting of an antibody having a $V_L$ domain with one of the amino acid sequences shown in Table 10, (SEQ ID NOs. 36 and 39–43) an antibody having a $V_H$ domain with one of the amino acid sequences shown in Table 12 (SEO ID NOs. 44–59), an antibody having a $V_L$ CDR3 domain having one of the amino acid sequences shown in Tables 4 (SEQ ID NOs. 6–24) and 15 (SEQ ID NOs. 6, 7, 9, 12, 14, 15, 20–24, and 97–109), and an antibody having a $V_H$ CDR3 domain having one of the amino acid sequences shown in Table 14 (SEQ ID NOs. 61 and 68–95).

* * * * *

```
                            SEQUENCE LISTING (1) GENERAL INFORMATION:

(iii) NUMBER OF SEQUENCES: 141

(2) INFORMATION FOR SEQ ID NO:1:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Gly Gly Gly Gly Ser Gly Gly Gly Gly Ser Gly Gly Gly Gly Ser
   1               5                  10                  15

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Ser Ser Ser Ser Gly
```

5,977,322

81                                                                82

-continued

```
          1               5
```

(2) INFORMATION FOR SEQ ID NO:3:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

```
Ser Ser Ser Ser Gly Ser Ser Ser Ser Gly Ser Ser Ser Ser Gly
 1               5                  10                  15
```

(2) INFORMATION FOR SEQ ID NO:4:

(i) SEQUENCE CHARACTERISTICS:
        (A) LENGTH: 774 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..774
        (D) OTHER INFORMATION: /note= "sequence of C6 sFv
            antibody C6.5"

(xi) SEQUENCE DESCRIPTION: SEQ ID NO:4:

```
CAG GTG CAG CTG TTG CAG TCT GGG GCA GAG TTG AAA AAA CCC GGG GAG        48
Gln Val Gln Leu Leu Gln Ser Gly Ala Glu Leu Lys Lys Pro Gly Glu
 1               5                  10                  15

TCT CTG AAG ATC TCC TGT AAG GGT TCT GGA TAC AGC TTT ACC AGC TAC        96
Ser Leu Lys Ile Ser Cys Lys Gly Ser Gly Tyr Ser Phe Thr Ser Tyr
                20                  25                  30

TGG ATC GCC TGG GTG CGC CAG ATG CCC GGG AAA GGC CTG GAG TAC ATG       144
Trp Ile Ala Trp Val Arg Gln Met Pro Gly Lys Gly Leu Glu Tyr Met
            35                  40                  45

GGG CTC ATC TAT CCT GGT GAC TCT GAC ACC AAA TAC AGC CCG TCC TTC       192
Gly Leu Ile Tyr Pro Gly Asp Ser Asp Thr Lys Tyr Ser Pro Ser Phe
        50                  55                  60

CAA GGC CAG GTC ACC ATC TCA GTC GAC AAG TCC GTC AGC ACT GCC TAC       240
Gln Gly Gln Val Thr Ile Ser Val Asp Lys Ser Val Ser Thr Ala Tyr
 65                  70                  75                  80

TTG CAA TGG AGC AGT CTG AAG CCC TCG GAC AGC GCC GTG TAT TTT TGT       288
Leu Gln Trp Ser Ser Leu Lys Pro Ser Asp Ser Ala Val Tyr Phe Cys
                85                  90                  95

GCG AGA CAT GAC GTG GGA TAT TGC AGT AGT TCC AAC TGC GCA AAG TGG       336
Ala Arg His Asp Val Gly Tyr Cys Ser Ser Ser Asn Cys Ala Lys Trp
            100                 105                 110

CCT GAA TAC TTC CAG CAT TGG GGC CAG GGC ACC CTG GTC ACC GTC TCC       384
Pro Glu Tyr Phe Gln His Trp Gly Gln Gly Thr Leu Val Thr Val Ser
        115                 120                 125

TCA GGT GGA GGC GGT TCA GGC GGA GGT GGC TCT GGC GGT GGC GGA TCG       432
Ser Gly Gly Gly Gly Ser Gly Gly Gly Gly Ser Gly Gly Gly Gly Ser
    130                 135                 140

CAG TCT GTG TTG ACG CAG CCG CCC TCA GTG TCT GCG GCC CCA GGA CAG       480
Gln Ser Val Leu Thr Gln Pro Pro Ser Val Ser Ala Ala Pro Gly Gln
145                 150                 155                 160

AAG GTC ACC ATC TCC TGC TCT GGA AGC AGC TCC AAC ATT GGG AAT AAT       528
Lys Val Thr Ile Ser Cys Ser Gly Ser Ser Ser Asn Ile Gly Asn Asn
                165                 170                 175
```

-continued

```
TAT GTA TCC TGG TAC CAG CAG CTC CCA GGA ACA GCC CCC AAA CTC CTC     576
Tyr Val Ser Trp Tyr Gln Gln Leu Pro Gly Thr Ala Pro Lys Leu Leu
            180                 185                 190

ATC TAT GGT CAC ACC AAT CGG CCC GCA GGG GTC CCT GAC CGA TTC TCT     624
Ile Tyr Gly His Thr Asn Arg Pro Ala Gly Val Pro Asp Arg Phe Ser
        195                 200                 205

GGC TCC AAG TCT GGC ACC TCA GCC TCC CTG GCC ATC AGT GGG TTC CGG     672
Gly Ser Lys Ser Gly Thr Ser Ala Ser Leu Ala Ile Ser Gly Phe Arg
    210                 215                 220

TCC GAG GAT GAG GCT GAT TAT TAC TGT GCA GCA TGG GAT GAC AGC CTG     720
Ser Glu Asp Glu Ala Asp Tyr Tyr Cys Ala Ala Trp Asp Asp Ser Leu
225                 230                 235                 240

AGT GGT TGG GTG TTC GGC GGA GGG ACC AAG CTG ACC GTC CTA GGT GCG     768
Ser Gly Trp Val Phe Gly Gly Gly Thr Lys Leu Thr Val Leu Gly Ala
                245                 250                 255

GCC GCA                                                              774
Ala Ala
```

(2) INFORMATION FOR SEQ ID NO:5:

(i) SEQUENCE CHARACTERISTICS:
        (A) LENGTH: 258 amino acids
        (B) TYPE: amino acid
        (D) TOPOLOGY: linear (ii) MOLECULE TYPE: protein (xi) SEQUENCE DESCRIPTION: SEQ ID NO:5:

```
Gln Val Gln Leu Leu Gln Ser Gly Ala Glu Leu Lys Lys Pro Gly Glu
 1               5                  10                  15

Ser Leu Lys Ile Ser Cys Lys Gly Ser Gly Tyr Ser Phe Thr Ser Tyr
             20                  25                  30

Trp Ile Ala Trp Val Arg Gln Met Pro Gly Lys Gly Leu Glu Tyr Met
         35                  40                  45

Gly Leu Ile Tyr Pro Gly Asp Ser Asp Thr Lys Tyr Ser Pro Ser Phe
     50                  55                  60

Gln Gly Gln Val Thr Ile Ser Val Asp Lys Ser Val Ser Thr Ala Tyr
 65                  70                  75                  80

Leu Gln Trp Ser Ser Leu Lys Pro Ser Asp Ser Ala Val Tyr Phe Cys
                 85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gly Gly Gly Gly Ser Gly Gly Gly Gly Ser
    130                 135                 140

Gln Ser Val Leu Thr Gln Pro Pro Ser Val Ser Ala Ala Pro Gly Gln
145                 150                 155                 160

Lys Val Thr Ile Ser Cys Ser Gly Ser Ser Ser Asn Ile Gly Asn Asn
                165                 170                 175

Tyr Val Ser Trp Tyr Gln Gln Leu Pro Gly Thr Ala Pro Lys Leu Leu
            180                 185                 190

Ile Tyr Gly His Thr Asn Arg Pro Ala Gly Val Pro Asp Arg Phe Ser
        195                 200                 205

Gly Ser Lys Ser Gly Thr Ser Ala Ser Leu Ala Ile Ser Gly Phe Arg
    210                 215                 220

Ser Glu Asp Glu Ala Asp Tyr Tyr Cys Ala Ala Trp Asp Asp Ser Leu
225                 230                 235                 240
```

```
Ser Gly Trp Val Phe Gly Gly Gly Thr Lys Leu Thr Val Leu Gly Ala
            245                 250                 255

Ala Ala
```

(2) INFORMATION FOR SEQ ID NO:6:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Ala Ala Trp Asp Asp Ser Leu Ser Gly Trp Val
 1               5                   10
```

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

```
Ala Ala Trp Asp Tyr Ser Leu Ser Gly Trp Val
 1               5                   10
```

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

```
Ala Ala Trp Asp His Ser Leu Ser Gly Trp Val
 1               5                   10
```

(2) INFORMATION FOR SEQ ID NO:9:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

```
Ala Ser Trp Asp Tyr Ser Leu Ser Gly Trp Val
 1               5                   10
```

(2) INFORMATION FOR SEQ ID NO:10:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Ala Ala Trp Asp Tyr Ser Leu Trp Gly Trp Val
    1               5                  10

(2) INFORMATION FOR SEQ ID NO:11:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:11:

Ala Thr Trp Asp Tyr Ala Leu Ser Gly Trp Val
    1               5                  10

(2) INFORMATION FOR SEQ ID NO:12:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:12:

Ala Ala Trp Asp Tyr Ala Val Ser Gly Trp Val
    1               5                  10

(2) INFORMATION FOR SEQ ID NO:13:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:13:

Ala Ser Trp Glu Tyr Ser Leu Trp Gly Trp Val
    1               5                  10

(2) INFORMATION FOR SEQ ID NO:14:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:14:

Ala Ala Trp Asp Tyr Ser Arg Ser Gly Trp Val
    1               5                  10

(2) INFORMATION FOR SEQ ID NO:15:

(i) SEQUENCE CHARACTERISTICS:
          (A) LENGTH: 11 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:15:

Ala Ser Trp Asp Tyr Thr Leu Ser Gly Trp Val
1               5                   10

(2) INFORMATION FOR SEQ ID NO:16:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

Ala Ala Trp Glu Asp Pro Trp Tyr Gly Trp Val
1               5                   10

(2) INFORMATION FOR SEQ ID NO:17:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

Ala Ala Trp Asp Tyr Ala Leu Trp Gly Trp Val
1               5                   10

(2) INFORMATION FOR SEQ ID NO:18:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

Ala Ala Trp Asp Ala Thr Leu Trp Gly Trp Val
1               5                   10

(2) INFORMATION FOR SEQ ID NO:19:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

Ala Ala Trp Asp His Leu Arg Trp Gly Trp Val
1               5                   10

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

Ala Ser Trp Asp His Ser Leu Trp Gly Trp Val
    1               5                   10

(2) INFORMATION FOR SEQ ID NO:21:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

Ala Ser Trp Asp Arg Pro Leu Trp Gly Trp Val
    1               5                   10

(2) INFORMATION FOR SEQ ID NO:22:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

Ala Ala Trp Asp Gly Thr Leu Trp Gly Trp Val
    1               5                   10

(2) INFORMATION FOR SEQ ID NO:23:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:23:

Ala Ala Trp Asp Arg Pro Leu Trp Gly Trp Val
    1               5                   10

(2) INFORMATION FOR SEQ ID NO:24:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

Ala Ala Trp Asp Asp Pro Leu Trp Gly Trp Val
    1               5                   10

(2) INFORMATION FOR SEQ ID NO:25:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:25:

Gly Gly Gly Gly Ser
    1               5

(2) INFORMATION FOR SEQ ID NO:26:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

Arg Glu Asp Leu Lys
    1               5

(2) INFORMATION FOR SEQ ID NO:27:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

Arg Glu Asp Leu
    1

(2) INFORMATION FOR SEQ ID NO:28:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

Arg Asp Glu Leu
    1

(2) INFORMATION FOR SEQ ID NO:29:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

Lys Asp Glu Leu
    1

(2) INFORMATION FOR SEQ ID NO:30:

(i) SEQUENCE CHARACTERISTICS:
        (A) LENGTH: 123 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Gly Tyr Ser Tyr Gly Tyr Val Gly Leu Asp Tyr
            100                 105                 110

Trp Gly Gln Gly Thr Leu Val Thr Val Ser Ser
            115                 120

(2) INFORMATION FOR SEQ ID NO:31:

(i) SEQUENCE CHARACTERISTICS:
        (A) LENGTH: 98 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg (2) INFORMATION FOR SEQ ID NO:32:

(i) SEQUENCE CHARACTERISTICS:
        (A) LENGTH: 129 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

Gln Val Gln Leu Leu Gln Ser Gly Ala Glu Leu Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met 35                  40                  45
    Gly Leu Ile Tyr Pro Gly Asp Ser Asp Thr Lys Tyr Ser Pro Ser Phe
             50                  55                  60

Gln Gly Gln Val Thr Ile Ser Val Asp Lys Ser Val Ser Thr Ala Tyr
    65                  70                  75                  80

Leu Gln Trp Ser Ser Leu Lys Pro Ser Asp Ser Ala Val Tyr Phe Cys
                     85                  90                  95

Ala Arg His Asp Val Gly Tyr Cys Ser Ser Asn Cys Ala Lys Trp
                100                 105                 110

Pro Glu Tyr Phe Gln His Trp Gly Gln Gly Thr Leu Val Thr Val Ser
                115                 120                 125

Ser (2) INFORMATION FOR SEQ ID NO:33:

(i) SEQUENCE CHARACTERISTICS:
        (A) LENGTH: 98 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

Glu Val Gln Leu Val Gln Ser Gly Ala Glu Val Lys Lys Pro Gly Glu
    1               5                   10                  15

Ser Leu Lys Ile Ser Cys Lys Gly Ser Gly Tyr Ser Phe Thr Ser Tyr
                    20                  25                  30

Trp Ile Gly Trp Val Arg Gln Met Pro Gly Lys Gly Leu Glu Trp Met
                35                  40                  45

Gly Ile Ile Tyr Pro Gly Asp Ser Asp Thr Arg Tyr Ser Pro Ser Phe
             50                  55                  60

Gln Gly Gln Val Thr Ile Ser Ala Asp Lys Ser Ile Ser Thr Ala Tyr
    65                  70                  75                  80

Leu Gln Trp Ser Ser Leu Lys Ala Ser Asp Thr Ala Met Tyr Tyr Cys
                     85                  90                  95

Ala Arg (2) INFORMATION FOR SEQ ID NO:34:

(i) SEQUENCE CHARACTERISTICS:
        (A) LENGTH: 109 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

Ser Glu Leu Thr Gln Asp Pro Ala Val Ser Val Ala Leu Gly Gln Thr
    1               5                   10                  15

Val Arg Ile Thr Cys Gln Gly Asp Ser Leu Arg Ser Tyr Tyr Ala Ser
                    20                  25                  30

Trp Tyr Gln Gln Lys Pro Gly Gln Ala Pro Val Leu Val Ile Tyr Gly
                35                  40                  45

Lys Asn Asn Arg Pro Ser Gly Ile Pro Asp Arg Phe Ser Gly Ser Ser
             50                  55                  60

Ser Gly Asn Ile Ala Ser Leu Thr Ile Thr Gly Ala Gln Ala Glu Asp
    65                  70                  75                  80

```
           Glu Ala Asp Tyr Tyr Cys Asn Ser Arg Asp Ser Ser Gly Asn Pro Tyr
                           85                  90                  95

Trp Val Phe Gly Gly Gly Thr Lys Val Thr Val Leu Gly
                          100                 105
```

(2) INFORMATION FOR SEQ ID NO:35:

(i) SEQUENCE CHARACTERISTICS:
        (A) LENGTH: 97 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

```
           Ser Ser Leu Thr Gln Asp Pro Ala Val Ser Val Ala Leu Gly Gln Thr
           1               5                  10                  15

Val Arg Ile Thr Cys Gln Gly Asp Ser Leu Arg Ser Tyr Tyr Ala Ser
                          20                  25                  30

Trp Tyr Gln Gln Lys Pro Gly Gln Ala Pro Val Leu Val Ile Tyr Gly
                          35                  40                  45

Lys Asn Asn Arg Pro Ser Gly Ile Pro Asp Arg Phe Ser Gly Ser Ser
                 50                  55                  60

Ser Gly Asn Thr Ala Ser Leu Thr Ile Thr Gly Ala Gln Ala Glu Asp
           65                  70                  75                  80

Glu Ala Asp Tyr Tyr Cys Asn Ser Arg Asp Ser Ser Gly Asn His Val
                           85                  90                  95

Val
```

(2) INFORMATION FOR SEQ ID NO:36:

(i) SEQUENCE CHARACTERISTICS:
        (A) LENGTH: 111 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

```
           Gln Ser Val Leu Thr Gln Pro Pro Ser Val Ser Ala Ala Pro Gly Gln
           1               5                  10                  15

Lys Val Thr Ile Ser Cys Ser Gly Ser Ser Ser Asn Ile Gly Asn Asn
                          20                  25                  30

Tyr Val Ser Trp Tyr Gln Gln Leu Pro Gly Thr Ala Pro Lys Leu Leu
                          35                  40                  45

Ile Tyr Gly His Thr Asn Arg Pro Ala Gly Val Pro Asp Arg Phe Ser
                 50                  55                  60

Gly Ser Lys Ser Gly Thr Ser Ala Ser Leu Ala Ile Ser Gly Phe Arg
           65                  70                  75                  80

Ser Glu Asp Glu Ala Asp Tyr Tyr Cys Ala Ala Trp Asp Asp Ser Leu
                           85                  90                  95

Ser Gly Trp Val Phe Gly Gly Gly Thr Lys Leu Thr Val Leu Gly
                          100                 105                 110
```

(2) INFORMATION FOR SEQ ID NO:37:

(i) SEQUENCE CHARACTERISTICS:
        (A) LENGTH: 98 amino acids
        (B) TYPE: amino acid
        (C) STRANDEDNESS:

(D) TOPOLOGY: linear (ii) MOLECULE TYPE: peptide (xi) SEQUENCE DESCRIPTION: SEQ ID NO:37:

Gln Ser Val Leu Thr Gln Pro Pro Ser Val Ser Ala Ala Pro Gly Gln
    1               5                   10                  15

Lys Val Thr Ile Ser Cys Ser Gly Ser Ser Ser Asn Ile Gly Asn Asn
                    20                  25                  30

Tyr Val Ser Trp Tyr Gln Gln Leu Pro Gly Thr Ala Pro Lys Leu Leu
                35                  40                  45

Ile Tyr Asp Asn Lys Lys Arg Pro Ser Gly Ile Pro Asp Arg Phe Ser
            50                  55                  60

Gly Ser Lys Ser Gly Thr Ser Ala Thr Leu Gly Ile Thr Gly Leu Gln
    65                  70                  75                  80

Thr Gly Asp Glu Ala Asp Tyr Tyr Cys Gly Thr Trp Asp Ser Ser Leu
                    85                  90                  95

Ser Ala (2) INFORMATION FOR SEQ ID NO:38:

(i) SEQUENCE CHARACTERISTICS:
        (A) LENGTH: 98 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

Gln Ser Val Leu Thr Gln Pro Pro Ser Ala Ser Gly Thr Pro Gly Gln
    1               5                   10                  15

Arg Val Thr Ile Ser Cys Ser Gly Ser Ser Ser Asn Ile Gly Ser Asn
                    20                  25                  30

Tyr Val Tyr Trp Tyr Gln Gln Leu Pro Gly Thr Ala Pro Lys Leu Leu
                35                  40                  45

Ile Tyr Arg Asn Asn Gln Arg Pro Ser Gly Val Pro Asp Arg Phe Ser
            50                  55                  60

Gly Ser Lys Ser Gly Thr Ser Ala Ser Leu Ala Ile Ser Gly Leu Arg
    65                  70                  75                  80

Ser Glu Asp Glu Ala Asp Tyr Tyr Cys Ala Ala Trp Asp Asp Ser Leu
                    85                  90                  95

Ser Gly (2) INFORMATION FOR SEQ ID NO:39:

(i) SEQUENCE CHARACTERISTICS:
        (A) LENGTH: 112 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

Gln Ser Val Leu Thr Gln Pro Pro Ser Val Ser Ala Ala Pro Gly Gln
    1               5                   10                  15

Lys Val Thr Ile Ser Cys Ser Gly Ser Ser Ser Asn Ile Gly Asn Asn
                    20                  25                  30

Tyr Val Ser Trp Tyr Gln Gln Leu Pro Gly Thr Ala Pro Lys Leu Leu
                35                  40                  45

```
    Ile Tyr Ser Asp Asn Gln Arg Pro Ser Gly Val Pro Asp Arg Phe Ser
         50                  55                  60

Gly Ser Lys Ser Gly Thr Ser Ala Ser Leu Ala Ile Ser Gly Leu Arg
     65                  70                  75                  80

Ser Glu Asp Glu Ala Asp Tyr Tyr Cys Ala Ala Trp Asp Asp Ser Leu
                     85                  90                  95

Ser Gly His Trp Val Phe Gly Gly Thr Lys Leu Thr Val Leu Gly
                    100                 105                 110
```

(2) INFORMATION FOR SEQ ID NO:40:

(i) SEQUENCE CHARACTERISTICS:
        (A) LENGTH: 111 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

```
    Gln Ser Val Leu Thr Gln Pro Pro Ser Val Ser Ala Ala Pro Gly Gln
     1               5                  10                  15

Lys Val Thr Ile Ser Cys Ser Gly Thr Asn Ser Asn Ile Gly Asn Asn
                     20                  25                  30

Tyr Val Ser Trp Tyr Gln Gln Leu Pro Gly Thr Ala Pro Lys Leu Leu
                     35                  40                  45

Ile Tyr Thr Asn Asp Gln Arg Pro Ser Gly Val Pro Asp Arg Phe Ser
         50                  55                  60

Gly Ser Lys Ser Gly Thr Ser Ala Ser Leu Ala Ile Ser Gly Leu Gln
     65                  70                  75                  80

Ser Glu Asp Glu Ala Asp Tyr Tyr Cys Ala Ala Trp Asp Asp Ser Leu
                     85                  90                  95

Asn Gly Trp Met Phe Gly Gly Gly Thr Lys Leu Thr Val Leu Gly
                    100                 105                 110
```

(2) INFORMATION FOR SEQ ID NO:41:

(i) SEQUENCE CHARACTERISTICS:
        (A) LENGTH: 111 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

```
    Gln Ser Val Leu Thr Gln Pro Pro Ser Val Ser Ala Ala Ala Gly Gln
     1               5                  10                  15

Lys Val Thr Ile Ser Cys Ser Gly Ser Ser Ser Ser Ile Gly Arg Asn
                     20                  25                  30

Tyr Val Ser Trp Asn Gln Gln Leu Pro Gly Thr Ala Pro Lys Leu Leu
                     35                  40                  45

Ile Trp Arg Asn Asn Gln Arg Pro Ser Gly Val Pro Asp Arg Phe Ser
         50                  55                  60

Gly Ser Lys Ser Gly Thr Ser Ala Ser Leu Ala Ile Ser Gly Val Arg
     65                  70                  75                  80

Ser Glu Asp Glu Ala Asp Tyr Tyr Cys Ala Ser Trp Asp Asn Ser Leu
                     85                  90                  95

Ser Gly Trp Val Phe Gly Gly Gly Thr Lys Leu Thr Val Leu Gly
                    100                 105                 110
```

(2) INFORMATION FOR SEQ ID NO:42:

(i) SEQUENCE CHARACTERISTICS:
        (A) LENGTH: 111 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

```
Gln Ser Val Leu Thr Gln Pro Pro Ser Met Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Phe Pro Gly Thr Ala Pro Lys Leu Leu
            35                  40                  45

Ile His Asp Asn Asn Lys Arg Pro Ser Gly Ile Pro Asp Arg Ile Ser
        50                  55                  60

Gly Ser Lys Ser Gly Thr Ser Ala Ser Leu Ala Ile Ser Gly Leu Gln
65                  70                  75                  80

Ser Asp Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly
                100                 105                 110
```

(2) INFORMATION FOR SEQ ID NO:43:

(i) SEQUENCE CHARACTERISTICS:
        (A) LENGTH: 111 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

```
Gln Ser Val Leu Thr Gln Pro Pro Ser Val Ser Gly Ala Pro Gly Gln
1               5                   10                  15

Trp Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Val Pro Asp Arg Phe Ser
        50                  55                  60

Gly Ser Gln Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly
                100                 105                 110
```

(2) INFORMATION FOR SEQ ID NO:44:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

Gln Val Gln Leu Leu Gln Ser Gly Ala Glu Leu Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val
        115                 120                 125

(2) INFORMATION FOR SEQ ID NO:45:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:45:

Gln Val Gln Leu Val Gln Ser Gly Gly Glu Met Lys Lys Pro Gly Glu
1               5                   10                  15

Ser Leu Lys Ile Ser Cys Lys Gly Leu Gly Tyr Asp Phe Thr Thr Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Arg Pro Ser Asp Thr Ala Met Tyr Tyr Cys
                85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val
        115                 120                 125

(2) INFORMATION FOR SEQ ID NO:46:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:46:

Gln Val Gln Leu Gln Gln Ser Gly Gly Glu Met Lys Lys Pro Gly Glu
1               5                   10                  15

Ser Leu Lys Ile Ser Cys Lys Gly Leu Gly Tyr Asp Phe Thr Thr Tyr

```
                    20                  25                  30
    Trp  Ile  Ala  Trp  Val  Arg  Gln  Met  Pro  Gly  Lys  Gly  Leu  Glu  Tyr  Met
                        35                  40                  45

Gly  Leu  Ile  Tyr  Pro  Gly  Asp  Ser  Asp  Thr  Lys  Tyr  Ser  Pro  Ser  Phe
     50                      55                  60

Gln  Gly  Gln  Val  Thr  Ile  Ser  Ala  Asp  Glu  Ser  Ile  Ser  Thr  Ala  Tyr
     65                      70                  75                       80

Leu  Glu  Trp  Ser  Ser  Leu  Lys  Ala  Ser  Asp  Thr  Ala  Met  Tyr  Tyr  Cys
                        85                  90                       95

Ala  Arg  His  Asp  Val  Gly  Tyr  Cys  Ser  Ser  Ser  Asn  Cys  Ala  Lys  Trp
                        100                 105                      110

Pro  Glu  Tyr  Phe  Gln  His  Trp  Gly  Gln  Gly  Thr  Leu  Val
                        115                 120                 125
```

(2) INFORMATION FOR SEQ ID NO:47:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:47:

```
    Gln  Val  Gln  Leu  Gln  Gln  Ser  Gly  Gly  Glu  Met  Lys  Lys  Pro  Gly  Glu
     1                       5                  10                       15

Ser  Leu  Lys  Ile  Ser  Cys  Lys  Gly  Ser  Glu  Tyr  Ser  Phe  Ser  Thr  Tyr
                        20                  25                  30

Trp  Ile  Ala  Trp  Val  Arg  Gln  Met  Pro  Gly  Lys  Gly  Leu  Glu  Tyr  Met
                        35                  40                  45

Gly  Leu  Ile  Tyr  Pro  Gly  Asp  Ser  Asp  Thr  Lys  Tyr  Ser  Pro  Ser  Phe
     50                      55                  60

Gln  Gly  Gln  Val  Thr  Ile  Ser  Val  Asp  Lys  Ser  Val  Ser  Thr  Thr  Tyr
     65                      70                  75                       80

Leu  Gln  Trp  Ser  Ser  Leu  Arg  Pro  Ser  Asp  Thr  Ala  Val  Tyr  Tyr  Cys
                        85                  90                       95

Ala  Arg  His  Asp  Val  Gly  Tyr  Cys  Ser  Ser  Ser  Asn  Cys  Ala  Lys  Trp
                        100                 105                      110

Pro  Glu  Tyr  Phe  Gln  His  Trp  Gly  Gln  Gly  Thr  Leu  Val
                        115                 120                 125
```

(2) INFORMATION FOR SEQ ID NO:48:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:48:

```
    Gln  Val  Gln  Leu  Val  Glu  Ser  Gly  Ala  Glu  Met  Lys  Lys  Pro  Gly  Glu
     1                       5                  10                       15

Ser  Leu  Lys  Ile  Ser  Cys  Lys  Gly  Phe  Gly  Tyr  Asp  Phe  Ser  Thr  Tyr
                        20                  25                  30

Trp  Ile  Ala  Trp  Val  Arg  Gln  Met  Pro  Gly  Lys  Gly  Leu  Glu  Tyr  Met
                        35                  40                  45

Gly  Leu  Ile  Tyr  Pro  Gly  Asp  Ser  Asp  Thr  Lys  Tyr  Ser  Pro  Ser  Phe
```

```
                    50                  55                  60
Gln Gly Gln Val Thr Ile Ser Val Asp Lys Ser Val Ser Thr Ala Tyr
 65                  70                  75                  80

Leu Gln Trp Ser Ser Leu Lys Pro Ser Asp Thr Ala Met Tyr Tyr Cys
                     85                  90                  95

Ala Arg His Asp Val Gly Tyr Cys Ser Ser Ser Asn Cys Ala Lys Trp
                    100                 105                 110

Pro Glu Tyr Phe Gln His Trp Gly Gln Gly Thr Leu Val
                    115                 120                 125
```

(2) INFORMATION FOR SEQ ID NO:49:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:49:

```
Gln Val Gln Leu Val Glu Ser Gly Gly Glu Met Lys Lys Pro Arg Glu
  1               5                  10                  15

Ser Leu Lys Ile Ser Cys Lys Gly Leu Gly Tyr Asp Phe Thr Thr Tyr
                 20                  25                  30

Trp Ile Ala Trp Val Arg Gln Met Pro Gly Lys Gly Leu Glu Tyr Met
                 35                  40                  45

Gly Leu Ile Tyr Pro Gly Asp Ser Asp Thr Lys Tyr Ser Pro Ser Phe
             50                  55                  60

Gln Gly Gln Val Thr Ile Ser Val Asp Lys Ser Val Ser Thr Ala Tyr
 65                  70                  75                  80

Leu Gln Trp Ser Ser Leu Arg Pro Ser Asp Thr Ala Met Tyr Tyr Cys
                     85                  90                  95

Ala Arg His Asp Val Gly Tyr Cys Ser Ser Ser Asn Cys Ala Lys Trp
                    100                 105                 110

Pro Glu Tyr Phe Gln His Trp Gly Gln Gly Thr Leu Val
                    115                 120                 125
```

(2) INFORMATION FOR SEQ ID NO:50:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:50:

```
Gln Val Gln Leu Val Glu Ser Gly Gly Glu Met Lys Lys Pro Gly Glu
  1               5                  10                  15

Ser Leu Lys Ile Ser Cys Lys Gly Leu Gly Tyr Asp Phe Ser Thr Tyr
                 20                  25                  30

Trp Ile Ala Trp Val Arg Gln Met Pro Gly Lys Gly Leu Glu Tyr Met
                 35                  40                  45

Gly Leu Ile Tyr Pro Gly Asp Ser Asp Thr Lys Tyr Ser Pro Ser Phe
             50                  55                  60

Gln Gly Gln Val Thr Ile Ser Val Asp Lys Ser Val Ser Thr Ala Tyr
 65                  70                  75                  80

Leu Gln Trp Ser Ser Leu Arg Pro Ser Asp Thr Ala Met Tyr Tyr Cys
```

```
                        85                  90                  95
    Ala Arg His Asp Val Gly Tyr Cys Ser Ser Asn Cys Ala Lys Trp
                    100                 105                 110

Pro Glu Tyr Phe Gln His Trp Gly Gln Gly Thr Leu Val
                115                 120                 125
```

(2) INFORMATION FOR SEQ ID NO:51:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:51:

```
    Gln Val Gln Leu Val Glu Ser Gly Gly Glu Met Lys Lys Pro Gly Glu
    1               5                   10                  15

Ser Leu Lys Ile Ser Cys Lys Gly Leu Gly Tyr Asp Phe Thr Thr Tyr
                    20                  25                  30

Trp Ile Ala Trp Val Arg Gln Met Pro Gly Lys Gly Leu Glu Tyr Met
                35                  40                  45

Gly Leu Ile Tyr Pro Gly Asp Ser Asp Thr Lys Tyr Ser Pro Ser Phe
            50                  55                  60

Gln Gly Gln Val Thr Ile Ser Val Asp Lys Ser Val Ser Thr Ala Tyr
    65                  70                  75                  80

Leu Gln Trp Ser Ser Leu Arg Pro Ser Asp Thr Ala Met Tyr Tyr Cys
                        85                  90                  95

Ala Arg His Asp Val Gly Tyr Cys Ser Ser Ser Asn Cys Ala Lys Trp
                    100                 105                 110

Pro Glu Tyr Phe Gln His Trp Gly Gln Gly Thr Leu Val
                115                 120                 125
```

(2) INFORMATION FOR SEQ ID NO:52:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:52:

```
    Gln Val Gln Leu Val Glu Ser Gly Ala Glu Met Lys Lys Pro Gly Glu
    1               5                   10                  15

Ser Leu Lys Ile Ser Cys Lys Gly Phe Gly Tyr Asp Phe Ser Thr Tyr
                    20                  25                  30

Trp Ile Ala Trp Val Arg Gln Met Pro Gly Lys Gly Leu Glu Tyr Met
                35                  40                  45

Gly Leu Ile Tyr Pro Gly Asp Ser Asp Thr Lys Tyr Ser Pro Ser Phe
            50                  55                  60

Gln Gly Gln Val Thr Ile Ser Val Asp Lys Ser Val Ser Thr Ala Tyr
    65                  70                  75                  80

Leu Gln Trp Ser Ser Leu Arg Pro Ser Asp Thr Ala Met Tyr Tyr Cys
                        85                  90                  95

Ala Arg His Asp Val Gly Tyr Cys Ser Ser Ser Asn Cys Ala Lys Trp
                    100                 105                 110

Pro Glu Tyr Phe Gln His Trp Gly Gln Gly Thr Leu Val
```

(2) INFORMATION FOR SEQ ID NO:53:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:53:

```
Gln Val Gln Leu Val Gln Ser Gly Gly Glu Met Lys Lys Pro Gly Glu
  1               5                  10                  15
Ser Leu Lys Ile Ser Cys Lys Gly Leu Gly Tyr Asp Phe Ser Thr Tyr
             20                  25                  30
Trp Ile Ala Trp Val Arg Gln Met Pro Gly Lys Gly Leu Glu Tyr Met
         35                  40                  45
Gly Leu Ile Tyr Pro Gly Asp Ser Asp Thr Lys Tyr Ser Pro Ser Phe
     50                  55                  60
Gln Gly Gln Val Thr Ile Ser Ala Asp Glu Ser Ile Ser Thr Ala Tyr
 65                  70                  75                  80
Leu Glu Trp Ser Ser Leu Lys Ala Ser Asp Thr Ala Met Tyr Tyr Cys
                 85                  90                  95
Ala Arg His Asp Val Gly Tyr Cys Ser Ser Ser Asn Cys Ala Lys Trp
                100                 105                 110
Pro Glu Tyr Phe Gln His Trp Gly Gln Gly Thr Leu Val
                115                 120                 125
```

(2) INFORMATION FOR SEQ ID NO:54:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:54:

```
Gln Val Gln Leu Val Gln Ser Gly Gly Glu Met Lys Lys Pro Gly Glu
  1               5                  10                  15
Ser Leu Lys Ile Ser Cys Lys Gly Leu Gly Tyr Asp Phe Ser Thr Tyr
             20                  25                  30
Trp Ile Ala Trp Val Arg Gln Met Pro Gly Lys Gly Leu Glu Tyr Met
         35                  40                  45
Gly Leu Ile Tyr Pro Gly Asp Ser Asp Thr Lys Tyr Ser Pro Ser Phe
     50                  55                  60
Gln Gly Gln Val Thr Ile Ser Ala Asp Glu Ser Ile Ser Thr Ala Tyr
 65                  70                  75                  80
Leu Glu Trp Ser Ser Leu Lys Ala Ser Asp Thr Ala Met Tyr Tyr Cys
                 85                  90                  95
Ala Arg His Asp Val Gly Tyr Cys Ser Ser Ser Asn Cys Ala Lys Trp
                100                 105                 110
Pro Glu Tyr Phe Gln His Trp Gly Gln Gly Thr Leu Val
                115                 120                 125
```

(2) INFORMATION FOR SEQ ID NO:55:

(i) SEQUENCE CHARACTERISTICS:

(A) LENGTH: 125 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:55:

Gln Val Gln Leu Leu Gln Ser Gly Ala Glu Met Lys Lys Pro Gly Glu
1               5                   10                  15

Ser Leu Lys Ile Ser Cys Lys Gly Phe Gly Tyr Asp Phe Ser Thr Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Thr Ala Met Tyr Tyr Cys
                85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val
        115                 120                 125

(2) INFORMATION FOR SEQ ID NO:56:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:56:

Gln Val Gln Leu Leu Gln Ser Gly Ala Glu Val Lys Lys Pro Gly Glu
1               5                   10                  15

Ser Leu Gln Ile Ser Cys Lys Gly Ser Gly Tyr Asp Phe Thr Thr Tyr
            20                  25                  30

Tyr Ile Ala Trp Val Arg Gln Met Pro Gly Lys Gly Leu Glu Tyr Met
        35                  40                  45

Gly Ile Ile Tyr Pro Gly Asp Ser Arg Thr Ile Tyr Ser Pro Ser Phe
    50                  55                  60

Gln Gly Gln Val Arg Ile Ser Ala Asp Lys Ser Val Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val
        115                 120                 125

(2) INFORMATION FOR SEQ ID NO:57:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:57:

Gln Val Gln Leu Leu Glu Ser Gly Ala Glu Val Lys Glu Pro Gly Gln
1               5                   10                  15

Ser Leu Lys Ile Ser Cys Lys Gly Phe Gly Tyr Asp Phe Ser Thr Tyr
                20                  25                  30

Trp Ile Ala Trp Val Arg Gln Met Pro Gly Lys Gly Leu Glu Tyr Met
            35                  40                  45

Gly Leu Ile Tyr Pro Gly Asp Ser Asp Thr Lys Tyr Ser Pro Ser Phe
        50                  55                  60

Gln Gly Gln Val Thr Ile Ser Val Asp Lys Ser Val Ser Thr Ala Tyr
65                      70                  75                  80

Leu Gln Trp Ser Ser Leu Lys Pro Ser Asp Thr Ala Met Tyr Tyr Cys
                85                  90                  95

Ala Arg His Asp Val Gly Tyr Cys Ser Ser Ser Asn Cys Ala Lys Trp
                100                 105                 110

Pro Glu Tyr Phe Gln His Trp Gly Gln Gly Thr Leu Val
            115                 120                 125

(2) INFORMATION FOR SEQ ID NO:58:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 33
        (D) OTHER INFORMATION: /product= "OTHER"
            /note= "Xaa = unknown (possibly Glu)"

(xi) SEQUENCE DESCRIPTION: SEQ ID NO:58:

Gln Val Gln Leu Val Glu Ser Gly Ala Glu Val Lys Lys Pro Arg Glu
1               5                   10                  15

Ser Leu Lys Ile Ser Cys Lys Gly Ser Gly Tyr Ser Phe Thr Ser Tyr
                20                  25                  30

Xaa Ile Ala Trp Val Arg Gln Met Pro Gly Lys Gly Leu Glu Tyr Met
            35                  40                  45

Gly Leu Ile Tyr Pro Gly Asp Ser Asp Thr Lys Tyr Ser Pro Ser Phe
        50                  55                  60

Gln Gly Gln Val Thr Ile Ser Val Asp Lys Ser Val Ser Thr Ala Tyr
65                      70                  75                  80

Leu Gln Trp Ser Ser Leu Lys Pro Ser Asp Thr Ala Met Tyr Tyr Cys
                85                  90                  95

Ala Arg His Asp Val Gly Tyr Cys Ser Ser Ser Asn Cys Ala Lys Trp
                100                 105                 110

Pro Glu Tyr Phe Gln His Trp Gly Gln Gly Thr Leu Val
            115                 120                 125

(2) INFORMATION FOR SEQ ID NO:59:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:59:

Gln Val Gln Leu Val Gln Ser Gly Ala Glu Val Lys Lys Pro Arg Glu
1               5                  10                 15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Ala Asp Ser Lys Thr Ile Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Thr Ser Asp Thr Ala Met Tyr Tyr Cys
                85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val
        115                 120                 125

(2) INFORMATION FOR SEQ ID NO:60:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:60:

Ala Ala Trp Asp Asp Ser Leu Ser Gly
    1               5

(2) INFORMATION FOR SEQ ID NO:61:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:61:

His Asp Val Gly Tyr Cys Ser Ser Ser Asn Cys Ala Lys Trp Pro Glu
    1               5                   10                  15

Tyr Phe Gln His
                20

(2) INFORMATION FOR SEQ ID NO:62:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:62:

Ser Ser Ser Asn
    1

(2) INFORMATION FOR SEQ ID NO:63:

```
    (i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:63:

Asp Val Gly Tyr
   1

(2) INFORMATION FOR SEQ ID NO:64:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:64:

Ala Lys Pro Glu
   1

(2) INFORMATION FOR SEQ ID NO:65:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:65:

Tyr Phe Gln His
   1

(2) INFORMATION FOR SEQ ID NO:66:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:66:

His Asp Val Gly Phe Cys Ser Ser Ser Asn Cys Ala Lys Trp Pro Glu
   1               5                  10                  15

Tyr Phe Gln His
              20

(2) INFORMATION FOR SEQ ID NO:67:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:67:

His Asp Val Gly Tyr Cys Ser Ser Ser Asp Cys Ala Lys Trp Pro Glu
   1               5                  10                  15
```

Tyr Phe Gln His
                 20

(2) INFORMATION FOR SEQ ID NO:68:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:68:

His Asp Val Gly Tyr Cys Thr Asp Arg Thr Cys Ala Lys Trp Pro Glu
    1               5                  10                  15

Tyr Phe Gln His
                 20

(2) INFORMATION FOR SEQ ID NO:69:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:69:

His Asp Val Gly Tyr Cys Glu Ser Arg Cys Ala Lys Trp Pro Glu
    1               5                  10                  15

Tyr Phe Gln His
                 20

(2) INFORMATION FOR SEQ ID NO:70:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:70:

His Asp Val Gly Tyr Cys Ser Asp Arg Ser Cys Ala Lys Trp Pro Glu
    1               5                  10                  15

Tyr Phe Gln His
                 20

(2) INFORMATION FOR SEQ ID NO:71:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:71:

His Asp Val Gly Tyr Cys Lys Thr Ala Ala Cys Ala Lys Trp Pro Glu
    1               5                  10                  15

Tyr Phe Gln His
                 20

(2) INFORMATION FOR SEQ ID NO:72:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "OTHER"
            /note= "Xaa = unknown"

(xi) SEQUENCE DESCRIPTION: SEQ ID NO:72:

His Asp Val Gly Tyr Cys Xaa Thr Glu Arg Cys Ala Lys Trp Pro Glu
1            5               10             15

Tyr Phe Gln His
        20

(2) INFORMATION FOR SEQ ID NO:73:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:73:

His Asp Val Gly Tyr Cys Thr Asp Pro Arg Cys Ala Lys Trp Pro Glu
1            5               10             15

Tyr Phe Gln His
        20

(2) INFORMATION FOR SEQ ID NO:74:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:74:

His Asp Val Gly Tyr Cys Thr Asp Pro Thr Cys Ala Lys Trp Pro Glu
1            5               10             15

Tyr Phe Gln His
        20

(2) INFORMATION FOR SEQ ID NO:75:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:75:

His Asp Val Gly Tyr Cys Leu Thr Thr Arg Cys Ala Lys Trp Pro Glu
1            5               10             15

Tyr Phe Gln His (2) INFORMATION FOR SEQ ID NO:76:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:76:

```
His Asp Val Gly Tyr Cys Thr Thr Pro Leu Cys Ala Lys Trp Pro Glu
1               5                  10                  15

Tyr Phe Gln His
            20
```

(2) INFORMATION FOR SEQ ID NO:77:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:77:

```
His Asp Val Gly Tyr Cys Ser Pro Ala Arg Cys Ala Lys Trp Pro Glu
1               5                  10                  15

Tyr Phe Gln His
            20
```

(2) INFORMATION FOR SEQ ID NO:78:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:78:

```
His Asp Val Gly Tyr Cys Ala Asp Val Arg Cys Ala Lys Trp Pro Glu
1               5                  10                  15

Tyr Phe Gln His
            20
```

(2) INFORMATION FOR SEQ ID NO:79:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:79:

```
His Asp Val Gly Tyr Cys Thr Asp Arg Ser Cys Ala Lys Trp Pro Glu
1               5                  10                  15

Tyr Phe Gln His
            20
```

(2) INFORMATION FOR SEQ ID NO:80:

(i) SEQUENCE CHARACTERISTICS:
           (A) LENGTH: 20 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:80:

His Asp Val Gly Tyr Cys Thr Asp Pro Ser Cys Ala Lys Trp Pro Glu
    1               5                   10                  15

Tyr Phe Gln His
                20

(2) INFORMATION FOR SEQ ID NO:81:

(i) SEQUENCE CHARACTERISTICS:
           (A) LENGTH: 20 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:81:

His Asp Val Gly Tyr Cys Thr Asp Ala Thr Cys Ala Lys Trp Pro Glu
    1               5                   10                  15

Tyr Phe Gln His
                20

(2) INFORMATION FOR SEQ ID NO:82:

(i) SEQUENCE CHARACTERISTICS:
           (A) LENGTH: 20 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:82:

His Asp Val Gly Tyr Cys Thr Asp Arg Pro Cys Ala Lys Trp Pro Glu
    1               5                   10                  15

Tyr Phe Gln His
                20

(2) INFORMATION FOR SEQ ID NO:83:

(i) SEQUENCE CHARACTERISTICS:
           (A) LENGTH: 20 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:83:

His Asp Val Gly Tyr Cys Lys Asn Ser Arg Cys Ala Lys Trp Pro Glu
    1               5                   10                  15

Tyr Phe Gln His
                20

(2) INFORMATION FOR SEQ ID NO:84:

(i) SEQUENCE CHARACTERISTICS:
           (A) LENGTH: 20 amino acids
           (B) TYPE: amino acid (C) STRANDEDNESS:
            (D) TOPOLOGY: linear (ii) MOLECULE TYPE: peptide (xi) SEQUENCE DESCRIPTION: SEQ ID NO:84:

His Asp Val Gly Tyr Cys Gln Asp Thr Arg Cys Ala Lys Trp Pro Glu
    1               5                   10                  15

Tyr Phe Gln His
                20

(2) INFORMATION FOR SEQ ID NO:85:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:85:

His Asp Val Gly Tyr Cys Glu Asp Tyr Thr Cys Ala Lys Trp Pro Glu
    1               5                   10                  15

Tyr Phe Gln His
                20

(2) INFORMATION FOR SEQ ID NO:86:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:86:

His Asp Val Gly Tyr Cys Thr Thr Pro Arg Cys Ala Lys Trp Pro Glu
    1               5                   10                  15

Tyr Phe Gln His
                20

(2) INFORMATION FOR SEQ ID NO:87:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:87:

His Asp Val Gly Tyr Cys Ser Asp Gln Thr Cys Ala Lys Trp Pro Glu
    1               5                   10                  15

Tyr Phe Gln His
                20

(2) INFORMATION FOR SEQ ID NO:88:

(i) SEQUENCE CHARACTERISTICS:
            (A) LENGTH: 20 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:88:

His Asp Val Gly Tyr Cys Asp Asp Tyr Thr Cys Ala Lys Trp Pro Glu
   1               5                  10                  15

Tyr Phe Gln His
               20

(2) INFORMATION FOR SEQ ID NO:89:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:89:

His Asp Val Gly Tyr Cys Ser Ser Ser Asn Cys Ala Val Trp Pro Glu
   1               5                  10                  15

Tyr Phe Gln His
               20

(2) INFORMATION FOR SEQ ID NO:90:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:90:

His Asp Val Gly Tyr Cys Ser Ser Asn Cys Ala Lys Trp Pro Glu
   1               5                  10                  15

Trp Leu Gly Val
               20

(2) INFORMATION FOR SEQ ID NO:91:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:91:

His Asp Val Gly Tyr Cys Ser Ser Asn Cys Ala Lys Trp Pro Glu
   1               5                  10                  15

Trp Leu Asp Asn
               20

(2) INFORMATION FOR SEQ ID NO:92:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:92:

His Asp Val Gly Tyr Cys Ser Ser Asn Cys Ala Lys Trp Pro Glu

```
              1               5              10              15

Trp Met Tyr Pro
                      20

(2) INFORMATION FOR SEQ ID NO:93:

(i) SEQUENCE CHARACTERISTICS:
           (A) LENGTH: 20 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:93:

His Asp Val Gly Tyr Cys Ser Ser Ser Asn Cys Ala Lys Trp Pro Glu
       1               5                  10                  15

Trp Met Gln Met
                      20

(2) INFORMATION FOR SEQ ID NO:94:

(i) SEQUENCE CHARACTERISTICS:
           (A) LENGTH: 20 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:94:

His Asp Val Gly Tyr Cys Ser Ser Ser Asn Cys Ala Lys Trp Pro Glu
       1               5                  10                  15

Trp Leu His Val
                      20

(2) INFORMATION FOR SEQ ID NO:95:

(i) SEQUENCE CHARACTERISTICS:
           (A) LENGTH: 20 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:95:

His Asp Val Gly Tyr Cys Ser Ser Ser Asn Cys Ala Lys Trp Pro Glu
       1               5                  10                  15

Trp Gln Asp Pro
                      20

(2) INFORMATION FOR SEQ ID NO:96:

(i) SEQUENCE CHARACTERISTICS:
           (A) LENGTH: 4 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:96:

Thr Asp Arg Thr
       1

(2) INFORMATION FOR SEQ ID NO:97:
```

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:97:

Ala Ser Trp Asp Tyr Tyr Arg Ser Gly Trp Val
1               5                   10

(2) INFORMATION FOR SEQ ID NO:98:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:98:

Ala Ser Trp Asp Ala Ser Leu Trp Gly Trp Val
1               5                   10

(2) INFORMATION FOR SEQ ID NO:99:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:99:

Ala Ala Trp Glu Gln Ser Leu Trp Gly Trp Val
1               5                   10

(2) INFORMATION FOR SEQ ID NO:100:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:100:

Ala Ala Trp Asp Tyr Ser Gln Ser Gly Trp Val
1               5                   10

(2) INFORMATION FOR SEQ ID NO:101:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:101:

Ala Ala Trp Asp Ala Ser Leu Ser Gly Trp Val
1               5                   10

(2) INFORMATION FOR SEQ ID NO:102:

(i) SEQUENCE CHARACTERISTICS:
    (A) LENGTH: 11 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:102:

Ala Ala Trp Asp Glu Gln Ile Phe Gly Trp Val
1               5                   10

(2) INFORMATION FOR SEQ ID NO:103:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:103:

Ala Ala Trp Asp Asn Arg His Ser Gly Trp Val
    1               5                   10

(2) INFORMATION FOR SEQ ID NO:104:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:104:

Ala Ala Trp Asp Asp Ser Arg Ser Gly Trp Val
    1               5                   10

(2) INFORMATION FOR SEQ ID NO:105:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:105:

Ala Ser Trp Asp Tyr Tyr Arg Ser Gly Trp Val
    1               5                   10

(2) INFORMATION FOR SEQ ID NO:106:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:106:

Thr Ala Trp Asp Tyr Ser Leu Ser Gly Trp Val
    1               5                   10

(2) INFORMATION FOR SEQ ID NO:107:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:107:

Ala Ser Trp Asp Tyr Ala Leu Ser Gly Trp Val
    1               5                   10

(2) INFORMATION FOR SEQ ID NO:108:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:108:

Ala Ala Trp Asp Tyr Ala Leu Ser Gly Trp Val
    1               5                   10

(2) INFORMATION FOR SEQ ID NO:109:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:109:

Ala Ser Trp Asp Tyr Tyr Leu Ile Gly Trp Val
    1               5                   10

(2) INFORMATION FOR SEQ ID NO:110:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:110:

CAGGAAACAG CTATGAC                                                        17

(2) INFORMATION FOR SEQ ID NO:111:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:111:

GAATTTTCTG TATGAGG                                                        17

(2) INFORMATION FOR SEQ ID NO:112:

(i) SEQUENCE CHARACTERISTICS:

(A) LENGTH: 17 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:112:

CTATGCGGCC CCATTCA                                                17

(2) INFORMATION FOR SEQ ID NO:113:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:113:

CGATCCGCCA CCGCCAGAG                                              19

(2) INFORMATION FOR SEQ ID NO:114:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:114:

TCGCGCGCAG TAATACACGG CCGTGTC                                     27

(2) INFORMATION FOR SEQ ID NO:115:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:115:

TCGCGCGCAG TAATACACAG CCGTGTCCTC                                  30

(2) INFORMATION FOR SEQ ID NO:116:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:116:

TCGCGCGCAG TAATACATGG CGGTGTCCGA                                  30

(2) INFORMATION FOR SEQ ID NO:117:

(i) SEQUENCE CHARACTERISTICS:
           (A) LENGTH: 51 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:117:

GAGTCATTCT CGACTTGCGG CCGCTCGCGC GCAGTAATAC ACGGCCGTGT C                51

(2) INFORMATION FOR SEQ ID NO:118:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:118:

GAGTCATTCT CGACTTGCGG CCGCTCGCGC GCAGTAATAC ACAGCCGTGT CCTC             54

(2) INFORMATION FOR SEQ ID NO:119:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:119:

GAGTCATTCT CGACTTGCGG CCGCTCGCGC GCAGTAATAC ATGGCGGTGT CCGA             54

(2) INFORMATION FOR SEQ ID NO:120:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:120:

AGCGCCGTGT ATTTTTGCGC GCGACATGAC GTGGGATATT GC                         42

(2) INFORMATION FOR SEQ ID NO:121:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:121:

ACCCTGGTCA CCGTCTCGAG TGGTGGA                                          27

(2) INFORMATION FOR SEQ ID NO:122:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:122:

ACAATGGTCA CCGTCTCGAG TGGTGGA                                          27

(2) INFORMATION FOR SEQ ID NO:123:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:123:

```
GAGTCATTCT CGTCTCGAGA CGGTGACCAG GGTGCC                              36
```

(2) INFORMATION FOR SEQ ID NO:124:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:124:

```
GTCCCTCCGC CGAACACCCA SNNSNNSNNS NNSNNSNNNN NSNNSNNACA GTAATAATCA    60

GCCTCAT                                                              67
```

(2) INFORMATION FOR SEQ ID NO:125:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:125:

```
GAGTCATTCT CGACTTGCGG CCGCACCTAG GACGGTCAGC TTGGTCCCTC CGCCGAACAC    60

CCA                                                                  63
```

(2) INFORMATION FOR SEQ ID NO:126:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:126:

```
GCGCAGTTGG AACTACTGCA SSSSSSSSSS SSATGTCTCG CACAAAAATA CACGGC        56
```

(2) INFORMATION FOR SEQ ID NO:127:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:127:

```
TGCAGTAGTT CCAACTGCGC                                                20
```

(2) INFORMATION FOR SEQ ID NO:128:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:128:

GTATTCAGGC CACTTTGCGC ASSSSSSSSS SSSGCAATAT CCCACGTCAT GTC        53

(2) INFORMATION FOR SEQ ID NO:129:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:129:

TGCGCAAAGT GGCCTGAATA C        21

(2) INFORMATION FOR SEQ ID NO:130:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:130:

CTGGCCCCAA TGCTGGAAGT ASSSSSSCCA SSSSSSGCAG TTGGAACTAC TGCAATATCC        60

(2) INFORMATION FOR SEQ ID NO:131:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:131:

TACTTCCAGC ATTGGGGCCA G        21

(2) INFORMATION FOR SEQ ID NO:132:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:132:

GACCAGGGTG CCCTGGCCCC ASSSSSSSSS SSSTTCAGGC CACTTTGCGC AGTTGG        56

(2) INFORMATION FOR SEQ ID NO:133:

(i) SEQUENCE CHARACTERISTICS:
        (A) LENGTH: 21 base pairs

```
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:133:

TGGGGCCAGG GCACCCTGGT C                                              21

(2) INFORMATION FOR SEQ ID NO:134:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:134:

GATACGGCAC CGGCGCACCT GCGGCCGCAT GGTGATGATG GTGATGTGCG GCACCTAGGA    60

CGGTCAGCTT GG                                                       72

(2) INFORMATION FOR SEQ ID NO:135:

(i) SEQUENCE CHARACTERISTICS:
            (A) LENGTH: 80 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:135:

CCTAGGACGG TCAGCTTGGT CCCTCCGCCG AACACCCAAC CACTCAGGGT GTAATCCCAG    60

GATGCACAGT AATAATCAGC                                               80

(2) INFORMATION FOR SEQ ID NO:136:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:136:

CCTAGGACGG TCAGCTTGGT CCCTCCGCCG AACACCCAAC CACTCAGGGT GTAATCCCAT    60

GCTGCACAG                                                           69

(2) INFORMATION FOR SEQ ID NO:137:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:137:

GACGGTGACC AGGGTGCCCT GGCCCCAAAC GTGCAGCCAT TCAGGCCACT TTGCGCA       57

(2) INFORMATION FOR SEQ ID NO:138:

(i) SEQUENCE CHARACTERISTICS:
```

(A) LENGTH: 57 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:138:

GACGGTGACC AGGGTGCCCT GGCCCCATAC GCCCAGCCAT TCAGGCCACT TTGCGCA    57

(2) INFORMATION FOR SEQ ID NO:139:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:139:

GACGGTGACC AGGGTGCCCT GGCCCCAGTT GTCCAACCAT TCAGGCCACT TTGCGCA    57

(2) INFORMATION FOR SEQ ID NO:140:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:140:

GACGGTGACC AGGGTGCCCT GGCCCCACAT CTGCATCCAT TCAGGCCACT TTGCGCA    57

(2) INFORMATION FOR SEQ ID NO:141:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:141:

GACGGTGACC AGGGTGCCCT GGCCCCAGGG GTACATCCAT TCAGGCCACT TTGCGCA    57